United States Patent
Sakaguchi et al.

(10) Patent No.: US 7,667,006 B2
(45) Date of Patent: Feb. 23, 2010

(54) ANTI-HIV ANTIBODY

(75) Inventors: Nobuo Sakaguchi, Kumamoto (JP); Kazuhiko Kuwahara, Kumamoto (JP); Chiemi Minoda, Kumamoto (JP)

(73) Assignee: Kumamoto Technology and Industry Foundation, Kaminashiki-gun (JP)

(*) Notice: Subject to any disclaimer, the term of this patent is extended or adjusted under 35 U.S.C. 154(b) by 252 days.

(21) Appl. No.: 10/582,861

(22) PCT Filed: Mar. 9, 2004

(86) PCT No.: PCT/JP2004/003046
§ 371 (c)(1), (2), (4) Date: Jan. 16, 2007

(87) PCT Pub. No.: WO2005/058963
PCT Pub. Date: Jun. 30, 2005

(65) Prior Publication Data
US 2008/0050365 A1 Feb. 28, 2008

(30) Foreign Application Priority Data
Dec. 16, 2003 (JP) .............................. 2003-418655

(51) Int. Cl.
C07K 16/08 (2006.01)
C12P 21/08 (2006.01)
C12Q 1/70 (2006.01)
C12N 5/12 (2006.01)

(52) U.S. Cl. .............................. 530/388.35; 424/141.1; 435/5; 435/70.21; 435/339.1; 530/388.15

(58) Field of Classification Search ........................ None
See application file for complete search history.

(56) References Cited

OTHER PUBLICATIONS

Hunsmann, et al. Structural and epidemiological features of primate lymphotropic retroviruses. Princess Takamatsu Symp. 1984;15:109-18.*

Laman, et al. Variant-Specific Monoclonal and Group-Specific Polyclonal Human Immunodeficiency Virus Type 1 Neutralizing Antibodies Raised with Synthetic Peptides from the gpl20 Third Variable Domain. J. Virol. 1992; 66(3):1823-1831.*

Okamoto, et al. In SCID-hu Mice, Passive Transfer of a Humanized Antibody Prevents Infection and Atrophic Change of Medulla in Human Thymic Implant due to Intravenous Inoculation of Primary HIV-1 Isolate. Journal of Immunology, 1998, 160: 69-76.*

Boudet, et al. Anti-Idiotypic Antibodies to the Third Variable Domain of gp120 Induce an Anti-HIV-I Antibody Response in Mice. Virology. 1994;200:176-188.*

(Continued)

Primary Examiner—Mary E Mosher
Assistant Examiner—Stuart W Snyder
(74) Attorney, Agent, or Firm—Birch, Stewart, Kolasch & Birch, LLP

(57) ABSTRACT

The present invention aims at providing a high affinity anti-HIV antibody. According to the present invention, there are provided an antibody or a fragment thereof that binds to the gp12 glycoprotein of HIV and has a dissociation constant (KD) value of $1.0 \times 10^{-9}$ (M) or less; a pharmaceutical composition comprising the antibody or fragment thereof; and a method of producing an anti-HIV antibody or a fragment thereof, comprising immunizing a GANP transgenic non-human mammal or a progeny thereof with a polypeptide consisting of the amino acid sequence as shown in SEQ ID NO: 6 as an antigen and collecting the antibody from the resultant mammal or progeny.

10 Claims, 7 Drawing Sheets

OTHER PUBLICATIONS

Laman J.D. et al., Journal of Virology, Mar. 1992, vol. 66, No. 3, pp. 1823 to 1831.
Boudet F. et al., Virology, 1994, vol. 200, No. 1, pp. 176 to 188.
Abe E. et al., Gene, 2000, vol. 255, No. 2, pp. 219 to 227.
Kazuhiko Kuwabara, Molecular Medicine, special extra issu, Men'eki 2004, Dec. 10, 2003, vol. 40, pp. 40 to 48.
J. S. McDougal et al., *Science*, vol. 231, Jan. 24, 1986, pp. 382-385.

* cited by examiner

```
                          SEQUENCE LISTING

<160> NUMBER OF SEQ ID NOS: 9

<210> SEQ ID NO 1
<211> LENGTH: 6429
<212> TYPE: DNA
<213> ORGANISM: Mus musclus
<220> FEATURE:
<221> NAME/KEY: CDS
<222> LOCATION: (384)..(6299)

<400> SEQUENCE: 1
gttgcggtgc ggtgggcccg gtagaggctg cacgcagact gtgggcgagc acaagcgctg      60
gcgacagtgg ccgtatctgg cggacttgct cctccctccg cggcctccgc tgtcccttgt     120
gtctttgccg agttgctgaa ggccttcact agtcttcgct cgaaggcgtc tgttaaccta     180
gcggccggct tccggagtgt taagcatcgg ggataaaaag ctattatttc tagaccaggg     240
catcgcaagt tcgagttacc gggagaaaaa tgagatggtc atcctgagga tgaaggagag     300 cttccctgg caacagataa tttaaagagg agagctactt gtgtatagtc catatttatt      360
gccttcagat aattggcttg aag atg cac ccg gtg aac ccc ttc gga ggc agc      413
                          Met His Pro Val Asn Pro Phe Gly Gly Ser
                           1               5                  10 agc cca agt gct ttt gcg gta tct tcc agc acc acg gga aca tat cag        461
Ser Pro Ser Ala Phe Ala Val Ser Ser Ser Thr Thr Gly Thr Tyr Gln
               15                  20                  25 act aaa tca cca ttt cga ttt ggc cag cct tcc ctt ttt gga cag aac        509
Thr Lys Ser Pro Phe Arg Phe Gly Gln Pro Ser Leu Phe Gly Gln Asn
           30                  35                  40 agc aca ccc agc aag agc ctg gcg ttt tca caa gta cca agc ttt gca        557
```

```
                Ser Thr Pro Ser Lys Ser Leu Ala Phe Ser Gln Val Pro Ser Phe Ala
                         45                 50                  55 aca ccc tct gga gga agc cat tct tcc tcc ttg cca gca ttt gga ctc           605
Thr Pro Ser Gly Gly Ser His Ser Ser Ser Leu Pro Ala Phe Gly Leu
         60                  65                  70 acc caa acc tca agt gtg gga ctc ttc tct agt ctc gaa tcc aca cct           653
Thr Gln Thr Ser Ser Val Gly Leu Phe Ser Ser Leu Glu Ser Thr Pro
75                  80                  85                  90 tct ttc gca gct act tcg agt tcc tct gtg ccc ggc aat acg gca ttc           701
Ser Phe Ala Ala Thr Ser Ser Ser Ser Val Pro Gly Asn Thr Ala Phe
                     95                 100                 105 agc ttt aag tca acc tct agc gtt ggg gtt ttc cca agt ggc gct act           749
Ser Phe Lys Ser Thr Ser Ser Val Gly Val Phe Pro Ser Gly Ala Thr
            110                 115                 120 ttt ggg cca gaa acc gga gaa gta gca ggt tct ggc ttt cgg aag acg           797
Phe Gly Pro Glu Thr Gly Glu Val Ala Gly Ser Gly Phe Arg Lys Thr
        125                 130                 135 gaa ttc aag ttt aaa cct ctg gaa aat gca gtc ttc aaa ccg ata ccg           845
Glu Phe Lys Phe Lys Pro Leu Glu Asn Ala Val Phe Lys Pro Ile Pro
    140                 145                 150 ggg cct gag tca gag cca gaa aaa acc cag agc cag att tct tct gga           893
Gly Pro Glu Ser Glu Pro Glu Lys Thr Gln Ser Gln Ile Ser Ser Gly
155                 160                 165                 170 ttt ttt aca ttt tcc cat ccc gtt ggt agc ggg tct gga ggc ctg acc           941
Phe Phe Thr Phe Ser His Pro Val Gly Ser Gly Ser Gly Gly Leu Thr
                175                 180                 185 cct ttt tct ttc cca cag gtg aca aat agt tcg gtg act agc tca agt           989
Pro Phe Ser Phe Pro Gln Val Thr Asn Ser Ser Val Thr Ser Ser Ser
            190                 195                 200 ttt atc ttt tcg aaa cca gtt act agt aat act cct gcc ttt gcc tct          1037
Phe Ile Phe Ser Lys Pro Val Thr Ser Asn Thr Pro Ala Phe Ala Ser
        205                 210                 215 cct ttg tct aac caa aat gta gaa gaa gag aag agg gtt tct acg tca          1085
Pro Leu Ser Asn Gln Asn Val Glu Glu Glu Lys Arg Val Ser Thr Ser
    220                 225                 230 gcg ttt gga agc tca aac agt agc ttc agt act ttc ccc aca gcg tca          1133
Ala Phe Gly Ser Ser Asn Ser Ser Phe Ser Thr Phe Pro Thr Ala Ser
235                 240                 245                 250 cca gga tct ttg ggg gag ccc ttc cca gct aac aaa cca agc ctc cgc          1181
Pro Gly Ser Leu Gly Glu Pro Phe Pro Ala Asn Lys Pro Ser Leu Arg
                255                 260                 265 caa gga tgt gag gaa gcc atc tcc cag gtg gag cca ctt ccc acc ctc          1229
Gln Gly Cys Glu Glu Ala Ile Ser Gln Val Glu Pro Leu Pro Thr Leu
            270                 275                 280 atg aag gga tta aag agg aaa gag gac cag gat cgc tcc ccg agg aga          1277
Met Lys Gly Leu Lys Arg Lys Glu Asp Gln Asp Arg Ser Pro Arg Arg
        285                 290                 295 cat tgc cac gag gca gca gaa gac cct gat ccc ctg tcc agg ggc gac          1325
His Cys His Glu Ala Ala Glu Asp Pro Asp Pro Leu Ser Arg Gly Asp
    300                 305                 310 cat ccc cca gat aaa cgg cca gtc cgc ctc aac aga ccc cgg gga ggt          1373
His Pro Pro Asp Lys Arg Pro Val Arg Leu Asn Arg Pro Arg Gly Gly
315                 320                 325                 330 act ttg ttt ggc cgg aca ata cag gag gtc ttc aaa agc aat aaa gag          1421
Thr Leu Phe Gly Arg Thr Ile Gln Glu Val Phe Lys Ser Asn Lys Glu
                335                 340                 345 gca ggc cgc ctg ggc agc aag gaa tcc aag gag agt ggc ttt gcg gaa          1469
Ala Gly Arg Leu Gly Ser Lys Glu Ser Lys Glu Ser Gly Phe Ala Glu
            350                 355                 360
```

```
cct ggg gaa agt gac cac gcg gcc gtc cca gga ggg agt cag tcc acc      1517
Pro Gly Glu Ser Asp His Ala Ala Val Pro Gly Gly Ser Gln Ser Thr
        365                 370                 375 atg gta cct tcc cgc ctt cca gct gtg act aaa gag gaa gaa gaa agt      1565
Met Val Pro Ser Arg Leu Pro Ala Val Thr Lys Glu Glu Glu Glu Ser
    380                 385                 390 aga gat gag aaa gaa gat tct ctc agg gga aag tct gtg cgc cag agt      1613
Arg Asp Glu Lys Glu Asp Ser Leu Arg Gly Lys Ser Val Arg Gln Ser
395                 400                 405                 410 aag cga agg gaa gag tgg atc tac agc ctc ggg ggc gtg tct tct tta      1661
Lys Arg Arg Glu Glu Trp Ile Tyr Ser Leu Gly Gly Val Ser Ser Leu
                415                 420                 425 gag ctc aca gcc atc cag tgc aag aac atc ccc gac tac ctc aac gac      1709
Glu Leu Thr Ala Ile Gln Cys Lys Asn Ile Pro Asp Tyr Leu Asn Asp
            430                 435                 440 aga gcc atc ctg gag aaa cac ttc agc aaa atc gct aaa gtc cag cgg      1757
Arg Ala Ile Leu Glu Lys His Phe Ser Lys Ile Ala Lys Val Gln Arg
        445                 450                 455 gtc ttc acc aga cgc agc aag aag ctc gcc gtg att cat ttt ttc gac      1805
Val Phe Thr Arg Arg Ser Lys Lys Leu Ala Val Ile His Phe Phe Asp
    460                 465                 470 cac gca tcg gca gcc ctg gct agg aag aag ggg aaa ggt ctg cat aag      1853
His Ala Ser Ala Ala Leu Ala Arg Lys Lys Gly Lys Gly Leu His Lys
475                 480                 485                 490 gac gtg gtt atc ttt tgg cac aag aag aaa ata agt ccc agc aag aaa      1901
Asp Val Val Ile Phe Trp His Lys Lys Lys Ile Ser Pro Ser Lys Lys
                495                 500                 505 ctc ttt ccc ctg aag gag aag ctt ggt gag agt gaa gcc agc cag ggc      1949
Leu Phe Pro Leu Lys Glu Lys Leu Gly Glu Ser Glu Ala Ser Gln Gly
            510                 515                 520 atc gag gac tcc ccc ttt cag cac tcg cct ctc agc aag ccc atc gtg      1997
Ile Glu Asp Ser Pro Phe Gln His Ser Pro Leu Ser Lys Pro Ile Val
        525                 530                 535 agg cct gca gcc ggc agc ctc ctc agc aaa agc tct cca gtg aag aag      2045
Arg Pro Ala Ala Gly Ser Leu Leu Ser Lys Ser Ser Pro Val Lys Lys
    540                 545                 550 ccg agt ctt ctg aag atg cac cag ttt gag gcg gat cct ttt gac tct      2093
Pro Ser Leu Leu Lys Met His Gln Phe Glu Ala Asp Pro Phe Asp Ser
555                 560                 565                 570 gga tct gag ggc tcc gag ggc ctt ggt tct tgc gtg tca tct ctt agc      2141
Gly Ser Glu Gly Ser Glu Gly Leu Gly Ser Cys Val Ser Ser Leu Ser
                575                 580                 585 acc ctg ata ggg act gtg gca gac aca tct gag gag aag tac cgc ctt      2189
Thr Leu Ile Gly Thr Val Ala Asp Thr Ser Glu Glu Lys Tyr Arg Leu
            590                 595                 600 ctg gac cag aga gac cgc atc atg cgg caa gct cga gtg aag agg acg      2237
Leu Asp Gln Arg Asp Arg Ile Met Arg Gln Ala Arg Val Lys Arg Thr
        605                 610                 615 gac ctg gac aaa gcc agg gca ttt gtt ggg act tgc cct gac atg tgt      2285
Asp Leu Asp Lys Ala Arg Ala Phe Val Gly Thr Cys Pro Asp Met Cys
    620                 625                 630 ccc gag aag gag cgg tac ttg agg gag acc cgg agc cag ctg agc gtg      2333
Pro Glu Lys Glu Arg Tyr Leu Arg Glu Thr Arg Ser Gln Leu Ser Val
635                 640                 645                 650 ttt gaa gtt gtc cca ggg act gac cag gtg gac cat gca gca gcc gtg      2381
Phe Glu Val Val Pro Gly Thr Asp Gln Val Asp His Ala Ala Ala Val
                655                 660                 665 aag gag tac agc cgg tcc tct gca gat cag gag gag ccc ctg cca cat      2429
Lys Glu Tyr Ser Arg Ser Ser Ala Asp Gln Glu Glu Pro Leu Pro His
            670                 675                 680
```

| | |
|---|---|
| gag ctg aga ccc tca gca gtt ctc agc agg acc atg gac tac ctg gtg<br>Glu Leu Arg Pro Ser Ala Val Leu Ser Arg Thr Met Asp Tyr Leu Val<br>685 690 695 | 2477 |
| acc cag atc atg gac caa aag gaa ggc agc ctt cgg gat tgg tat gac<br>Thr Gln Ile Met Asp Gln Lys Glu Gly Ser Leu Arg Asp Trp Tyr Asp<br>700 705 710 | 2525 |
| ttc gtg tgg aac cgc acc cgg ggt ata cgg aag gac ata aca cag cag<br>Phe Val Trp Asn Arg Thr Arg Gly Ile Arg Lys Asp Ile Thr Gln Gln<br>715 720 725 730 | 2573 |
| cac ctc tgt gat ccc ctg acg gtg tct ctg atc gag aag tgt acc cga<br>His Leu Cys Asp Pro Leu Thr Val Ser Leu Ile Glu Lys Cys Thr Arg<br>735 740 745 | 2621 |
| ttt cac att cac tgt gcc cac ttt atg tgt gag gag cct atg tct tcc<br>Phe His Ile His Cys Ala His Phe Met Cys Glu Glu Pro Met Ser Ser<br>750 755 760 | 2669 |
| ttt gat gcc aag atc aac aat gag aac atg acc aag tgt cta cag agt<br>Phe Asp Ala Lys Ile Asn Asn Glu Asn Met Thr Lys Cys Leu Gln Ser<br>765 770 775 | 2717 |
| ctg aag gag atg tac cag gac ctg agg aac aag ggt gtt ttt tgt gcc<br>Leu Lys Glu Met Tyr Gln Asp Leu Arg Asn Lys Gly Val Phe Cys Ala<br>780 785 790 | 2765 |
| agt gaa gca gag ttt cag ggc tac aat gtc ctg ctt aat ctc aac aaa<br>Ser Glu Ala Glu Phe Gln Gly Tyr Asn Val Leu Leu Asn Leu Asn Lys<br>795 800 805 810 | 2813 |
| gga gac att ttg aga gaa gtg cag cag ttc cac cct gac gtt agg aac<br>Gly Asp Ile Leu Arg Glu Val Gln Gln Phe His Pro Asp Val Arg Asn<br>815 820 825 | 2861 |
| tcc cca gag gtg aac ttc gct gtc cag gct ttt gct gca ttg aac agc<br>Ser Pro Glu Val Asn Phe Ala Val Gln Ala Phe Ala Ala Leu Asn Ser<br>830 835 840 | 2909 |
| aat aat ttt gtg aga ttt ttc aaa ctg gtt cag tca gct tct tac ctg<br>Asn Asn Phe Val Arg Phe Phe Lys Leu Val Gln Ser Ala Ser Tyr Leu<br>845 850 855 | 2957 |
| aat gcg tgc ctg tta cac tgt tac ttt aat cag atc cgc aag gat gcc<br>Asn Ala Cys Leu Leu His Cys Tyr Phe Asn Gln Ile Arg Lys Asp Ala<br>860 865 870 | 3005 |
| ctc cgg gca ctc aat gtt gct tat act gta agc aca cag cgc tct acc<br>Leu Arg Ala Leu Asn Val Ala Tyr Thr Val Ser Thr Gln Arg Ser Thr<br>875 880 885 890 | 3053 |
| gtc ttc ccc ctg gat ggt gtc gtc cgc atg ctg ctg ttc aga gat agt<br>Val Phe Pro Leu Asp Gly Val Val Arg Met Leu Leu Phe Arg Asp Ser<br>895 900 905 | 3101 |
| gaa gag gcg aca aac ttc ctc aat tac cat ggc ctc act gta gct gat<br>Glu Glu Ala Thr Asn Phe Leu Asn Tyr His Gly Leu Thr Val Ala Asp<br>910 915 920 | 3149 |
| ggc tgt gtt gag ctg aat cgg tcg gca ttc ttg gaa ccg gag gga tta<br>Gly Cys Val Glu Leu Asn Arg Ser Ala Phe Leu Glu Pro Glu Gly Leu<br>925 930 935 | 3197 |
| tgc aag gcc agg aag tca gtg ttt att ggc cgg aag ctg acg gtg tca<br>Cys Lys Ala Arg Lys Ser Val Phe Ile Gly Arg Lys Leu Thr Val Ser<br>940 945 950 | 3245 |
| gtt ggg gaa gtt gtg aat gga ggg ccg ttg ccc cct gtt cct cgc cat<br>Val Gly Glu Val Val Asn Gly Gly Pro Leu Pro Pro Val Pro Arg His<br>955 960 965 970 | 3293 |
| aca cct gtg tgc agc ttc aac tcc cag aat aag tac gtt gga gag agc<br>Thr Pro Val Cys Ser Phe Asn Ser Gln Asn Lys Tyr Val Gly Glu Ser<br>975 980 985 | 3341 |
| ctg gct acg gag ctg ccc atc agc act cag aga gct ggt gga gac cca<br>Leu Ala Thr Glu Leu Pro Ile Ser Thr Gln Arg Ala Gly Gly Asp Pro | 3389 |

```
                           -continued 990             995            1000 gca ggt ggt ggc aga gga gag gac tgt gag gca gag gtg gac ttg    3434
Ala Gly Gly Gly Arg Gly Glu Asp Cys Glu Ala Glu Val Asp Leu
        1005            1010           1015 cca aca ttg gcg gtc ctc cca cag ccg cct cct gca tcc tca gcc    3479
Pro Thr Leu Ala Val Leu Pro Gln Pro Pro Pro Ala Ser Ser Ala
        1020            1025           1030 acg ccg gcg ctt cat gtc cag cca ctg gcc cca gcc gca ccc        3524
Thr Pro Ala Leu His Val Gln Pro Leu Ala Pro Ala Ala Pro
        1035            1040           1045 agc ctt ctc cag gcc tcc acg cag cct gag gtg ctg ctt cca aag    3569
Ser Leu Leu Gln Ala Ser Thr Gln Pro Glu Val Leu Leu Pro Lys
        1050            1055           1060 cct gcg cct gtg tac tct gac tcg gac ctg gta cag gtg gtg gac    3614
Pro Ala Pro Val Tyr Ser Asp Ser Asp Leu Val Gln Val Val Asp
        1065            1070           1075 gag ctc atc cag gag gct ctg caa gtg gac tgt gag gaa gtc agc    3659
Glu Leu Ile Gln Glu Ala Leu Gln Val Asp Cys Glu Glu Val Ser
        1080            1085           1090 tcc gct ggg gca gcc tac gta gcc gca gct ctg ggc gtt tcc aat    3704
Ser Ala Gly Ala Ala Tyr Val Ala Ala Ala Leu Gly Val Ser Asn
        1095            1100           1105 gct gct gtg gag gat ctg att act gct gcg acc acg ggc att ctg    3749
Ala Ala Val Glu Asp Leu Ile Thr Ala Ala Thr Thr Gly Ile Leu
        1110            1115           1120 agg cac gtt gcc gct gag gaa gtt tcc atg gaa agg cag aga cta    3794
Arg His Val Ala Ala Glu Glu Val Ser Met Glu Arg Gln Arg Leu
        1125            1130           1135 gag gaa gag aag caa cga gct gag gag gaa cgg ttg aag caa gag    3839
Glu Glu Glu Lys Gln Arg Ala Glu Glu Glu Arg Leu Lys Gln Glu
        1140            1145           1150 aga gaa ctg atg tta act cag ctg agc gag ggt ctg gcc gca gag    3884
Arg Glu Leu Met Leu Thr Gln Leu Ser Glu Gly Leu Ala Ala Glu
        1155            1160           1165 ctg aca gaa ctc acg gtg aca gag tgt gtg tgg gaa acc tgc tct    3929
Leu Thr Glu Leu Thr Val Thr Glu Cys Val Trp Glu Thr Cys Ser
        1170            1175           1180 cag gag cta cag agt gca gta aaa ata gac cag aag gtc cgt gtg    3974
Gln Glu Leu Gln Ser Ala Val Lys Ile Asp Gln Lys Val Arg Val
        1185            1190           1195 gcc cgc tgt tgt gaa gcc gtc tgt gca cac ctg gtg gat ttg ttt    4019
Ala Arg Cys Cys Glu Ala Val Cys Ala His Leu Val Asp Leu Phe
        1200            1205           1210 ctt gct gag gaa att ttc cag act gca aaa gag aca ctc cag gaa    4064
Leu Ala Glu Glu Ile Phe Gln Thr Ala Lys Glu Thr Leu Gln Glu
        1215            1220           1225 ctc cag tgt ttc tgc aag tat cta caa cgg tgg agg gag gct gtt    4109
Leu Gln Cys Phe Cys Lys Tyr Leu Gln Arg Trp Arg Glu Ala Val
        1230            1235           1240 gca gct cgg aag aaa ttc cgg cgt cag atg cgg gcc ttc cct gca    4154
Ala Ala Arg Lys Lys Phe Arg Arg Gln Met Arg Ala Phe Pro Ala
        1245            1250           1255 gcg cca tgc tgt gtg gat gtg aat gac cgg ctg cag gca cta gtg    4199
Ala Pro Cys Cys Val Asp Val Asn Asp Arg Leu Gln Ala Leu Val
        1260            1265           1270 ccc agc gca gag tgc ccc att act gag gag aac ctg gcc aag ggt    4244
Pro Ser Ala Glu Cys Pro Ile Thr Glu Glu Asn Leu Ala Lys Gly
        1275            1280           1285 ctt ttg gac ctg ggc cac gca ggc aaa gta ggc gtc tcc tgt acc    4289
```

```
              Leu Leu Asp Leu Gly His Ala Gly Lys Val Gly Val Ser Cys Thr
                      1290                1295                1300 agg ttg agg cgg ctt aga aac aag aca gct cac cag ata aag gtc         4334
Arg Leu Arg Arg Leu Arg Asn Lys Thr Ala His Gln Ile Lys Val
            1305                1310                1315 cag cac ttc cac cag cag ctg ctg agg aat gct gca tgg gca cct         4379
Gln His Phe His Gln Gln Leu Leu Arg Asn Ala Ala Trp Ala Pro
            1320                1325                1330 ctg gac ctg cca tcc att gtg tct gag cac ctc ccc atg aag cag         4424
Leu Asp Leu Pro Ser Ile Val Ser Glu His Leu Pro Met Lys Gln
            1335                1340                1345 aag cga agg ttt tgg aaa ctg gtg ctg gtg ttg cct gat gtg gaa         4469
Lys Arg Arg Phe Trp Lys Leu Val Leu Val Leu Pro Asp Val Glu
            1350                1355                1360 gag cag act cca gag agt cct ggc aga ata cta gaa aac tgg cta         4514
Glu Gln Thr Pro Glu Ser Pro Gly Arg Ile Leu Glu Asn Trp Leu
            1365                1370                1375 aag gtc aaa ttc aca gga gat gac agc atg gtg ggt gac ata gga         4559
Lys Val Lys Phe Thr Gly Asp Asp Ser Met Val Gly Asp Ile Gly
            1380                1385                1390 gat aat gct ggt gat atc cag acc ctc tca gtc ttt aat aca ctt         4604
Asp Asn Ala Gly Asp Ile Gln Thr Leu Ser Val Phe Asn Thr Leu
            1395                1400                1405 agt agt aaa ggg gat caa aca gtt tct gtc aac gtg tgt ata aag         4649
Ser Ser Lys Gly Asp Gln Thr Val Ser Val Asn Val Cys Ile Lys
            1410                1415                1420 gtg gct cat ggc acc ctt agt gac agt gcc ctt gat gct gtg gag         4694
Val Ala His Gly Thr Leu Ser Asp Ser Ala Leu Asp Ala Val Glu
            1425                1430                1435 acc cag aag gac ctg ttg gga acc agt ggg ctc atg ctg ctg ctt         4739
Thr Gln Lys Asp Leu Leu Gly Thr Ser Gly Leu Met Leu Leu Leu
            1440                1445                1450 ccc ccg aaa gtg aag agt gag gag gtg gca gag gag gaa ctg tcc         4784
Pro Pro Lys Val Lys Ser Glu Glu Val Ala Glu Glu Glu Leu Ser
            1455                1460                1465 tgg ctg tcg gct tta ctg cag ctc aag cag ctt ctg cag gcc aag         4829
Trp Leu Ser Ala Leu Leu Gln Leu Lys Gln Leu Leu Gln Ala Lys
            1470                1475                1480 ccc ttc cag cct gcc ctg ccg ctg gtg gtc ctc gtg ccc agc tcc         4874
Pro Phe Gln Pro Ala Leu Pro Leu Val Val Leu Val Pro Ser Ser
            1485                1490                1495 aga ggg gac tcc gcg ggg agg gca gta gag gac ggt ctg atg tta         4919
Arg Gly Asp Ser Ala Gly Arg Ala Val Glu Asp Gly Leu Met Leu
            1500                1505                1510 cag gat ttg gtt tca gcc aag ctg att tcc gat tac att gtt gtt         4964
Gln Asp Leu Val Ser Ala Lys Leu Ile Ser Asp Tyr Ile Val Val
            1515                1520                1525 gag att cct gac tct gtt aat gat tta caa ggc aca gtg aag gtt         5009
Glu Ile Pro Asp Ser Val Asn Asp Leu Gln Gly Thr Val Lys Val
            1530                1535                1540 tct gga gca gtc cag tgg ctg atc tcc gga tgt cct caa gcc cta         5054
Ser Gly Ala Val Gln Trp Leu Ile Ser Gly Cys Pro Gln Ala Leu
            1545                1550                1555 gac ctt tgc tgc cag acc ctt gtt cag tat gtt gag gat ggg atc         5099
Asp Leu Cys Cys Gln Thr Leu Val Gln Tyr Val Glu Asp Gly Ile
            1560                1565                1570 agc cgc gag ttc agc cgt cgg ttt ttc cac gac agg aga gag agg         5144
Ser Arg Glu Phe Ser Arg Arg Phe Phe His Asp Arg Arg Glu Arg
            1575                1580                1585
```

```
cgc ctg gct agc ctg ccc tcc cag gag cct agc acc att att gag      5189
Arg Leu Ala Ser Leu Pro Ser Gln Glu Pro Ser Thr Ile Ile Glu
        1590                1595                1600 ttg ttc aac agt gtg ctg cag ttc ctg gcc tct gtg gta tcc tct      5234
Leu Phe Asn Ser Val Leu Gln Phe Leu Ala Ser Val Val Ser Ser
1605                1610                1615 gag cag ctg tgt gac atc tcc tgg cct gtc atg gaa ttt gcc gaa      5279
Glu Gln Leu Cys Asp Ile Ser Trp Pro Val Met Glu Phe Ala Glu
            1620                1625                1630 gtg gga ggc agc cag ctg ctt cct cac ctg cac tgg aac tca cca      5324
Val Gly Gly Ser Gln Leu Leu Pro His Leu His Trp Asn Ser Pro
        1635                1640                1645 gag cat cta gcg tgg ctg aaa caa gct gtg ctt ggg ttc cag ctt      5369
Glu His Leu Ala Trp Leu Lys Gln Ala Val Leu Gly Phe Gln Leu
1650                1655                1660 cca cag atg gac ctt cca ccc cca ggg gcc ccc tgg ctc cct gtg      5414
Pro Gln Met Asp Leu Pro Pro Pro Gly Ala Pro Trp Leu Pro Val
            1665                1670                1675 tgt tcc atg gtc att cag tac acc tcc cag att ccc agc tca agc      5459
Cys Ser Met Val Ile Gln Tyr Thr Ser Gln Ile Pro Ser Ser Ser
        1680                1685                1690 cag aca cag cct gtc ctc cag tcc cag gcg gag aac ctg ctg tgc      5504
Gln Thr Gln Pro Val Leu Gln Ser Gln Ala Glu Asn Leu Leu Cys
1695                1700                1705 aga aca tac cag aag tgg aag aac aag agc ctc tct cca ggc cag      5549
Arg Thr Tyr Gln Lys Trp Lys Asn Lys Ser Leu Ser Pro Gly Gln
            1710                1715                1720 gag ttg ggg cct tct gtt gcc gag atc ccg tgg gat gac atc atc      5594
Glu Leu Gly Pro Ser Val Ala Glu Ile Pro Trp Asp Asp Ile Ile
        1725                1730                1735 acc tta tgc atc aat cat aag ctg agg gac tgg aca ccc ccc agg      5639
Thr Leu Cys Ile Asn His Lys Leu Arg Asp Trp Thr Pro Pro Arg
1740                1745                1750 ctc cct gtc aca tta gag gcg ctg agt gaa gat ggt caa ata tgt      5684
Leu Pro Val Thr Leu Glu Ala Leu Ser Glu Asp Gly Gln Ile Cys
            1755                1760                1765 gtg tat ttt ttc aaa aac ctt tta aga aaa tac cac gtt ccc tcg      5729
Val Tyr Phe Phe Lys Asn Leu Leu Arg Lys Tyr His Val Pro Ser
        1770                1775                1780 tca tgg gaa cag gcc aga atg cag acg cag cgg gaa ctg cag ctg      5774
Ser Trp Glu Gln Ala Arg Met Gln Thr Gln Arg Glu Leu Gln Leu
1785                1790                1795 agt cat gga cgt tcg ggg atg agg tcc atc cat cct cct aca agc      5819
Ser His Gly Arg Ser Gly Met Arg Ser Ile His Pro Pro Thr Ser
            1800                1805                1810 act ttt cct act cca ttg ctt cat gta cac cag aaa ggg aag aaa      5864
Thr Phe Pro Thr Pro Leu Leu His Val His Gln Lys Gly Lys Lys
        1815                1820                1825 aag gaa gag agt ggc cga gag ggg agc ctc agt aca gag gac ctc      5909
Lys Glu Glu Ser Gly Arg Glu Gly Ser Leu Ser Thr Glu Asp Leu
1830                1835                1840 ctg cgg ggg gct tct gca gaa gag ctc ctg gca cag agt ctg tcc      5954
Leu Arg Gly Ala Ser Ala Glu Glu Leu Leu Ala Gln Ser Leu Ser
            1845                1850                1855 agc agt ctt ctg gaa gag aag gaa gag aac aag agg ttt gaa gat      5999
Ser Ser Leu Leu Glu Glu Lys Glu Glu Asn Lys Arg Phe Glu Asp
        1860                1865                1870 caa ctt cag cag tgg tta tcg caa gac tca cag gca ttc aca gag      6044
Gln Leu Gln Gln Trp Leu Ser Gln Asp Ser Gln Ala Phe Thr Glu
1875                1880                1885
```

-continued

```
tca act cgg ctt cct ctc tac ctc cct cag acg cta gtg tcc ttt    6089
Ser Thr Arg Leu Pro Leu Tyr Leu Pro Gln Thr Leu Val Ser Phe
        1890            1895            1900 cct gat tct atc aaa act cag acc atg gtg aaa aca tct aca agt    6134
Pro Asp Ser Ile Lys Thr Gln Thr Met Val Lys Thr Ser Thr Ser
    1905            1910            1915 cct cag aat tca gga aca gga aag cag ttg agg ttc tca gag gca    6179
Pro Gln Asn Ser Gly Thr Gly Lys Gln Leu Arg Phe Ser Glu Ala
        1920            1925            1930 tcc ggt tca tcc ctg acg gaa aag ctg aag ctc ctg gaa agg ctg    6224
Ser Gly Ser Ser Leu Thr Glu Lys Leu Lys Leu Leu Glu Arg Leu
        1935            1940            1945 atc cag agc tca agg gcg gaa gaa gca gcc tcc gag ctg cac ctc    6269
Ile Gln Ser Ser Arg Ala Glu Glu Ala Ala Ser Glu Leu His Leu
        1950            1955            1960 tct gca ctg ctg gag atg gtg gac atg tag ctgtctgacg ggagacggat  6319
Ser Ala Leu Leu Glu Met Val Asp Met
        1965            1970 ctctaattca taatgctttg tctgtattca attgtgttat agatgctgtt ggaaatgtga  6379
ctattaatta tgcaaataaa cttttttgaat cattccaaaa aaaaaaccat           6429

<210> SEQ ID NO 2
<211> LENGTH: 1971
<212> TYPE: PRT
<213> ORGANISM: Mus musclus

<400> SEQUENCE: 2

Met His Pro Val Asn Pro Phe Gly Gly Ser Pro Ser Ala Phe Ala
1               5                   10                  15

Val Ser Ser Ser Thr Thr Gly Thr Tyr Gln Thr Lys Ser Pro Phe Arg
                20                  25                  30

Phe Gly Gln Pro Ser Leu Phe Gly Gln Asn Ser Thr Pro Ser Lys Ser
            35                  40                  45

Leu Ala Phe Ser Gln Val Pro Ser Phe Ala Thr Pro Ser Gly Gly Ser
        50                  55                  60

His Ser Ser Ser Leu Pro Ala Phe Gly Leu Thr Gln Thr Ser Ser Val
65                  70                  75                  80

Gly Leu Phe Ser Ser Leu Glu Ser Thr Pro Ser Phe Ala Ala Thr Ser
                85                  90                  95

Ser Ser Ser Val Pro Gly Asn Thr Ala Phe Ser Phe Lys Ser Thr Ser
            100                 105                 110

Ser Val Gly Val Phe Pro Ser Gly Ala Thr Phe Gly Pro Glu Thr Gly
        115                 120                 125

Glu Val Ala Gly Ser Gly Phe Arg Lys Thr Glu Phe Lys Phe Lys Pro
    130                 135                 140

Leu Glu Asn Ala Val Phe Lys Pro Ile Pro Gly Pro Glu Ser Glu Pro
145                 150                 155                 160

Glu Lys Thr Gln Ser Gln Ile Ser Ser Gly Phe Phe Thr Phe Ser His
                165                 170                 175

Pro Val Gly Ser Gly Gly Leu Thr Pro Phe Ser Phe Pro Gln
            180                 185                 190

Val Thr Asn Ser Ser Val Thr Ser Ser Phe Ile Phe Ser Lys Pro
        195                 200                 205

Val Thr Ser Asn Thr Pro Ala Phe Ala Ser Pro Leu Ser Asn Gln Asn
    210                 215                 220
```

-continued

| | | | | | | | | | | | | | | |
|---|---|---|---|---|---|---|---|---|---|---|---|---|---|---|
|Val|Glu|Glu|Glu|Lys|Arg|Val|Ser|Thr|Ser|Ala|Phe|Gly|Ser|Ser|Asn|
|225| | | | |230| | | | |235| | | | |240|

Ser Ser Phe Ser Thr Phe Pro Thr Ala Ser Pro Gly Ser Leu Gly Glu
               245                250              255

Pro Phe Pro Ala Asn Lys Pro Ser Leu Arg Gln Gly Cys Glu Glu Ala
            260              265            270

Ile Ser Gln Val Glu Pro Leu Pro Thr Leu Met Lys Gly Leu Lys Arg
     275               280              285

Lys Glu Asp Gln Asp Arg Ser Pro Arg Arg His Cys His Glu Ala Ala
    290              295            300

Glu Asp Pro Asp Pro Leu Ser Arg Gly Asp His Pro Pro Asp Lys Arg
305             310             315            320

Pro Val Arg Leu Asn Arg Pro Arg Gly Gly Thr Leu Phe Gly Arg Thr
            325              330           335

Ile Gln Glu Val Phe Lys Ser Asn Lys Glu Ala Gly Arg Leu Gly Ser
         340             345           350

Lys Glu Ser Lys Glu Ser Gly Phe Ala Glu Pro Gly Glu Ser Asp His
    355              360            365

Ala Ala Val Pro Gly Gly Ser Gln Ser Thr Met Val Pro Ser Arg Leu
    370              375            380

Pro Ala Val Thr Lys Glu Glu Glu Ser Arg Asp Glu Lys Glu Asp
385             390             395            400

Ser Leu Arg Gly Lys Ser Val Arg Gln Ser Lys Arg Arg Glu Glu Trp
            405              410           415

Ile Tyr Ser Leu Gly Gly Val Ser Ser Leu Glu Leu Thr Ala Ile Gln
         420             425           430

Cys Lys Asn Ile Pro Asp Tyr Leu Asn Asp Arg Ala Ile Leu Glu Lys
    435              440            445

His Phe Ser Lys Ile Ala Lys Val Gln Arg Val Phe Thr Arg Arg Ser
    450              455            460

Lys Lys Leu Ala Val Ile His Phe Asp His Ala Ser Ala Ala Leu
465             470             475            480

Ala Arg Lys Lys Gly Lys Gly Leu His Lys Asp Val Val Ile Phe Trp
            485              490           495

His Lys Lys Lys Ile Ser Pro Ser Lys Lys Leu Phe Pro Leu Lys Glu
         500             505           510

Lys Leu Gly Glu Ser Glu Ala Ser Gln Gly Ile Glu Asp Ser Pro Phe
        515            520            525

Gln His Ser Pro Leu Ser Lys Pro Ile Val Arg Pro Ala Ala Gly Ser
    530              535            540

Leu Leu Ser Lys Ser Ser Pro Val Lys Lys Pro Ser Leu Leu Lys Met
545             550             555            560

His Gln Phe Glu Ala Asp Pro Phe Asp Ser Gly Ser Glu Gly Ser Glu
            565              570           575

Gly Leu Gly Ser Cys Val Ser Ser Leu Ser Thr Leu Ile Gly Thr Val
         580             585           590

Ala Asp Thr Ser Glu Glu Lys Tyr Arg Leu Leu Asp Gln Arg Asp Arg
        595            600            605

Ile Met Arg Gln Ala Arg Val Lys Arg Thr Asp Leu Asp Lys Ala Arg
    610              615            620

Ala Phe Val Gly Thr Cys Pro Asp Met Cys Pro Glu Lys Glu Arg Tyr
625             630             635            640

Leu Arg Glu Thr Arg Ser Gln Leu Ser Val Phe Glu Val Val Pro Gly

-continued

```
                645                 650                 655
Thr Asp Gln Val Asp His Ala Ala Val Lys Glu Tyr Ser Arg Ser
            660                 665                 670
Ser Ala Asp Gln Glu Glu Pro Leu Pro His Glu Leu Arg Pro Ser Ala
        675                 680                 685
Val Leu Ser Arg Thr Met Asp Tyr Leu Val Thr Gln Ile Met Asp Gln
        690                 695                 700
Lys Glu Gly Ser Leu Arg Asp Trp Tyr Asp Phe Val Trp Asn Arg Thr
705                 710                 715                 720
Arg Gly Ile Arg Lys Asp Ile Thr Gln Gln His Leu Cys Asp Pro Leu
                725                 730                 735
Thr Val Ser Leu Ile Glu Lys Cys Thr Arg Phe His Ile His Cys Ala
            740                 745                 750
His Phe Met Cys Glu Glu Pro Met Ser Ser Phe Asp Ala Lys Ile Asn
            755                 760                 765
Asn Glu Asn Met Thr Lys Cys Leu Gln Ser Leu Lys Glu Met Tyr Gln
        770                 775                 780
Asp Leu Arg Asn Lys Gly Val Phe Cys Ala Ser Glu Ala Glu Phe Gln
785                 790                 795                 800
Gly Tyr Asn Val Leu Leu Asn Leu Asn Lys Gly Asp Ile Leu Arg Glu
                805                 810                 815
Val Gln Gln Phe His Pro Asp Val Arg Asn Ser Pro Glu Val Asn Phe
            820                 825                 830
Ala Val Gln Ala Phe Ala Ala Leu Asn Ser Asn Asn Phe Val Arg Phe
            835                 840                 845
Phe Lys Leu Val Gln Ser Ala Ser Tyr Leu Asn Ala Cys Leu Leu His
        850                 855                 860
Cys Tyr Phe Asn Gln Ile Arg Lys Asp Ala Leu Arg Ala Leu Asn Val
865                 870                 875                 880
Ala Tyr Thr Val Ser Thr Gln Arg Ser Thr Val Phe Pro Leu Asp Gly
                885                 890                 895
Val Val Arg Met Leu Leu Phe Arg Asp Ser Glu Glu Ala Thr Asn Phe
            900                 905                 910
Leu Asn Tyr His Gly Leu Thr Val Ala Asp Gly Cys Val Glu Leu Asn
        915                 920                 925
Arg Ser Ala Phe Leu Glu Pro Glu Gly Leu Cys Lys Ala Arg Lys Ser
        930                 935                 940
Val Phe Ile Gly Arg Lys Leu Thr Val Ser Val Gly Glu Val Val Asn
945                 950                 955                 960
Gly Gly Pro Leu Pro Pro Val Pro Arg His Thr Pro Val Cys Ser Phe
                965                 970                 975
Asn Ser Gln Asn Lys Tyr Val Gly Glu Ser Leu Ala Thr Glu Leu Pro
            980                 985                 990
Ile Ser Thr Gln Arg Ala Gly Gly Asp Pro Ala Gly Gly Gly Arg Gly
            995                 1000                1005
Glu Asp Cys Glu Ala Glu Val Asp Leu Pro Thr Leu Ala Val Leu
        1010                1015                1020
Pro Gln Pro Pro Ala Ser Ser Ala Thr Pro Ala Leu His Val
    1025                1030                1035
Gln Pro Leu Ala Pro Ala Ala Pro Ser Leu Leu Gln Ala Ser
        1040                1045                1050
Thr Gln Pro Glu Val Leu Leu Pro Lys Pro Ala Pro Val Tyr Ser
        1055                1060                1065
```

-continued

```
Asp Ser Asp Leu Val Gln Val Val Asp Glu Leu Ile Gln Glu Ala
    1070            1075                1080
Leu Gln Val Asp Cys Glu Glu Val Ser Ser Ala Gly Ala Ala Tyr
    1085            1090                1095
Val Ala Ala Ala Leu Gly Val Ser Asn Ala Ala Val Glu Asp Leu
    1100            1105                1110
Ile Thr Ala Ala Thr Thr Gly Ile Leu Arg His Val Ala Ala Glu
    1115            1120                1125
Glu Val Ser Met Glu Arg Gln Arg Leu Glu Glu Lys Gln Arg
    1130            1135                1140
Ala Glu Glu Glu Arg Leu Lys Gln Glu Arg Glu Leu Met Leu Thr
    1145            1150                1155
Gln Leu Ser Glu Gly Leu Ala Ala Glu Leu Thr Glu Leu Thr Val
    1160            1165                1170
Thr Glu Cys Val Trp Glu Thr Cys Ser Gln Glu Leu Gln Ser Ala
    1175            1180                1185
Val Lys Ile Asp Gln Lys Val Arg Val Ala Arg Cys Cys Glu Ala
    1190            1195                1200
Val Cys Ala His Leu Val Asp Leu Phe Leu Ala Glu Glu Ile Phe
    1205            1210                1215
Gln Thr Ala Lys Glu Thr Leu Gln Glu Leu Gln Cys Phe Cys Lys
    1220            1225                1230
Tyr Leu Gln Arg Trp Arg Glu Ala Val Ala Ala Arg Lys Lys Phe
    1235            1240                1245
Arg Arg Gln Met Arg Ala Phe Pro Ala Ala Pro Cys Cys Val Asp
    1250            1255                1260
Val Asn Asp Arg Leu Gln Ala Leu Val Pro Ser Ala Glu Cys Pro
    1265            1270                1275
Ile Thr Glu Glu Asn Leu Ala Lys Gly Leu Leu Asp Leu Gly His
    1280            1285                1290
Ala Gly Lys Val Gly Val Ser Cys Thr Arg Leu Arg Arg Leu Arg
    1295            1300                1305
Asn Lys Thr Ala His Gln Ile Lys Val Gln His Phe His Gln Gln
    1310            1315                1320
Leu Leu Arg Asn Ala Ala Trp Ala Pro Leu Asp Leu Pro Ser Ile
    1325            1330                1335
Val Ser Glu His Leu Pro Met Lys Gln Lys Arg Arg Phe Trp Lys
    1340            1345                1350
Leu Val Leu Val Leu Pro Asp Val Glu Glu Gln Thr Pro Glu Ser
    1355            1360                1365
Pro Gly Arg Ile Leu Glu Asn Trp Leu Lys Val Lys Phe Thr Gly
    1370            1375                1380
Asp Asp Ser Met Val Gly Asp Ile Gly Asp Asn Ala Gly Asp Ile
    1385            1390                1395
Gln Thr Leu Ser Val Phe Asn Thr Leu Ser Ser Lys Gly Asp Gln
    1400            1405                1410
Thr Val Ser Val Asn Val Cys Ile Lys Val Ala His Gly Thr Leu
    1415            1420                1425
Ser Asp Ser Ala Leu Asp Ala Val Glu Thr Gln Lys Asp Leu Leu
    1430            1435                1440
Gly Thr Ser Gly Leu Met Leu Leu Leu Pro Pro Lys Val Lys Ser
    1445            1450                1455
```

-continued

```
Glu Glu Val Ala Glu Glu Leu Ser Trp Leu Ser Ala Leu Leu
    1460            1465            1470

Gln Leu Lys Gln Leu Leu Gln Ala Lys Pro Phe Gln Pro Ala Leu
    1475            1480            1485

Pro Leu Val Val Leu Val Pro Ser Ser Arg Gly Asp Ser Ala Gly
    1490            1495            1500

Arg Ala Val Glu Asp Gly Leu Met Leu Gln Asp Leu Val Ser Ala
    1505            1510            1515

Lys Leu Ile Ser Asp Tyr Ile Val Val Glu Ile Pro Asp Ser Val
    1520            1525            1530

Asn Asp Leu Gln Gly Thr Val Lys Val Ser Gly Ala Val Gln Trp
    1535            1540            1545

Leu Ile Ser Gly Cys Pro Gln Ala Leu Asp Leu Cys Cys Gln Thr
    1550            1555            1560

Leu Val Gln Tyr Val Glu Asp Gly Ile Ser Arg Glu Phe Ser Arg
    1565            1570            1575

Arg Phe Phe His Asp Arg Arg Glu Arg Arg Leu Ala Ser Leu Pro
    1580            1585            1590

Ser Gln Glu Pro Ser Thr Ile Ile Glu Leu Phe Asn Ser Val Leu
    1595            1600            1605

Gln Phe Leu Ala Ser Val Val Ser Ser Glu Gln Leu Cys Asp Ile
    1610            1615            1620

Ser Trp Pro Val Met Glu Phe Ala Glu Val Gly Gly Ser Gln Leu
    1625            1630            1635

Leu Pro His Leu His Trp Asn Ser Pro Glu His Leu Ala Trp Leu
    1640            1645            1650

Lys Gln Ala Val Leu Gly Phe Gln Leu Pro Gln Met Asp Leu Pro
    1655            1660            1665

Pro Pro Gly Ala Pro Trp Leu Pro Val Cys Ser Met Val Ile Gln
    1670            1675            1680

Tyr Thr Ser Gln Ile Pro Ser Ser Ser Gln Thr Gln Pro Val Leu
    1685            1690            1695

Gln Ser Gln Ala Glu Asn Leu Leu Cys Arg Thr Tyr Gln Lys Trp
    1700            1705            1710

Lys Asn Lys Ser Leu Ser Pro Gly Gln Glu Leu Gly Pro Ser Val
    1715            1720            1725

Ala Glu Ile Pro Trp Asp Asp Ile Ile Thr Leu Cys Ile Asn His
    1730            1735            1740

Lys Leu Arg Asp Trp Thr Pro Pro Arg Leu Pro Val Thr Leu Glu
    1745            1750            1755

Ala Leu Ser Glu Asp Gly Gln Ile Cys Val Tyr Phe Phe Lys Asn
    1760            1765            1770

Leu Leu Arg Lys Tyr His Val Pro Ser Ser Trp Glu Gln Ala Arg
    1775            1780            1785

Met Gln Thr Gln Arg Glu Leu Gln Leu Ser His Gly Arg Ser Gly
    1790            1795            1800

Met Arg Ser Ile His Pro Pro Thr Ser Thr Phe Pro Thr Pro Leu
    1805            1810            1815

Leu His Val His Gln Lys Gly Lys Lys Lys Glu Ser Gly Arg
    1820            1825            1830

Glu Gly Ser Leu Ser Thr Glu Asp Leu Leu Arg Gly Ala Ser Ala
    1835            1840            1845

Glu Glu Leu Leu Ala Gln Ser Leu Ser Ser Ser Leu Leu Glu Glu
```

-continued

```
                  1850                    1855                    1860

Lys Glu  Glu Asn Lys Arg  Phe Glu Asp Gln  Leu Gln Gln Trp Leu
    1865                     1870                     1875

Ser Gln  Asp Ser Gln Ala  Phe Thr Glu Ser  Thr Arg Leu Pro Leu
    1880                     1885                     1890

Tyr Leu  Pro Gln Thr Leu  Val Ser Phe Pro  Asp Ser Ile Lys Thr
    1895                     1900                     1905

Gln Thr  Met Val Lys Thr  Ser Thr Ser Pro  Gln Asn Ser Gly Thr
    1910                     1915                     1920

Gly Lys  Gln Leu Arg Phe  Ser Glu Ala Ser  Gly Ser Ser Leu Thr
    1925                     1930                     1935

Glu Lys  Leu Lys Leu Leu  Glu Arg Leu Ile  Gln Ser Ser Arg Ala
    1940                     1945                     1950

Glu Glu  Ala Ala Ser Glu  Leu His Leu Ser  Ala Leu Leu Glu Met
    1955                     1960                     1965

Val Asp  Met
    1970

<210> SEQ ID NO 3
<211> LENGTH: 6114
<212> TYPE: DNA
<213> ORGANISM: Homo sapiens
<220> FEATURE:
<221> NAME/KEY: CDS
<222> LOCATION: (38)..(5977)

<400> SEQUENCE: 3
gtaatactta attaccttct aataattgga gcagaag atg aac cca act aat cct       55
                                         Met Asn Pro Thr Asn Pro
                                           1               5 ttc agt ggg cag cag cct agt gct ttt tcg gcg tct tct agt aat gta      103
Phe Ser Gly Gln Gln Pro Ser Ala Phe Ser Ala Ser Ser Ser Asn Val
               10                  15                  20 gga aca ctt cca tct aag ccg cca ttt cga ttt ggt caa cct tct ctt      151
Gly Thr Leu Pro Ser Lys Pro Pro Phe Arg Phe Gly Gln Pro Ser Leu
           25                  30                  35 ttt gga caa aac agt acc tta tct ggg aag agc tcg gga ttt tca cag      199
Phe Gly Gln Asn Ser Thr Leu Ser Gly Lys Ser Ser Gly Phe Ser Gln
       40                  45                  50 gta tcc agc ttt cca gcg tct tct gga gta agt cat tcc tct tca gtg      247
Val Ser Ser Phe Pro Ala Ser Ser Gly Val Ser His Ser Ser Ser Val
 55                  60                  65                  70 caa aca tta ggg ttc acc caa acc tca agt gtt gga ccc ttt tct gga      295
Gln Thr Leu Gly Phe Thr Gln Thr Ser Ser Val Gly Pro Phe Ser Gly
                 75                  80                  85 ctt gag cac act tcc acc ttt gtg gct acc tct ggg cct tca agt tca      343
Leu Glu His Thr Ser Thr Phe Val Ala Thr Ser Gly Pro Ser Ser Ser
             90                  95                 100 tct gtg ctg gga aac aca gga ttt agt ttt aaa tca ccc acc agt gtt      391
Ser Val Leu Gly Asn Thr Gly Phe Ser Phe Lys Ser Pro Thr Ser Val
         105                 110                 115 ggg gct ttc cca agc act tct gct ttt gga caa gaa gct gga gaa ata      439
Gly Ala Phe Pro Ser Thr Ser Ala Phe Gly Gln Glu Ala Gly Glu Ile
     120                 125                 130 gtg aac tct ggt ttt ggg aaa aca gaa ttc agc ttt aaa cct ctg gaa      487
Val Asn Ser Gly Phe Gly Lys Thr Glu Phe Ser Phe Lys Pro Leu Glu
135                 140                 145                 150 aat gca gtg ttc aaa cca ata ctg ggg gct gaa tct gag cca gag aaa      535
Asn Ala Val Phe Lys Pro Ile Leu Gly Ala Glu Ser Glu Pro Glu Lys
```

-continued

|  |  |  |  |  |  |  |  |  |  |  |  |  |  |  |  |
|---|---|---|---|---|---|---|---|---|---|---|---|---|---|---|---|
|  |  | 155 |  |  |  | 160 |  |  |  | 165 |  |  |  |  |  |
| acc | agc | agc | caa | att | gct | tct | ggg | ttt | ttt | aca | ttt | tcc | cac | cca | att | 583 |
| Thr | Gln | Ser | Gln | Ile | Ala | Ser | Gly | Phe | Phe | Thr | Phe | Ser | His | Pro | Ile |  |
|  |  | 170 |  |  |  | 175 |  |  |  | 180 |  |  |  |  |  |
| agt | agt | gca | cct | gga | ggc | ctg | gcc | cct | ttc | tct | ttt | cct | caa | gta | aca | 631 |
| Ser | Ser | Ala | Pro | Gly | Gly | Leu | Ala | Pro | Phe | Ser | Phe | Pro | Gln | Val | Thr |  |
|  | 185 |  |  |  |  | 190 |  |  |  | 195 |  |  |  |  |  |
| agt | agt | tca | gct | acc | act | tca | aat | ttt | acc | ttt | tca | aaa | cct | gtt | agt | 679 |
| Ser | Ser | Ser | Ala | Thr | Thr | Ser | Asn | Phe | Thr | Phe | Ser | Lys | Pro | Val | Ser |  |
|  | 200 |  |  |  |  | 205 |  |  |  | 210 |  |  |  |  |  |
| agt | aat | aat | tca | tta | tct | gcc | ttt | acc | cct | gct | ttg | tca | aac | caa | aat | 727 |
| Ser | Asn | Asn | Ser | Leu | Ser | Ala | Phe | Thr | Pro | Ala | Leu | Ser | Asn | Gln | Asn |  |
| 215 |  |  |  |  | 220 |  |  |  | 225 |  |  |  |  | 230 |  |  |
| gta | gag | gaa | gag | aag | aga | gga | cct | aag | tca | ata | ttt | gga | agt | tct | aat | 775 |
| Val | Glu | Glu | Glu | Lys | Arg | Gly | Pro | Lys | Ser | Ile | Phe | Gly | Ser | Ser | Asn |  |
|  |  |  |  | 235 |  |  |  | 240 |  |  |  | 245 |  |  |  |
| aat | agc | ttc | agt | agc | ttc | cct | gta | tca | tct | gcg | gtt | ttg | ggc | gaa | cct | 823 |
| Asn | Ser | Phe | Ser | Ser | Phe | Pro | Val | Ser | Ser | Ala | Val | Leu | Gly | Glu | Pro |  |
|  |  |  | 250 |  |  |  | 255 |  |  |  | 260 |  |  |  |  |
| ttc | cag | gct | agc | aaa | gca | ggt | gtc | agg | cag | ggg | tgt | gaa | gaa | gct | gtt | 871 |
| Phe | Gln | Ala | Ser | Lys | Ala | Gly | Val | Arg | Gln | Gly | Cys | Glu | Glu | Ala | Val |  |
|  |  | 265 |  |  |  | 270 |  |  |  | 275 |  |  |  |  |  |
| tcc | cag | gtg | gaa | cca | ctt | ccc | agc | cta | atg | aaa | gga | ctg | aaa | agg | aag | 919 |
| Ser | Gln | Val | Glu | Pro | Leu | Pro | Ser | Leu | Met | Lys | Gly | Leu | Lys | Arg | Lys |  |
| 280 |  |  |  |  | 285 |  |  |  | 290 |  |  |  |  |  |  |  |
| gag | gac | cag | gat | cgc | tcc | cca | agg | aga | cat | ggc | cac | gag | cca | gca | gaa | 967 |
| Glu | Asp | Gln | Asp | Arg | Ser | Pro | Arg | Arg | His | Gly | His | Glu | Pro | Ala | Glu |  |
| 295 |  |  |  | 300 |  |  |  | 305 |  |  |  |  | 310 |  |  |
| gat | tcg | gat | cct | ctg | tcc | cgg | ggc | gat | cat | cct | cca | gac | aaa | cga | cct | 1015 |
| Asp | Ser | Asp | Pro | Leu | Ser | Arg | Gly | Asp | His | Pro | Pro | Asp | Lys | Arg | Pro |  |
|  |  |  | 315 |  |  |  | 320 |  |  |  | 325 |  |  |  |  |
| gtc | cgc | ctg | aat | cga | ccc | cgg | gga | ggt | act | tta | ttt | ggt | cgg | acg | ata | 1063 |
| Val | Arg | Leu | Asn | Arg | Pro | Arg | Gly | Gly | Thr | Leu | Phe | Gly | Arg | Thr | Ile |  |
|  |  | 330 |  |  |  | 335 |  |  |  | 340 |  |  |  |  |  |
| cag | gat | gtt | ttc | aaa | agc | aat | aag | gaa | gta | ggt | cgt | ctg | ggc | aac | aag | 1111 |
| Gln | Asp | Val | Phe | Lys | Ser | Asn | Lys | Glu | Val | Gly | Arg | Leu | Gly | Asn | Lys |  |
|  | 345 |  |  |  |  | 350 |  |  |  | 355 |  |  |  |  |  |
| gag | gcc | aaa | aag | gaa | act | ggc | ttt | gtt | gag | tct | gca | gaa | agt | gac | cac | 1159 |
| Glu | Ala | Lys | Lys | Glu | Thr | Gly | Phe | Val | Glu | Ser | Ala | Glu | Ser | Asp | His |  |
| 360 |  |  |  |  | 365 |  |  |  | 370 |  |  |  |  |  |  |  |
| atg | gct | atc | cca | gga | ggg | aat | cag | tct | gtc | ctg | gca | cct | tcc | cgg | att | 1207 |
| Met | Ala | Ile | Pro | Gly | Gly | Asn | Gln | Ser | Val | Leu | Ala | Pro | Ser | Arg | Ile |  |
| 375 |  |  |  | 380 |  |  |  | 385 |  |  |  |  | 390 |  |  |
| cca | ggt | gtg | aat | aaa | gag | gaa | gaa | act | gaa | agt | aga | gag | aag | aaa | gaa | 1255 |
| Pro | Gly | Val | Asn | Lys | Glu | Glu | Glu | Thr | Glu | Ser | Arg | Glu | Lys | Lys | Glu |  |
|  |  |  | 395 |  |  |  | 400 |  |  |  | 405 |  |  |  |  |
| gat | tct | cta | aga | gga | act | ccg | gcg | cgt | cag | agt | aac | aga | agc | gag | agc | 1303 |
| Asp | Ser | Leu | Arg | Gly | Thr | Pro | Ala | Arg | Gln | Ser | Asn | Arg | Ser | Glu | Ser |  |
|  |  | 410 |  |  |  | 415 |  |  |  | 420 |  |  |  |  |  |
| aca | gac | agt | ctt | ggg | ggc | ttg | tct | ccc | tct | gaa | gtc | aca | gcc | atc | cag | 1351 |
| Thr | Asp | Ser | Leu | Gly | Gly | Leu | Ser | Pro | Ser | Glu | Val | Thr | Ala | Ile | Gln |  |
|  | 425 |  |  |  |  | 430 |  |  |  | 435 |  |  |  |  |  |
| tgc | aag | aac | atc | cct | gac | tac | ctc | aac | gac | agg | acc | att | ctg | gag | aac | 1399 |
| Cys | Lys | Asn | Ile | Pro | Asp | Tyr | Leu | Asn | Asp | Arg | Thr | Ile | Leu | Glu | Asn |  |
| 440 |  |  |  | 445 |  |  |  | 450 |  |  |  |  |  |  |  |
| cat | ttt | ggc | aaa | att | gct | aaa | gtg | cag | cgc | atc | ttt | acc | agg | cgc | agc | 1447 |
| His | Phe | Gly | Lys | Ile | Ala | Lys | Val | Gln | Arg | Ile | Phe | Thr | Arg | Arg | Ser |  |
| 455 |  |  |  | 460 |  |  |  | 465 |  |  |  | 470 |  |  |  |
| aaa | aag | ctt | gca | gtg | gta | cat | ttc | ttt | gat | cat | gca | tct | gca | gcc | ctg | 1495 |

-continued

```
                Lys Lys Leu Ala Val Val His Phe Phe Asp His Ala Ser Ala Ala Leu
                                475                 480                 485 gct aga aag aag ggg aaa agt ttg cat aaa gac atg gct atc ttt tgg           1543
Ala Arg Lys Lys Gly Lys Ser Leu His Lys Asp Met Ala Ile Phe Trp
            490                 495                 500 cac agg aag aaa ata agc ccc aat aag aaa ccc ttt tcc ctg aag gag           1591
His Arg Lys Lys Ile Ser Pro Asn Lys Lys Pro Phe Ser Leu Lys Glu
        505                 510                 515 aag aaa cca ggt gac ggt gaa gtc agc ccg agc aca gag gat gca ccc           1639
Lys Lys Pro Gly Asp Gly Glu Val Ser Pro Ser Thr Glu Asp Ala Pro
    520                 525                 530 ttt cag cac tct cct ctt ggc aag gcc gca ggg agg act ggt gct agc           1687
Phe Gln His Ser Pro Leu Gly Lys Ala Ala Gly Arg Thr Gly Ala Ser
535                 540                 545                 550 agc ctc ctg aat aaa agc tct cca gtg aag aag cca agt ctt cta aag           1735
Ser Leu Leu Asn Lys Ser Ser Pro Val Lys Lys Pro Ser Leu Leu Lys
                555                 560                 565 gcc cac caa ttc gag gga gac tct ttt gac tca gcc tcc gag ggc tcc           1783
Ala His Gln Phe Glu Gly Asp Ser Phe Asp Ser Ala Ser Glu Gly Ser
            570                 575                 580 gag ggc ctc ggg cca tgt gtg ctc tcc ctc agt acc ctg ata ggc act           1831
Glu Gly Leu Gly Pro Cys Val Leu Ser Leu Ser Thr Leu Ile Gly Thr
        585                 590                 595 gtg gct gag aca tcc aag gag aag tac cgc ctg ctt gac cag aga gac           1879
Val Ala Glu Thr Ser Lys Glu Lys Tyr Arg Leu Leu Asp Gln Arg Asp
    600                 605                 610 agg atc atg cgg caa gct cgg gtg aag aga acc gat ctg gac aaa gcg           1927
Arg Ile Met Arg Gln Ala Arg Val Lys Arg Thr Asp Leu Asp Lys Ala
615                 620                 625                 630 agg act ttt gtt ggc acc tgc ctg gat atg tgt cct gag aag gag agg           1975
Arg Thr Phe Val Gly Thr Cys Leu Asp Met Cys Pro Glu Lys Glu Arg
                635                 640                 645 tac atg cgg gag acc cgt agc cag ctg agc gtg ttc gaa gtg gtc cca           2023
Tyr Met Arg Glu Thr Arg Ser Gln Leu Ser Val Phe Glu Val Val Pro
            650                 655                 660 ggg act gac cag gtg gac cac gca gca gct gtg aaa gag tac agt cgg           2071
Gly Thr Asp Gln Val Asp His Ala Ala Ala Val Lys Glu Tyr Ser Arg
        665                 670                 675 tcc tcg gcg gat cag gag gag ccc ctg ccc cac gag ctg cgg ccc ttg           2119
Ser Ser Ala Asp Gln Glu Glu Pro Leu Pro His Glu Leu Arg Pro Leu
    680                 685                 690 cca gtg ctc agc agg acc atg gac tac ctg gtg acc cag atc atg gac           2167
Pro Val Leu Ser Arg Thr Met Asp Tyr Leu Val Thr Gln Ile Met Asp
695                 700                 705                 710 cag aag gag ggc agc ctg cgg gat tgg tat gac ttc gtg tgg aac cgc           2215
Gln Lys Glu Gly Ser Leu Arg Asp Trp Tyr Asp Phe Val Trp Asn Arg
                715                 720                 725 acg cgt ggc ata cgg aag gat atc acg cag cag cac ctc tgt gac ccc           2263
Thr Arg Gly Ile Arg Lys Asp Ile Thr Gln Gln His Leu Cys Asp Pro
            730                 735                 740 ctg acg gtg tcc ctg att gag aag tgc acc cgg ttt cac atc cac tgt           2311
Leu Thr Val Ser Leu Ile Glu Lys Cys Thr Arg Phe His Ile His Cys
        745                 750                 755 gcc cac ttc atg tgt gag gag ccc atg tcc tcc ttt gat gcc aag atc           2359
Ala His Phe Met Cys Glu Glu Pro Met Ser Ser Phe Asp Ala Lys Ile
    760                 765                 770 aat aat gag aac atg acc aag tgc ctg cag agc ctg aag gag atg tac           2407
Asn Asn Glu Asn Met Thr Lys Cys Leu Gln Ser Leu Lys Glu Met Tyr
775                 780                 785                 790
```

-continued

| | |
|---|---|
| cag gac ctg aga aac aag ggt gtc ttc tgt gcc agc gaa gcg gag ttc<br>Gln Asp Leu Arg Asn Lys Gly Val Phe Cys Ala Ser Glu Ala Glu Phe<br>               795                       800                   805 | 2455 |
| cag ggc tac aat gtt ctg ctc agt ctc aac aag gga gac atc cta aga<br>Gln Gly Tyr Asn Val Leu Leu Ser Leu Asn Lys Gly Asp Ile Leu Arg<br>               810                       815                   820 | 2503 |
| gaa gta caa cag ttc cat cct gct gtt aga aac tca tct gag gtg aaa<br>Glu Val Gln Gln Phe His Pro Ala Val Arg Asn Ser Ser Glu Val Lys<br>               825                       830                   835 | 2551 |
| ttt gct gtt cag gct ttt gct gca ttg aac agt aat aat ttt gtg aga<br>Phe Ala Val Gln Ala Phe Ala Ala Leu Asn Ser Asn Asn Phe Val Arg<br>840                       845                   850 | 2599 |
| ttt ttc aaa ctg gtc cag tca gct tct tac ctg aac gct tgt ctt tta<br>Phe Phe Lys Leu Val Gln Ser Ala Ser Tyr Leu Asn Ala Cys Leu Leu<br>855                       860                   865                   870 | 2647 |
| cac tgt tac ttc agt cag atc cgc aag gat gct ctc cgg gcg ctc aac<br>His Cys Tyr Phe Ser Gln Ile Arg Lys Asp Ala Leu Arg Ala Leu Asn<br>               875                       880                   885 | 2695 |
| ttt gcg tac acg gtg agc aca cag cga tct acc atc ttt ccc ctg gat<br>Phe Ala Tyr Thr Val Ser Thr Gln Arg Ser Thr Ile Phe Pro Leu Asp<br>               890                       895                   900 | 2743 |
| ggt gtg gtg cgc atg ctg ctg ttc aga gac tgt gaa gag gcc acc gac<br>Gly Val Val Arg Met Leu Leu Phe Arg Asp Cys Glu Glu Ala Thr Asp<br>               905                       910                   915 | 2791 |
| ttc ctc acc tgc cac ggc ctc acc gtt tcc gac ggc tgt gtg gag ctg<br>Phe Leu Thr Cys His Gly Leu Thr Val Ser Asp Gly Cys Val Glu Leu<br>920                       925                   930 | 2839 |
| aac cgg tct gca ttc ctg gaa cca gag gga tta tcc aag acc agg aag<br>Asn Arg Ser Ala Phe Leu Glu Pro Glu Gly Leu Ser Lys Thr Arg Lys<br>935                       940                   945                   950 | 2887 |
| tcg gtg ttt att act agg aag ctg acg gtg tca gtc ggg gaa att gtg<br>Ser Val Phe Ile Thr Arg Lys Leu Thr Val Ser Val Gly Glu Ile Val<br>               955                       960                   965 | 2935 |
| aac gga ggg cca ttg ccc ccc gtc cct cgt cac acc cct gtg tgc agc<br>Asn Gly Gly Pro Leu Pro Pro Val Pro Arg His Thr Pro Val Cys Ser<br>               970                       975                   980 | 2983 |
| ttc aac tcc cag aac aag tac atc ggg gag agc ctg gcc gcg gag ctg<br>Phe Asn Ser Gln Asn Lys Tyr Ile Gly Glu Ser Leu Ala Ala Glu Leu<br>               985                       990                   995 | 3031 |
| ccc gtc agc acc cag aga ccc ggc tcc gac aca gtg ggc gga ggg<br>Pro Val Ser Thr Gln Arg Pro Gly Ser Asp Thr Val Gly Gly Gly<br>1000                     1005                    1010 | 3076 |
| aga gga gag gag tgt ggt gta gag ccg gat gca ccc ctg tcc agt<br>Arg Gly Glu Glu Cys Gly Val Glu Pro Asp Ala Pro Leu Ser Ser<br>1015                     1020                    1025 | 3121 |
| ctc cca cag tct cta cca gcc cct gcg ccc tca cca gtg cct ctg<br>Leu Pro Gln Ser Leu Pro Ala Pro Ala Pro Ser Pro Val Pro Leu<br>1030                     1035                    1040 | 3166 |
| cct cct gtc ctg gca ctg acc ccg tct gtg gcg ccc agc ctc ttc<br>Pro Pro Val Leu Ala Leu Thr Pro Ser Val Ala Pro Ser Leu Phe<br>1045                     1050                    1055 | 3211 |
| cag ctg tct gtg cag cct gaa cca ccg cct cca gag ccc gtg ccc<br>Gln Leu Ser Val Gln Pro Glu Pro Pro Pro Pro Glu Pro Val Pro<br>1060                     1065                    1070 | 3256 |
| atg tac tct gac gag gac ctg gcg cag gtg gtg gac gag ctc atc<br>Met Tyr Ser Asp Glu Asp Leu Ala Gln Val Val Asp Glu Leu Ile<br>1075                     1080                    1085 | 3301 |
| cag gag gcc ctg cag agg gac tgt gag gaa gtt ggc tct gcg ggt<br>Gln Glu Ala Leu Gln Arg Asp Cys Glu Glu Val Gly Ser Ala Gly<br>1090                     1095                    1100 | 3346 |

-continued

| | | |
|---|---|---|
| gct gcc tac gca gct gcc gcc ctg ggt gtt tct aat gct gct atg<br>Ala Ala Tyr Ala Ala Ala Ala Leu Gly Val Ser Asn Ala Ala Met<br>1105                           1110                        1115 | 3391 |
| gag gat ttg tta aca gct gca acc acg ggc att ttg agg cac att<br>Glu Asp Leu Leu Thr Ala Ala Thr Thr Gly Ile Leu Arg His Ile<br>1120                           1125                        1130 | 3436 |
| gca gct gaa gaa gtg tct aag gaa aga gag cga agg gag cag gag<br>Ala Ala Glu Glu Val Ser Lys Glu Arg Glu Arg Arg Glu Gln Glu<br>1135                           1140                        1145 | 3481 |
| agg cag cgg gct gaa gag gaa agg ttg aaa caa gag aga gag ctg<br>Arg Gln Arg Ala Glu Glu Glu Arg Leu Lys Gln Glu Arg Glu Leu<br>1150                           1155                        1160 | 3526 |
| gtg tta agt gag ctg agc cag ggc ctg gcc gtg gag ctg atg gaa<br>Val Leu Ser Glu Leu Ser Gln Gly Leu Ala Val Glu Leu Met Glu<br>1165                           1170                        1175 | 3571 |
| cgc gtg atg atg gag ttt gtg agg gaa acc tgc tcc cag gag ttg<br>Arg Val Met Met Glu Phe Val Arg Glu Thr Cys Ser Gln Glu Leu<br>1180                           1185                        1190 | 3616 |
| aag aat gca gta gag aca gac cag agg gtc cgt gtg gcc cgt tgc<br>Lys Asn Ala Val Glu Thr Asp Gln Arg Val Arg Val Ala Arg Cys<br>1195                           1200                        1205 | 3661 |
| tgt gag gat gtc tgt gcc cac tta gtg gac ttg ttt ctc gtg gag<br>Cys Glu Asp Val Cys Ala His Leu Val Asp Leu Phe Leu Val Glu<br>1210                           1215                        1220 | 3706 |
| gaa atc ttc cag act gca aag gag acc ctc cag gag ctt cag tgc<br>Glu Ile Phe Gln Thr Ala Lys Glu Thr Leu Gln Glu Leu Gln Cys<br>1225                           1230                        1235 | 3751 |
| ttc tgc aag tat cta cag cgg tgg agg gaa gct gtc aca gcc cgc<br>Phe Cys Lys Tyr Leu Gln Arg Trp Arg Glu Ala Val Thr Ala Arg<br>1240                           1245                        1250 | 3796 |
| aag aaa ctg agg cgc caa atg cgg gct ttc cct gct gcg ccc tgc<br>Lys Lys Leu Arg Arg Gln Met Arg Ala Phe Pro Ala Ala Pro Cys<br>1255                           1260                        1265 | 3841 |
| tgc gtg gac gtg agc gac cgg ctg agg gcg ctg gcg ccc agc gca<br>Cys Val Asp Val Ser Asp Arg Leu Arg Ala Leu Ala Pro Ser Ala<br>1270                           1275                        1280 | 3886 |
| gag tgc ccc att gct gaa gag aac ctg gcc agg ggc ctc ctg gac<br>Glu Cys Pro Ile Ala Glu Glu Asn Leu Ala Arg Gly Leu Leu Asp<br>1285                           1290                        1295 | 3931 |
| ctg ggc cat gca ggg aga ttg ggc atc tct tgc acc agg tta agg<br>Leu Gly His Ala Gly Arg Leu Gly Ile Ser Cys Thr Arg Leu Arg<br>1300                           1305                        1310 | 3976 |
| cgg ctc aga aac aag aca gct cac cag atg aag gtt cag cac ttc<br>Arg Leu Arg Asn Lys Thr Ala His Gln Met Lys Val Gln His Phe<br>1315                           1320                        1325 | 4021 |
| tac cag cag ctg ctg agt gat gtg gca tgg gcg tct ctg gac ctg<br>Tyr Gln Gln Leu Leu Ser Asp Val Ala Trp Ala Ser Leu Asp Leu<br>1330                           1335                        1340 | 4066 |
| cca tcc ctc gtg gct gag cac ctc cct ggg agg cag gag cat gtg<br>Pro Ser Leu Val Ala Glu His Leu Pro Gly Arg Gln Glu His Val<br>1345                           1350                        1355 | 4111 |
| ttt tgg aag ctg gtg ctg gtg ttg ccg gat gta gag gag cag tcc<br>Phe Trp Lys Leu Val Leu Val Leu Pro Asp Val Glu Glu Gln Ser<br>1360                           1365                        1370 | 4156 |
| cca gag agt tgt ggc aga att cta gca aat tgg tta aaa gtc aag<br>Pro Glu Ser Cys Gly Arg Ile Leu Ala Asn Trp Leu Lys Val Lys<br>1375                           1380                        1385 | 4201 |
| ttc atg gga gat gaa ggc tca gtg gat gac aca tcc agc gat gct<br>Phe Met Gly Asp Glu Gly Ser Val Asp Asp Thr Ser Ser Asp Ala | 4246 |

-continued

| | | | | | | | | | | | | | | |
|---|---|---|---|---|---|---|---|---|---|---|---|---|---|---|
| | | | 1390 | | | | 1395 | | | | 1400 | | | |
| ggt | ggg | att | cag | acg | ctt | tcg | ctt | ttc | aac | tca | ctt | agc | agc | aaa | 4291 |
| Gly | Gly | Ile | Gln | Thr | Leu | Ser | Leu | Phe | Asn | Ser | Leu | Ser | Ser | Lys | |
| | 1405 | | | | 1410 | | | | 1415 | | | | | | |
| ggg | gat | cag | atg | att | tct | gtt | aac | gtg | tgt | ata | aag | gtg | gcc | cat | 4336 |
| Gly | Asp | Gln | Met | Ile | Ser | Val | Asn | Val | Cys | Ile | Lys | Val | Ala | His | |
| | 1420 | | | | 1425 | | | | 1430 | | | | | | |
| ggc | gcc | ctc | agt | gat | ggt | gcc | att | gat | gct | gtg | gag | aca | cag | aag | 4381 |
| Gly | Ala | Leu | Ser | Asp | Gly | Ala | Ile | Asp | Ala | Val | Glu | Thr | Gln | Lys | |
| | 1435 | | | | 1440 | | | | 1445 | | | | | | |
| gac | ctc | ctg | gga | gcc | agt | ggg | ctc | atg | ctg | ctt | ccc | ccc | aaa | | 4426 |
| Asp | Leu | Leu | Gly | Ala | Ser | Gly | Leu | Met | Leu | Leu | Pro | Pro | Lys | | |
| | 1450 | | | | 1455 | | | | 1460 | | | | | | |
| atg | aag | agt | gag | gac | atg | gca | gag | gag | gac | gtg | tac | tgg | ctg | tcg | 4471 |
| Met | Lys | Ser | Glu | Asp | Met | Ala | Glu | Glu | Asp | Val | Tyr | Trp | Leu | Ser | |
| | 1465 | | | | 1470 | | | | 1475 | | | | | | |
| gcc | ttg | ctg | cag | ctc | aag | cag | ctc | ctg | cag | gct | aag | ccc | ttc | cag | 4516 |
| Ala | Leu | Leu | Gln | Leu | Lys | Gln | Leu | Leu | Gln | Ala | Lys | Pro | Phe | Gln | |
| | 1480 | | | | 1485 | | | | 1490 | | | | | | |
| cct | gcg | ctt | cct | ctg | gtg | gtt | ctt | gtg | cct | agc | cca | gga | ggg | gac | 4561 |
| Pro | Ala | Leu | Pro | Leu | Val | Val | Leu | Val | Pro | Ser | Pro | Gly | Gly | Asp | |
| | 1495 | | | | 1500 | | | | 1505 | | | | | | |
| gcc | gtt | gag | aag | gaa | gta | gaa | gat | ggt | ctg | atg | cta | cag | gac | ttg | 4606 |
| Ala | Val | Glu | Lys | Glu | Val | Glu | Asp | Gly | Leu | Met | Leu | Gln | Asp | Leu | |
| | 1510 | | | | 1515 | | | | 1520 | | | | | | |
| gtt | tca | gct | aag | ctg | att | tca | gat | tac | act | gtt | acc | gag | atc | cct | 4651 |
| Val | Ser | Ala | Lys | Leu | Ile | Ser | Asp | Tyr | Thr | Val | Thr | Glu | Ile | Pro | |
| | 1525 | | | | 1530 | | | | 1535 | | | | | | |
| gat | acc | att | aat | gat | cta | caa | ggt | tca | act | aag | gtt | ttg | caa | gca | 4696 |
| Asp | Thr | Ile | Asn | Asp | Leu | Gln | Gly | Ser | Thr | Lys | Val | Leu | Gln | Ala | |
| | 1540 | | | | 1545 | | | | 1550 | | | | | | |
| gtg | cag | tgg | ctg | gtt | tcc | cac | tgc | ccc | cat | tcc | ctt | gac | ctc | tgc | 4741 |
| Val | Gln | Trp | Leu | Val | Ser | His | Cys | Pro | His | Ser | Leu | Asp | Leu | Cys | |
| | 1555 | | | | 1560 | | | | 1565 | | | | | | |
| tgc | cag | act | ctc | att | cag | tac | gtc | gaa | gac | ggg | att | ggc | cat | gag | 4786 |
| Cys | Gln | Thr | Leu | Ile | Gln | Tyr | Val | Glu | Asp | Gly | Ile | Gly | His | Glu | |
| | 1570 | | | | 1575 | | | | 1580 | | | | | | |
| ttt | agt | ggc | cgc | ttt | ttc | cat | gac | aga | aga | gag | agg | cgt | ctg | ggc | 4831 |
| Phe | Ser | Gly | Arg | Phe | Phe | His | Asp | Arg | Arg | Glu | Arg | Arg | Leu | Gly | |
| | 1585 | | | | 1590 | | | | 1595 | | | | | | |
| ggt | ctt | gct | tct | cag | gag | cct | ggc | gcc | atc | att | gag | ctg | ttt | aac | 4876 |
| Gly | Leu | Ala | Ser | Gln | Glu | Pro | Gly | Ala | Ile | Ile | Glu | Leu | Phe | Asn | |
| | 1600 | | | | 1605 | | | | 1610 | | | | | | |
| agt | gtg | ctg | cag | ttc | ctg | gct | tct | gtg | gtg | tcc | tct | gaa | cag | ctg | 4921 |
| Ser | Val | Leu | Gln | Phe | Leu | Ala | Ser | Val | Val | Ser | Ser | Glu | Gln | Leu | |
| | 1615 | | | | 1620 | | | | 1625 | | | | | | |
| tgt | gac | ctg | tcc | tgg | cct | gtc | act | gag | ttt | gct | gag | gca | ggg | ggc | 4966 |
| Cys | Asp | Leu | Ser | Trp | Pro | Val | Thr | Glu | Phe | Ala | Glu | Ala | Gly | Gly | |
| | 1630 | | | | 1635 | | | | 1640 | | | | | | |
| agc | cgg | ctg | ctt | cct | cac | ctg | cac | tgg | aat | gcc | cca | gag | cac | ctg | 5011 |
| Ser | Arg | Leu | Leu | Pro | His | Leu | His | Trp | Asn | Ala | Pro | Glu | His | Leu | |
| | 1645 | | | | 1650 | | | | 1655 | | | | | | |
| gcc | tgg | ctg | aag | cag | gct | gtg | ctc | ggg | ttc | cag | ctt | ccg | cag | atg | 5056 |
| Ala | Trp | Leu | Lys | Gln | Ala | Val | Leu | Gly | Phe | Gln | Leu | Pro | Gln | Met | |
| | 1660 | | | | 1665 | | | | 1670 | | | | | | |
| gac | ctt | cca | ccc | ctg | ggg | gcc | ccc | tgg | ctc | ccc | gtg | tgc | tcc | atg | 5101 |
| Asp | Leu | Pro | Pro | Leu | Gly | Ala | Pro | Trp | Leu | Pro | Val | Cys | Ser | Met | |
| | 1675 | | | | 1680 | | | | 1685 | | | | | | |
| gtt | gtc | cag | tac | gcc | tcc | cag | atc | ccc | agc | tca | cgc | cag | aca | cag | 5146 |

```
                Val Val Gln Tyr Ala Ser Gln Ile Pro Ser Ser Arg Gln Thr Gln
                    1690                1695                1700 cct gtc ctc cag tcc cag gtg gag aac ctg ctc cac aga acc tac          5191
Pro Val Leu Gln Ser Gln Val Glu Asn Leu Leu His Arg Thr Tyr
    1705                1710                1715 tgt agg tgg aag agc aag agt ccc tcc cca gtc cat ggg gca ggc          5236
Cys Arg Trp Lys Ser Lys Ser Pro Ser Pro Val His Gly Ala Gly
    1720                1725                1730 ccc tcg gtc atg gag atc cca tgg gat gat ctt atc gcc ttg tgt          5281
Pro Ser Val Met Glu Ile Pro Trp Asp Asp Leu Ile Ala Leu Cys
    1735                1740                1745 atc aac cac aag ctg aga gac tgg acg ccc ccc cgg ctt cct gtt          5326
Ile Asn His Lys Leu Arg Asp Trp Thr Pro Pro Arg Leu Pro Val
    1750                1755                1760 aca tca gag gcg ctg agt gaa gat ggt cag ata tgt gtg tat ttt          5371
Thr Ser Glu Ala Leu Ser Glu Asp Gly Gln Ile Cys Val Tyr Phe
    1765                1770                1775 ttt aaa aac gat ttg aaa aaa tat gat gtt cct ttg tcg tgg gaa          5416
Phe Lys Asn Asp Leu Lys Lys Tyr Asp Val Pro Leu Ser Trp Glu
    1780                1785                1790 caa gcc agg ttg cag acg cag aag gag cta cag ctg aga gag gga          5461
Gln Ala Arg Leu Gln Thr Gln Lys Glu Leu Gln Leu Arg Glu Gly
    1795                1800                1805 cgt ttg gca ata aag cct ttt cat cct tct gca aac aat ttt ccc          5506
Arg Leu Ala Ile Lys Pro Phe His Pro Ser Ala Asn Asn Phe Pro
    1810                1815                1820 ata cca ttg ctt cac atg cac cgt aac tgg aag agg agc aca gag          5551
Ile Pro Leu Leu His Met His Arg Asn Trp Lys Arg Ser Thr Glu
    1825                1830                1835 tgt gct caa gag ggg agg att ccc agc aca gag gat ctg atg cga          5596
Cys Ala Gln Glu Gly Arg Ile Pro Ser Thr Glu Asp Leu Met Arg
    1840                1845                1850 gga gct tct gct gag gag ctc ttg gcg cag tgt ttg tcg agc agt          5641
Gly Ala Ser Ala Glu Glu Leu Leu Ala Gln Cys Leu Ser Ser Ser
    1855                1860                1865 ctg ctg ctg gag aaa gaa gag aac aag agg ttt gaa gat cag ctt          5686
Leu Leu Leu Glu Lys Glu Glu Asn Lys Arg Phe Glu Asp Gln Leu
    1870                1875                1880 cag caa tgg ttg tct gaa gac tca gga gca ttt acg gat tta act          5731
Gln Gln Trp Leu Ser Glu Asp Ser Gly Ala Phe Thr Asp Leu Thr
    1885                1890                1895 tcc ctt ccc ctc tat ctt cct cag act cta gtg tct ctt tct cac          5776
Ser Leu Pro Leu Tyr Leu Pro Gln Thr Leu Val Ser Leu Ser His
    1900                1905                1910 act att gaa cct gtg atg aaa aca tct gta act act agc cca cag          5821
Thr Ile Glu Pro Val Met Lys Thr Ser Val Thr Thr Ser Pro Gln
    1915                1920                1925 agt gac atg atg agg gag caa ctg cag ctg tca gag gcg aca gga          5866
Ser Asp Met Met Arg Glu Gln Leu Gln Leu Ser Glu Ala Thr Gly
    1930                1935                1940 acg tgt cta ggc gaa cga cta aag cac ctg gaa agg ctg atc cgg          5911
Thr Cys Leu Gly Glu Arg Leu Lys His Leu Glu Arg Leu Ile Arg
    1945                1950                1955 agt tca agg gaa gag gaa gtt gcc tct gag ctc cat ctc tct gcg          5956
Ser Ser Arg Glu Glu Glu Val Ala Ser Glu Leu His Leu Ser Ala
    1960                1965                1970 ctg cta gac atg gtg gac att tgagcagcct gacctgtggg gagggggtct        6007
Leu Leu Asp Met Val Asp Ile
    1975                1980
```

```
ctcccgaaga gtttctgttt ttactcaaaa taatgttatt ctcagatgct tgatgcactg    6067
ttggaaatgt gattaattta atcatgcaga taaaccattt aaatgtc                 6114
```

<210> SEQ ID NO 4
<211> LENGTH: 1980
<212> TYPE: PRT
<213> ORGANISM: Homo sapiens

<400> SEQUENCE: 4

```
Met Asn Pro Thr Asn Pro Phe Ser Gly Gln Gln Pro Ser Ala Phe Ser
1               5                   10                  15

Ala Ser Ser Ser Asn Val Gly Thr Leu Pro Ser Lys Pro Pro Phe Arg
            20                  25                  30

Phe Gly Gln Pro Ser Leu Phe Gly Gln Asn Ser Thr Leu Ser Gly Lys
        35                  40                  45

Ser Ser Gly Phe Ser Gln Val Ser Ser Phe Pro Ala Ser Ser Gly Val
    50                  55                  60

Ser His Ser Ser Ser Val Gln Thr Leu Gly Phe Thr Gln Thr Ser Ser
65                  70                  75                  80

Val Gly Pro Phe Ser Gly Leu Glu His Thr Ser Thr Phe Val Ala Thr
                85                  90                  95

Ser Gly Pro Ser Ser Ser Ser Val Leu Gly Asn Thr Gly Phe Ser Phe
            100                 105                 110

Lys Ser Pro Thr Ser Val Gly Ala Phe Pro Ser Thr Ser Ala Phe Gly
        115                 120                 125

Gln Glu Ala Gly Glu Ile Val Asn Ser Gly Phe Gly Lys Thr Glu Phe
    130                 135                 140

Ser Phe Lys Pro Leu Glu Asn Ala Val Phe Lys Pro Ile Leu Gly Ala
145                 150                 155                 160

Glu Ser Glu Pro Glu Lys Thr Gln Ser Gln Ile Ala Ser Gly Phe Phe
                165                 170                 175

Thr Phe Ser His Pro Ile Ser Ser Ala Pro Gly Gly Leu Ala Pro Phe
            180                 185                 190

Ser Phe Pro Gln Val Thr Ser Ser Ala Thr Thr Ser Asn Phe Thr
        195                 200                 205

Phe Ser Lys Pro Val Ser Ser Asn Asn Ser Leu Ser Ala Phe Thr Pro
210                 215                 220

Ala Leu Ser Asn Gln Asn Val Glu Glu Glu Lys Arg Gly Pro Lys Ser
225                 230                 235                 240

Ile Phe Gly Ser Ser Asn Asn Ser Phe Ser Phe Pro Val Ser Ser
                245                 250                 255

Ala Val Leu Gly Glu Pro Phe Gln Ala Ser Lys Ala Gly Val Arg Gln
            260                 265                 270

Gly Cys Glu Glu Ala Val Ser Gln Val Glu Pro Leu Pro Ser Leu Met
        275                 280                 285

Lys Gly Leu Lys Arg Lys Glu Asp Gln Asp Arg Ser Pro Arg Arg His
    290                 295                 300

Gly His Glu Pro Ala Glu Asp Ser Asp Pro Leu Ser Arg Gly Asp His
305                 310                 315                 320

Pro Pro Asp Lys Arg Pro Val Arg Leu Asn Arg Pro Gly Gly Thr
                325                 330                 335

Leu Phe Gly Arg Thr Ile Gln Asp Val Phe Lys Ser Asn Lys Glu Val
            340                 345                 350

Gly Arg Leu Gly Asn Lys Glu Ala Lys Lys Glu Thr Gly Phe Val Glu
```

-continued

```
                355                 360                 365
Ser Ala Glu Ser Asp His Met Ala Ile Pro Gly Gly Asn Gln Ser Val
370                 375                 380

Leu Ala Pro Ser Arg Ile Pro Gly Val Asn Lys Glu Glu Thr Glu
385                 390                 395                 400

Ser Arg Glu Lys Lys Glu Asp Ser Leu Arg Gly Thr Pro Ala Arg Gln
                405                 410                 415

Ser Asn Arg Ser Glu Ser Thr Asp Ser Leu Gly Gly Leu Ser Pro Ser
                420                 425                 430

Glu Val Thr Ala Ile Gln Cys Lys Asn Ile Pro Asp Tyr Leu Asn Asp
                435                 440                 445

Arg Thr Ile Leu Glu Asn His Phe Gly Lys Ile Ala Lys Val Gln Arg
450                 455                 460

Ile Phe Thr Arg Arg Ser Lys Lys Leu Ala Val Val His Phe Phe Asp
465                 470                 475                 480

His Ala Ser Ala Ala Leu Ala Arg Lys Lys Gly Lys Ser Leu His Lys
                485                 490                 495

Asp Met Ala Ile Phe Trp His Arg Lys Lys Ile Ser Pro Asn Lys Lys
                500                 505                 510

Pro Phe Ser Leu Lys Glu Lys Lys Pro Gly Asp Gly Glu Val Ser Pro
                515                 520                 525

Ser Thr Glu Asp Ala Pro Phe Gln His Ser Pro Leu Gly Lys Ala Ala
530                 535                 540

Gly Arg Thr Gly Ala Ser Ser Leu Leu Asn Lys Ser Ser Pro Val Lys
545                 550                 555                 560

Lys Pro Ser Leu Leu Lys Ala His Gln Phe Glu Gly Asp Ser Phe Asp
                565                 570                 575

Ser Ala Ser Glu Gly Ser Glu Gly Leu Gly Pro Cys Val Leu Ser Leu
                580                 585                 590

Ser Thr Leu Ile Gly Thr Val Ala Glu Thr Ser Lys Glu Lys Tyr Arg
                595                 600                 605

Leu Leu Asp Gln Arg Asp Arg Ile Met Arg Gln Ala Arg Val Lys Arg
                610                 615                 620

Thr Asp Leu Asp Lys Ala Arg Thr Phe Val Gly Thr Cys Leu Asp Met
625                 630                 635                 640

Cys Pro Glu Lys Glu Arg Tyr Met Arg Glu Thr Arg Ser Gln Leu Ser
                645                 650                 655

Val Phe Glu Val Val Pro Gly Thr Asp Gln Val Asp His Ala Ala Ala
                660                 665                 670

Val Lys Glu Tyr Ser Arg Ser Ser Ala Asp Gln Glu Glu Pro Leu Pro
                675                 680                 685

His Glu Leu Arg Pro Leu Pro Val Leu Ser Arg Thr Met Asp Tyr Leu
690                 695                 700

Val Thr Gln Ile Met Asp Gln Lys Glu Gly Ser Leu Arg Asp Trp Tyr
705                 710                 715                 720

Asp Phe Val Trp Asn Arg Thr Arg Gly Ile Arg Lys Asp Ile Thr Gln
                725                 730                 735

Gln His Leu Cys Asp Pro Leu Thr Val Ser Leu Ile Glu Lys Cys Thr
                740                 745                 750

Arg Phe His Ile His Cys Ala His Phe Met Cys Glu Glu Pro Met Ser
                755                 760                 765

Ser Phe Asp Ala Lys Ile Asn Asn Glu Asn Met Thr Lys Cys Leu Gln
770                 775                 780
```

-continued

```
Ser Leu Lys Glu Met Tyr Gln Asp Leu Arg Asn Lys Gly Val Phe Cys
785                 790                 795                 800

Ala Ser Glu Ala Glu Phe Gln Gly Tyr Asn Val Leu Ser Leu Asn
            805                 810                 815

Lys Gly Asp Ile Leu Arg Glu Val Gln Gln Phe His Pro Ala Val Arg
                820                 825                 830

Asn Ser Ser Glu Val Lys Phe Ala Val Gln Ala Phe Ala Ala Leu Asn
                835                 840                 845

Ser Asn Asn Phe Val Arg Phe Phe Lys Leu Val Gln Ser Ala Ser Tyr
850                 855                 860

Leu Asn Ala Cys Leu Leu His Cys Tyr Phe Ser Gln Ile Arg Lys Asp
865                 870                 875                 880

Ala Leu Arg Ala Leu Asn Phe Ala Tyr Thr Val Ser Thr Gln Arg Ser
                885                 890                 895

Thr Ile Phe Pro Leu Asp Gly Val Val Arg Met Leu Leu Phe Arg Asp
                900                 905                 910

Cys Glu Glu Ala Thr Asp Phe Leu Thr Cys His Gly Leu Thr Val Ser
            915                 920                 925

Asp Gly Cys Val Glu Leu Asn Arg Ser Ala Phe Leu Glu Pro Glu Gly
            930                 935                 940

Leu Ser Lys Thr Arg Lys Ser Val Phe Ile Thr Arg Lys Leu Thr Val
945                 950                 955                 960

Ser Val Gly Glu Ile Val Asn Gly Gly Pro Leu Pro Pro Val Pro Arg
                965                 970                 975

His Thr Pro Val Cys Ser Phe Asn Ser Gln Asn Lys Tyr Ile Gly Glu
                980                 985                 990

Ser Leu Ala Ala Glu Leu Pro Val Ser Thr Gln Arg Pro Gly Ser Asp
                995                 1000                1005

Thr Val Gly Gly Gly Arg Gly Glu Glu Cys Gly Val Glu Pro Asp
    1010                1015                1020

Ala Pro Leu Ser Ser Leu Pro Gln Ser Leu Pro Ala Pro Ala Pro
    1025                1030                1035

Ser Pro Val Pro Leu Pro Pro Val Leu Ala Leu Thr Pro Ser Val
    1040                1045                1050

Ala Pro Ser Leu Phe Gln Leu Ser Val Gln Pro Glu Pro Pro Pro
    1055                1060                1065

Pro Glu Pro Val Pro Met Tyr Ser Asp Glu Asp Leu Ala Gln Val
    1070                1075                1080

Val Asp Glu Leu Ile Gln Glu Ala Leu Gln Arg Asp Cys Glu Glu
    1085                1090                1095

Val Gly Ser Ala Gly Ala Ala Tyr Ala Ala Ala Leu Gly Val
    1100                1105                1110

Ser Asn Ala Ala Met Glu Asp Leu Leu Thr Ala Ala Thr Thr Gly
    1115                1120                1125

Ile Leu Arg His Ile Ala Ala Glu Glu Val Ser Lys Glu Arg Glu
    1130                1135                1140

Arg Arg Glu Gln Glu Arg Gln Arg Ala Glu Glu Glu Arg Leu Lys
    1145                1150                1155

Gln Glu Arg Glu Leu Val Leu Ser Glu Leu Ser Gln Gly Leu Ala
    1160                1165                1170

Val Glu Leu Met Glu Arg Val Met Met Glu Phe Val Arg Glu Thr
    1175                1180                1185
```

-continued

```
Cys Ser Gln Glu Leu Lys Asn Ala Val Glu Thr Asp Gln Arg Val
    1190            1195                1200

Arg Val Ala Arg Cys Cys Glu Asp Val Cys Ala His Leu Val Asp
    1205            1210                1215

Leu Phe Leu Val Glu Glu Ile Phe Gln Thr Ala Lys Glu Thr Leu
    1220            1225                1230

Gln Glu Leu Gln Cys Phe Cys Lys Tyr Leu Gln Arg Trp Arg Glu
    1235            1240                1245

Ala Val Thr Ala Arg Lys Lys Leu Arg Arg Gln Met Arg Ala Phe
    1250            1255                1260

Pro Ala Ala Pro Cys Cys Val Asp Val Ser Asp Arg Leu Arg Ala
    1265            1270                1275

Leu Ala Pro Ser Ala Glu Cys Pro Ile Ala Glu Glu Asn Leu Ala
    1280            1285                1290

Arg Gly Leu Leu Asp Leu Gly His Ala Gly Arg Leu Gly Ile Ser
    1295            1300                1305

Cys Thr Arg Leu Arg Arg Leu Arg Asn Lys Thr Ala His Gln Met
    1310            1315                1320

Lys Val Gln His Phe Tyr Gln Leu Leu Ser Asp Val Ala Trp
    1325            1330                1335

Ala Ser Leu Asp Leu Pro Ser Leu Val Ala Glu His Leu Pro Gly
    1340            1345                1350

Arg Gln Glu His Val Phe Trp Lys Leu Val Leu Val Leu Pro Asp
    1355            1360                1365

Val Glu Glu Gln Ser Pro Glu Ser Cys Gly Arg Ile Leu Ala Asn
    1370            1375                1380

Trp Leu Lys Val Lys Phe Met Gly Asp Glu Gly Ser Val Asp Asp
    1385            1390                1395

Thr Ser Ser Asp Ala Gly Gly Ile Gln Thr Leu Ser Leu Phe Asn
    1400            1405                1410

Ser Leu Ser Ser Lys Gly Asp Gln Met Ile Ser Val Asn Val Cys
    1415            1420                1425

Ile Lys Val Ala His Gly Ala Leu Ser Asp Gly Ala Ile Asp Ala
    1430            1435                1440

Val Glu Thr Gln Lys Asp Leu Leu Gly Ala Ser Gly Leu Met Leu
    1445            1450                1455

Leu Leu Pro Pro Lys Met Lys Ser Glu Asp Met Ala Glu Glu Asp
    1460            1465                1470

Val Tyr Trp Leu Ser Ala Leu Leu Gln Leu Lys Gln Leu Leu Gln
    1475            1480                1485

Ala Lys Pro Phe Gln Pro Ala Leu Pro Leu Val Val Leu Val Pro
    1490            1495                1500

Ser Pro Gly Gly Asp Ala Val Glu Lys Glu Val Glu Asp Gly Leu
    1505            1510                1515

Met Leu Gln Asp Leu Val Ser Ala Lys Leu Ile Ser Asp Tyr Thr
    1520            1525                1530

Val Thr Glu Ile Pro Asp Thr Ile Asn Asp Leu Gln Gly Ser Thr
    1535            1540                1545

Lys Val Leu Gln Ala Val Gln Trp Leu Val Ser His Cys Pro His
    1550            1555                1560

Ser Leu Asp Leu Cys Cys Gln Thr Leu Ile Gln Tyr Val Glu Asp
    1565            1570                1575

Gly Ile Gly His Glu Phe Ser Gly Arg Phe Phe His Asp Arg Arg
```

```
                1580                  1585                  1590

Glu Arg Arg Leu Gly Gly Leu Ala Ser Gln Glu Pro Gly Ala Ile
    1595                  1600                  1605

Ile Glu Leu Phe Asn Ser Val Leu Gln Phe Leu Ala Ser Val Val
    1610                  1615                  1620

Ser Ser Glu Gln Leu Cys Asp Leu Ser Trp Pro Val Thr Glu Phe
    1625                  1630                  1635

Ala Glu Ala Gly Gly Ser Arg Leu Leu Pro His Leu His Trp Asn
    1640                  1645                  1650

Ala Pro Glu His Leu Ala Trp Leu Lys Gln Ala Val Leu Gly Phe
    1655                  1660                  1665

Gln Leu Pro Gln Met Asp Leu Pro Pro Leu Gly Ala Pro Trp Leu
    1670                  1675                  1680

Pro Val Cys Ser Met Val Val Gln Tyr Ala Ser Gln Ile Pro Ser
    1685                  1690                  1695

Ser Arg Gln Thr Gln Pro Val Leu Gln Ser Gln Val Glu Asn Leu
    1700                  1705                  1710

Leu His Arg Thr Tyr Cys Arg Trp Lys Ser Lys Ser Pro Ser Pro
    1715                  1720                  1725

Val His Gly Ala Gly Pro Ser Val Met Glu Ile Pro Trp Asp Asp
    1730                  1735                  1740

Leu Ile Ala Leu Cys Ile Asn His Lys Leu Arg Asp Trp Thr Pro
    1745                  1750                  1755

Pro Arg Leu Pro Val Thr Ser Glu Ala Leu Ser Glu Asp Gly Gln
    1760                  1765                  1770

Ile Cys Val Tyr Phe Phe Lys Asn Asp Leu Lys Lys Tyr Asp Val
    1775                  1780                  1785

Pro Leu Ser Trp Glu Gln Ala Arg Leu Gln Thr Gln Lys Glu Leu
    1790                  1795                  1800

Gln Leu Arg Glu Gly Arg Leu Ala Ile Lys Pro Phe His Pro Ser
    1805                  1810                  1815

Ala Asn Asn Phe Pro Ile Pro Leu Leu His Met His Arg Asn Trp
    1820                  1825                  1830

Lys Arg Ser Thr Glu Cys Ala Gln Glu Gly Arg Ile Pro Ser Thr
    1835                  1840                  1845

Glu Asp Leu Met Arg Gly Ala Ser Ala Glu Glu Leu Leu Ala Gln
    1850                  1855                  1860

Cys Leu Ser Ser Ser Leu Leu Leu Glu Lys Glu Glu Asn Lys Arg
    1865                  1870                  1875

Phe Glu Asp Gln Leu Gln Gln Trp Leu Ser Glu Asp Ser Gly Ala
    1880                  1885                  1890

Phe Thr Asp Leu Thr Ser Leu Pro Leu Tyr Leu Pro Gln Thr Leu
    1895                  1900                  1905

Val Ser Leu Ser His Thr Ile Glu Pro Val Met Lys Thr Ser Val
    1910                  1915                  1920

Thr Thr Ser Pro Gln Ser Asp Met Met Arg Glu Gln Leu Gln Leu
    1925                  1930                  1935

Ser Glu Ala Thr Gly Thr Cys Leu Gly Glu Arg Leu Lys His Leu
    1940                  1945                  1950

Glu Arg Leu Ile Arg Ser Ser Arg Glu Glu Val Ala Ser Glu
    1955                  1960                  1965

Leu His Leu Ser Ala Leu Leu Asp Met Val Asp Ile
    1970                  1975                  1980
```

<210> SEQ ID NO 5
<211> LENGTH: 863
<212> TYPE: PRT
<213> ORGANISM: retroviral provirus

<400> SEQUENCE: 5

| | | | | | | | | | | | | | | |
|---|---|---|---|---|---|---|---|---|---|---|---|---|---|---|
| Lys | Glu | Gln | Lys | Thr | Val | Ala | Met | Arg | Val | Lys | Glu | Lys | Tyr | Gln | His |
| 1 | | | | 5 | | | | | 10 | | | | | 15 | |

| Leu | Trp | Arg | Trp | Gly | Trp | Arg | Trp | Gly | Thr | Met | Leu | Leu | Gly | Met | Leu |
|---|---|---|---|---|---|---|---|---|---|---|---|---|---|---|---|
| | | | 20 | | | | | 25 | | | | | 30 | | |

| Met | Ile | Cys | Ser | Ala | Thr | Glu | Lys | Leu | Trp | Val | Thr | Val | Tyr | Tyr | Gly |
|---|---|---|---|---|---|---|---|---|---|---|---|---|---|---|---|
| | | 35 | | | | | 40 | | | | | 45 | | | |

| Val | Pro | Val | Trp | Lys | Glu | Ala | Thr | Thr | Thr | Leu | Phe | Cys | Ala | Ser | Asp |
|---|---|---|---|---|---|---|---|---|---|---|---|---|---|---|---|
| | 50 | | | | | 55 | | | | | 60 | | | | |

| Ala | Lys | Ala | Tyr | Asp | Thr | Glu | Val | His | Asn | Val | Trp | Ala | Thr | His | Ala |
|---|---|---|---|---|---|---|---|---|---|---|---|---|---|---|---|
| 65 | | | | | 70 | | | | | 75 | | | | | 80 |

| Cys | Val | Pro | Thr | Asp | Pro | Asn | Pro | Gln | Glu | Val | Val | Leu | Val | Asn | Val |
|---|---|---|---|---|---|---|---|---|---|---|---|---|---|---|---|
| | | | | 85 | | | | | 90 | | | | | 95 | |

| Thr | Glu | Asn | Phe | Asn | Met | Trp | Lys | Asn | Asp | Met | Val | Glu | Gln | Met | His |
|---|---|---|---|---|---|---|---|---|---|---|---|---|---|---|---|
| | | | 100 | | | | | 105 | | | | | 110 | | |

| Glu | Asp | Ile | Ile | Ser | Leu | Trp | Asp | Gln | Ser | Leu | Lys | Pro | Cys | Val | Lys |
|---|---|---|---|---|---|---|---|---|---|---|---|---|---|---|---|
| | | 115 | | | | | 120 | | | | | 125 | | | |

| Leu | Thr | Pro | Leu | Cys | Val | Ser | Leu | Lys | Cys | Thr | Asp | Leu | Lys | Asn | Asp |
|---|---|---|---|---|---|---|---|---|---|---|---|---|---|---|---|
| | 130 | | | | | 135 | | | | | 140 | | | | |

| Thr | Asn | Thr | Asn | Ser | Ser | Ser | Gly | Arg | Met | Ile | Met | Glu | Lys | Gly | Glu |
|---|---|---|---|---|---|---|---|---|---|---|---|---|---|---|---|
| 145 | | | | | 150 | | | | | 155 | | | | | 160 |

| Ile | Lys | Asn | Cys | Ser | Phe | Asn | Ile | Ser | Thr | Ser | Ile | Arg | Gly | Lys | Val |
|---|---|---|---|---|---|---|---|---|---|---|---|---|---|---|---|
| | | | | 165 | | | | | 170 | | | | | 175 | |

| Gln | Lys | Glu | Tyr | Ala | Phe | Phe | Tyr | Lys | Leu | Asp | Ile | Ile | Pro | Ile | Asp |
|---|---|---|---|---|---|---|---|---|---|---|---|---|---|---|---|
| | | | 180 | | | | | 185 | | | | | 190 | | |

| Asn | Asp | Thr | Thr | Ser | Tyr | Thr | Leu | Thr | Ser | Cys | Asn | Thr | Ser | Val | Ile |
|---|---|---|---|---|---|---|---|---|---|---|---|---|---|---|---|
| | | 195 | | | | | 200 | | | | | 205 | | | |

| Thr | Gln | Ala | Cys | Pro | Lys | Val | Ser | Phe | Glu | Pro | Ile | Pro | Ile | His | Tyr |
|---|---|---|---|---|---|---|---|---|---|---|---|---|---|---|---|
| | 210 | | | | | 215 | | | | | 220 | | | | |

| Cys | Ala | Pro | Ala | Gly | Phe | Ala | Ile | Leu | Lys | Cys | Asn | Asn | Lys | Thr | Phe |
|---|---|---|---|---|---|---|---|---|---|---|---|---|---|---|---|
| 225 | | | | | 230 | | | | | 235 | | | | | 240 |

| Asn | Gly | Thr | Gly | Pro | Cys | Thr | Asn | Val | Ser | Thr | Val | Gln | Cys | Thr | His |
|---|---|---|---|---|---|---|---|---|---|---|---|---|---|---|---|
| | | | | 245 | | | | | 250 | | | | | 255 | |

| Gly | Ile | Arg | Pro | Val | Val | Ser | Thr | Gln | Leu | Leu | Leu | Asn | Gly | Ser | Leu |
|---|---|---|---|---|---|---|---|---|---|---|---|---|---|---|---|
| | | | 260 | | | | | 265 | | | | | 270 | | |

| Ala | Glu | Glu | Glu | Val | Val | Ile | Arg | Ser | Ala | Asn | Phe | Thr | Asp | Asn | Ala |
|---|---|---|---|---|---|---|---|---|---|---|---|---|---|---|---|
| | | 275 | | | | | 280 | | | | | 285 | | | |

| Lys | Thr | Ile | Ile | Val | Gln | Leu | Asn | Gln | Ser | Val | Glu | Ile | Asn | Cys | Thr |
|---|---|---|---|---|---|---|---|---|---|---|---|---|---|---|---|
| | 290 | | | | | 295 | | | | | 300 | | | | |

| Arg | Pro | Asn | Asn | Asn | Thr | Arg | Lys | Ser | Ile | Arg | Ile | Gln | Arg | Gly | Pro |
|---|---|---|---|---|---|---|---|---|---|---|---|---|---|---|---|
| 305 | | | | | 310 | | | | | 315 | | | | | 320 |

| Gly | Arg | Ala | Phe | Val | Thr | Ile | Gly | Lys | Ile | Gly | Asn | Met | Arg | Gln | Ala |
|---|---|---|---|---|---|---|---|---|---|---|---|---|---|---|---|
| | | | | 325 | | | | | 330 | | | | | 335 | |

| His | Cys | Asn | Ile | Ser | Arg | Ala | Lys | Trp | Asn | Asn | Thr | Leu | Lys | Gln | Ile |
|---|---|---|---|---|---|---|---|---|---|---|---|---|---|---|---|
| | | | 340 | | | | | 345 | | | | | 350 | | |

| Asp | Ser | Lys | Leu | Arg | Glu | Gln | Phe | Gly | Asn | Asn | Lys | Thr | Ile | Ile | Phe |
|---|---|---|---|---|---|---|---|---|---|---|---|---|---|---|---|
| | | 355 | | | | | 360 | | | | | 365 | | | |

| Lys | Gln | Ser | Ser | Gly | Gly | Asp | Pro | Glu | Ile | Val | Thr | His | Ser | Phe | Asn |
|---|---|---|---|---|---|---|---|---|---|---|---|---|---|---|---|

-continued

```
            370                 375                 380
Cys Gly Gly Glu Phe Phe Tyr Cys Asn Ser Thr Gln Leu Phe Asn Ser
385                 390                 395                 400

Thr Trp Phe Asn Ser Thr Trp Ser Thr Lys Gly Ser Asn Asn Thr Glu
                405                 410                 415

Gly Ser Asp Thr Ile Thr Leu Pro Cys Arg Ile Lys Gln Ile Ile Asn
                420                 425                 430

Met Trp Gln Glu Val Gly Lys Ala Met Tyr Ala Pro Pro Ile Ser Gly
            435                 440                 445

Gln Ile Arg Cys Ser Ser Asn Ile Thr Gly Leu Leu Leu Thr Arg Asp
450                 455                 460

Gly Gly Asn Ser Asn Asn Glu Ser Glu Ile Phe Arg Pro Gly Gly Gly
465                 470                 475                 480

Asp Met Arg Asp Asn Trp Arg Ser Glu Leu Tyr Lys Tyr Lys Val Val
                485                 490                 495

Lys Ile Glu Pro Leu Gly Val Ala Pro Thr Lys Ala Lys Arg Arg Val
                500                 505                 510

Val Gln Arg Glu Lys Arg Ala Val Gly Ile Gly Ala Leu Phe Leu Gly
            515                 520                 525

Phe Leu Gly Ala Ala Gly Ser Thr Met Gly Ala Ala Ser Met Thr Leu
530                 535                 540

Thr Val Gln Ala Arg Gln Leu Leu Ser Gly Ile Val Gln Gln Gln Asn
545                 550                 555                 560

Asn Leu Leu Arg Ala Ile Glu Ala Gln Gln His Leu Leu Gln Leu Thr
                565                 570                 575

Val Trp Gly Ile Lys Gln Leu Gln Ala Arg Ile Leu Ala Val Glu Arg
            580                 585                 590

Tyr Leu Lys Asp Gln Gln Leu Leu Gly Ile Trp Gly Cys Ser Gly Lys
            595                 600                 605

Leu Ile Cys Thr Thr Ala Val Pro Trp Asn Ala Ser Trp Ser Asn Lys
            610                 615                 620

Ser Leu Glu Gln Ile Trp Asn Asn Met Thr Trp Met Glu Trp Asp Arg
625                 630                 635                 640

Glu Ile Asn Asn Tyr Thr Ser Leu Ile His Ser Leu Ile Glu Glu Ser
                645                 650                 655

Gln Asn Gln Gln Glu Lys Asn Glu Gln Glu Leu Leu Glu Leu Asp Lys
                660                 665                 670

Trp Ala Ser Leu Trp Asn Trp Phe Asn Ile Thr Asn Trp Leu Trp Tyr
            675                 680                 685

Ile Lys Leu Phe Ile Met Ile Val Gly Gly Leu Val Gly Leu Arg Ile
            690                 695                 700

Val Phe Ala Val Leu Ser Val Val Asn Arg Val Arg Gln Gly Tyr Ser
705                 710                 715                 720

Pro Leu Ser Phe Gln Thr His Leu Pro Ile Pro Arg Gly Pro Asp Arg
                725                 730                 735

Pro Glu Gly Ile Glu Glu Glu Gly Gly Glu Arg Asp Arg Asp Arg Ser
                740                 745                 750

Ile Arg Leu Val Asn Gly Ser Leu Ala Leu Ile Trp Asp Asp Leu Arg
            755                 760                 765

Ser Leu Cys Leu Phe Ser Tyr His Arg Leu Arg Asp Leu Leu Leu Ile
            770                 775                 780

Val Thr Arg Ile Val Glu Leu Leu Gly Arg Arg Gly Trp Glu Ala Leu
785                 790                 795                 800
```

```
Lys Tyr Trp Trp Asn Leu Leu Gln Tyr Trp Ser Gln Glu Leu Lys Asn
            805                 810                 815

Ser Ala Val Ser Leu Leu Asn Ala Thr Ala Ile Ala Val Ala Glu Gly
        820                 825                 830

Thr Asp Arg Val Ile Glu Val Val Gln Gly Ala Tyr Arg Ala Ile Arg
            835                 840                 845

His Ile Pro Arg Arg Ile Arg Gln Gly Leu Glu Arg Ile Leu Leu
        850                 855                 860

<210> SEQ ID NO 6
<211> LENGTH: 23
<212> TYPE: PRT
<213> ORGANISM: retroviral provirus

<400> SEQUENCE: 6

Asn Asn Thr Arg Lys Ser Ile Arg Ile Gln Arg Gly Pro Gly Arg Ala
1               5                   10                  15

Phe Val Thr Ile Gly Lys Ile
            20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide primer

<400> SEQUENCE: 7
tcccgccttc cagctgtgac                                            20

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide primer

<400> SEQUENCE: 8
gtgctgctgt gttatgtcct                                            20

<210> SEQ ID NO 9
<211> LENGTH: 24
<212> TYPE: PRT
<213> ORGANISM: retroviral provirus

<400> SEQUENCE: 9

Cys Asn Asn Thr Arg Lys Ser Ile Arg Ile Gln Arg Gly Pro Gly Arg
1               5                   10                  15

Ala Phe Val Thr Ile Gly Lys Ile
            20
```

ANTI-HIV ANTIBODY

TECHNICAL FIELD

The present invention relates to an antibody that binds to gp120 (a glycoprotein with a molecular weight of about 120 kD in the envelope of HIV) with high affinity, and a cell producing the same. The present invention also relates to a pharmaceutical composition comprising the above antibody

BACKGROUND ART

Acquired immunodeficiency syndrome (AIDS) refers to a condition of HIV (human immunodeficiency virus) infected individuals where immunopotency has gradually decreased and complications easily occur.

Once HIV invaded the body of a host, HIV infects CD4 positive cells, particularly $CD4^+$ T lymphocytes (helper T cells). The protein that is involved in HIV infection of CD4 positive cells is an HIV envelope protein called gp120, which is a glycoprotein with a molecular weight of about 120 kD present in the envelope of HIV and binds to CD4 molecule on cell surfaces as a specific receptor. After infecting $CD4^+$ lymphocytes, HIV invades inside of cells, undergoes uncoating and liberates its nucleic acid (RNA). Then, DNA is synthesized by reverse transcriptase, transcribed and translated. Thus, viral proteins are synthesized. The viral proteins migrate to cell membranes to form virions, which are then released.

Since the antigenic drift of HIV is very frequent, vaccine preparation is difficult and no effective vaccine has been developed yet. Further, since HIV gene is integrated into the chromosomes of infected cells, it is extremely difficult to conduct a drastic treatment of removing the infecting HIV completely.

Currently, drugs such as AZT (azidothymidine) are recognized to be effective in postponing the onset of AIDS and prolonging the lives of patients; and new therapeutics with promising efficacy are being developed one by one. However, no decisive therapeutic has been established yet.

On the other hand, various attempts have been made to obtain antibodies that have the ability to effectively neutralize HIV and are useful for prevention or diagnosis of AIDS. Since gp120 is one of the most important molecules for HIV infection (McDougal et al., Science, 231,382-385 (1986)), it is possible to target gp120 in effective inhibition, prevention and diagnosis of HIV infection. An antibody called "0.5β" has already been prepared which recognizes one epitope present within amino acids 308-331 of the amino acid sequence of gp160, a precursor of the HIV gp120 (Japanese Patent No. 2797099). However, for further enhancing the avidity to antigen, it is necessary to develop high affinity antibodies that can react with the HIV gp120 and effectively neutralize the virus.

DISCLOSURE OF THE INVENTION

It is an object of the present invention to provide a high affinity antibody having the ability to neutralize HIV and a pharmaceutical composition comprising the antibody. It is another object of the invention to provide a pharmaceutical composition useful in treating acquired immunodeficiency syndrome.

As a result of intensive and extensive researches toward the solution of the above problems, the present inventors have found that a GANP transgenic non-human mammal immunized with gp120 produces an antibody that neutralizes the activity of HIV and binds to HIV with high affinity. Thus, the present invention has been achieved.

The present invention relates to the following.

(1) An antibody or a fragment thereof which binds to the gp120 glycoprotein of HIV and has a dissociation constant (KD) value of $1.0 \times 10^{-9}$ (M) or less.

The above-described antibody or fragment thereof is capable of recognizing at least a part of an amino acid sequence spanning from amino acid positions 308 to 330 of the gp120 glycoprotein (e.g., the amino acid sequence as shown in SEQ ID NO: 6).

The antibody or fragment thereof of the present invention may be an antibody collected from a serum of a non-human mammal; the antibody may be a polyclonal antibody or a monoclonal antibody The antibody or fragment thereof of the present invention is produced, for example, by a hybridoma cell having an accession number of FERM BP-08644 [designation: "Anti-NL43mono. Clone No. G2-25 hybridoma cell"; depository: International Patent Organism Depositary, National Institute of Advanced Industrial Science and Technology (Tsukuba Central 6, 1-1-1 Higashi, Tsukuba, Ibaraki, Japan; zip code No. 305-8566); date of deposit: Feb. 25, 2004].

(2) A humanized antibody or human antibody, or a fragment thereof, which comprises the V region of the above-described antibody or fragment thereof (3) A high affinity antibody-producing cell collectable from a GANP transgenic non-human mammal, or a progeny thereof, that was immunized with a polypeptide comprising at least a part of the amino acid sequence as shown in SEQ ID NO: 6 as an antigen.

The present invention also provides a cell producing a monoclonal antibody to the gp120 glycoprotein of HIV, which has an accession number of FERM BP-08644.

(4) A method of producing an anti-HIV antibody or a fragment thereof, comprising immunizing a GANP transgenic non-human mammal or a progeny thereof with a polypeptide comprising at least a part of the amino acid sequence as shown in SEQ ID NO: 6 as an antigen and collecting the antibody from the resultant mammal or progeny.

(5) A method of producing an anti-HIV antibody or a fragment thereof, comprising culturing a fusion cell composed of the high affinity antibody-producing cell of (3) above and a myeloma cell, or the monoclonal antibody-producing cell having an accession number of FERM BP-08644, and collecting the antibody from the resultant culture.

(6) A pharmaceutical composition comprising at least one selected from the group consisting of the antibody or fragment thereof of (1) above and the humanized antibody or human antibody, or fragment thereof of (2) above.

The pharmaceutical composition of the present invention may be used as a therapeutic for acquired immunodeficiency syndrome.

(7) A method of detecting HIV, comprising reacting the antibody or fragment thereof of (1) above, or the humanized antibody or human antibody, or fragment thereof of (2) above with the gp120 glycoprotein of HIV.

(8) An HIV detection kit comprising at least one selected from the group consisting of the antibody or fragment thereof of (1) above and the humanized antibody or human antibody, or fragment thereof of (2) above.

BEST MODE FOR CARRYING OUT THE INVENTION

1. Outline

Figure 1:
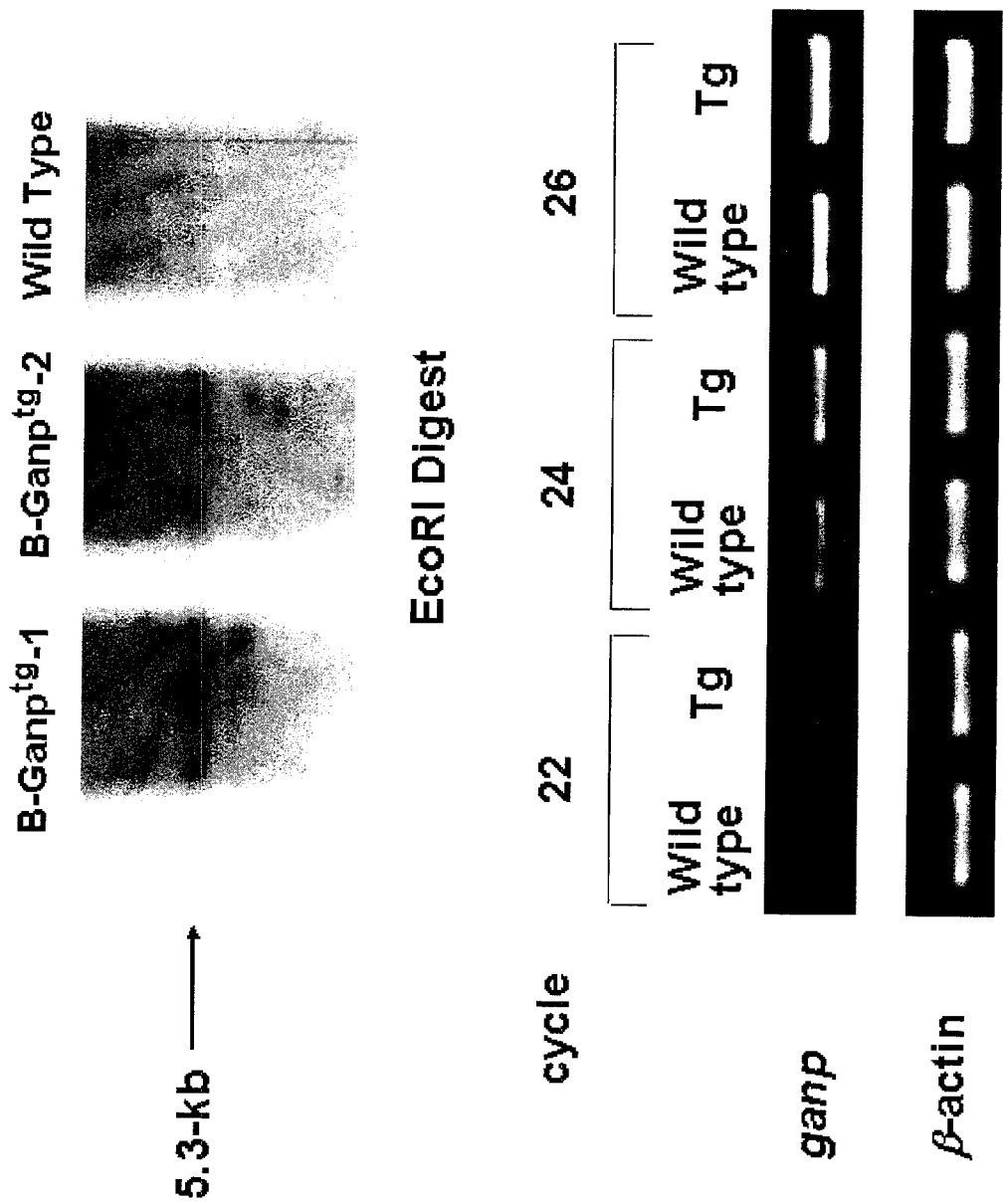
FIG. 1 is panels showing increases of GANP expression in B cells.

The antibody of the invention is obtainable by immunizing a GANP transgenic mammal with a part of the gp120 of HIV, in particular, a peptide consisting of an amino acid sequence spanning from amino acid positions 308 to 330 in the amino acid sequence of gp120 as an antigen. Although it is known that an antibody recognizing the partial amino acid sequence spanning from amino acid positions 308 to 330 in the amino acid sequence of gp120 (hereinafter, referred to as "gp120 (308-330)") has virus neutralizing activity and inhibitory activity against the syncytium formation by infected cells (Skinner M A. et al., AIDS Res. Hum. Retroviruses (1988), 4(3), 187-197), the antibody of the present invention is characterized by binding to gp120(308-330) with high affinity.

GANP is a nuclear protein called germinal center-associated nuclear protein. GANP is a molecule needed directly or indirectly in the process of induction of mutations in genes. Since GANP has the ability to promote induction of mutations in the V region so that high affinity antibodies are obtained. Therefore, a transgenic non-human mammal into which a gene encoding GANP has been introduced (hereinafter, called the "GANP transgenic non-human mammal") is, as a result of the GANP gene introduction, capable of promoting the production of high affinity antibodies of acquired immunity Further, this GANP transgenic non-human mammal is capable of promptly producing antibodies with high avidity to antigens. Therefore, by immunizing the above-described GANP transgenic non-human mammal with a peptide consisting of a partial amino acid sequence of HIV gp120 (for example, gp120 (308-330)) as an antigen, it is possible to obtain easily antibodies with high affinity which were unobtainable by conventional methods.

As described so far, according to the present invention, it becomes possible to obtain anti-HIV antibodies having HIV neutralizing activity, inhibitory activity against syncytium formation by infected cells, and high affinity that could not be achieved by conventional methods. Further, a pharmaceutical composition comprising the resultant antibody may be used for treating AIDS.

Cells producing the above-described antibody may be splenic B cells or lymph node cells alone obtained from a GANP transgenic non-human mammal immunized with gp120. Alternatively, the antibody-producing cell may be a hybridoma cell obtained by fusing such B cells or lymphocytes with a myeloma cell. The present invention also provides a cell producing the above-described antibody.

In clinical tests conducted to confirm HIV infection, it is important to detect HIV with high sensitivity. The high affinity anti-HIV antibody of the invention may be used as a means to detect HIV. Therefore, the present invention provides an HIV detection kit comprising the anti-HIV antibody of the invention.

2. Preparation of Antigen

Sequence information for HIV gp120 may be obtained from databases or the like (PRF 1102247A, http://www-.genome.ad.jp/dbget-bin/www_bget?prf:1102247A); the amino acid sequence of gp120 is as shown in SEQ ID NO: 5.

The polypeptide sequence of gp120(308-330) consists of the 23 amino acid residues as described below (Lee Ratner et al., Nature 313, 277-284, 1985):

NNTRKSIRIQRGPGRAFVTIGKI (SEQ ID NO: 6)

A polypeptide or peptide (sometimes simply referred to as "peptide") comprising at least a part (i.e., the whole or a part) of the amino acid sequence may be used as an antigen.

It should be noted here that "at least a part of the amino acid sequence" of the peptide sequence represented by SEQ ID NO: 6 to be used as an antigen is not particularly limited in length. For example, 8 or more consecutive amino acid residues in the 23 amino acid residues (e.g., 8, 10, 12, 16, 20 or 23 amino acid residues) may be included. Any site may be selected as long as the site consists of consecutive amino acids in SEQ ID NO: 6. For example, when 7 to 8 amino acids are to be used as an antigen, the amino acid sequences of three regions each consisting of 7 to 8 amino acids may be selected from the N-terminus toward the C-terminus of the amino acid sequence consisting of the 23 amino acid residues shown in SEQ ID NO:6. Alternatively, the amino acid sequence of a region consisting of 7 to 8 amino acids starting from the N-terminus may be selected, and then the amino acid sequence of subsequent regions serially shifted toward the C-terminus by one amino acid at one time may be selected in succession.

SEQ ID NO: 6 and the above-described at least a part of this amino acid sequence may be used independently or in combination, as an antigen.

Alternatively, the above-described peptide may be linked to a carrier protein to prepare an antigen that has a large number of the peptide as side chains. In this case, it is possible to add a cysteine residue to the N-temlinus to the above peptide in order to allow a carrier protein to bind thereto.

The peptide may be prepared by chemical synthesis or biochemical synthesis using *Escherichia coli* or the like. Methods well-known in those skilled in the art may be used for the synthesis.

When the peptide of the invention is chemically synthesized, methods well-known in the field of peptide synthesis may be used. For example, such methods as the azide method, the acid chloride method, the acid anhydride method, the mixed acid anhydride method, the DCC method, the active ester method, the carboimidazole method and the oxidation-reduction method may be enumerated. Either solid phase synthesis or liquid phase synthesis may be used. A commercial peptide synthesizer (e.g., Shimadzu PSSM-8) may also be used.

After the reaction, the peptide of the invention may be purified by a combination of conventional purification methods such as solvent extraction, distillation, column chromatography, liquid chromatography or re-crystallization.

When the peptide of the invention is biochemically synthesized, a DNA encoding the peptide is designed and synthesized. Then, this DNA is ligated to an appropriate vector to thereby obtain a recombinant vector for protein expression. By introducing this recombinant vector into a host in such a manner that the gene of interest is expressed, a transformant can be obtained (Sambrook J and Russel D., Molecular Cloning, A Laboratory Manual, 3rd edition, CSHL Press, 2001).

As a vector, a phage or plasmid capable of autonomous replication in a host microorganism is used. Examples of plasmid DNA include plasmids derived from *Escherichia coli, Bacillus subtilis* or yeast, and examples of phage DNA include λ phage. An animal virus vector or insect virus vector may also be used.

A recombinant vector may be prepared by digesting a purified DNA with appropriate restriction enzymes and inserting the digest into an appropriate restriction site or the like of a vector DNA for ligation.

The host used for transformation is not particularly limited as long as it is capable to expressing the gene of interest. Examples of hosts include bacteria (*Escherichia coli, Bacillus subtilis*, etc.), yeast, animal cells (COS cells, CHO cells, etc.), incest cells or insects. It is also possible to use a mammal such as goat as a host.

Methods of introduction of recombinant vectors into hosts are known. Any method (such as the method using calcium ions, electroporation, the spheroplast method, the lithium acetate method, the calcium phosphate method or lipofection) may be included in the methods.

In the present invention, the peptide of the invention may be obtained by culturing the above-described transformant and collecting from the resultant culture. The term "culture" used herein means any of the following materials: (a) culture supernatant, (b) cultured cells or cultured microorganisms, or a disrupted product obtained therefrom.

Culture method is well-known in the art (see Sambrook et al., Molecular Cloning, op. cit.).

After culturing, when the peptide of interest is produced in the microorganism or cell, the microorganism or cell is disrupted to extract the peptide. When the peptide of interest is produced outside the microorganism or cell, the culture broth may be used as it is or centrifuged to remove the microorganism or cell. Subsequently, the peptide of interest may be isolated/purified using common biochemical methods used in peptide isolation/purification (such as ammonium sulfate precipitation, gel filtration, ion exchange chromatography or affinity chromatography) independently or in combination.

In the present invention, it is also possible to adopt peptide synthesis by in vitro translation. Two methods may be applicable to this synthesis; one is a method using RNA as a template and the other is a method using DNA as a template (transcription/translation). As a template DNA, a DNA encoding the above peptide having a promoter and a ribosome binding site upstream of the translation start point or a DNA in which necessary elements for transcription (e.g., promoter) are integrated upstream of the translation start point may be included. As an in vitro translation system, a commercial system such as Expressway™ system (Invitrogen), PURESYSTEM (registered trademark; Post Genome Institute) or TNT system (registered trademark; Promega) may be used. After synthesis by an in vitro translation system, the peptide of interest can be isolated/purified by using the above-described common biochemical methods independently or in combination.

As a carrier protein to be linked to the thus obtained peptide, bovine serum albumin (BSA), keyhole limpet hemocyanin (KLH), human thyroglobulin or chicken gamma globulin may be enumerated.

3. GANP

GANP is a 210 kD nuclear protein having homology to yeast Sac3 protein (WO 00/50611). SAC3 is characterized as an inhibitory substance against actin formation. It is known that GANP is selectively up-regulated in germinal center (GC) B cells surrounded by follicular dendritic cells: FDC), has phosphorylation-dependent RNA primase activity, and is involved in the regulation of the cell cycle of B cells (Kuwahara, K. et al., (2000) Blood 95: 2321-2328).

In the present invention, the amino acid sequence for mouse GANP protein is shown in SEQ ID NO: 2 and the amino acid sequence for human GANP protein is shown in SEQ ID NO: 4. With respect to the gene encoding the GANP protein (hereinafter, referred to as "GANP gene"), the nucleotide sequence for mouse GANP gene is shown in SEQ ID NO: 1 and the nucleotide sequence for human GANP gene is shown in SEQ ID NO: 3. The above-mentioned amino acid sequences and nucleotide sequences are also described in WO 00/50611.

GANP proteins may be mutant proteins; they may be those proteins which consist of the amino acid sequence as shown in SEQ ID NO: 2 or 4 wherein one or a plurality of amino acids have been deleted, substituted or added and have RNA primase activity. For example, a GANP mutant protein may also be used which consists of the amino acid sequence as shown in SEQ ID NO: 2 or 4 wherein one or a plurality of amino acids (preferably, one or several (e.g. one to ten, more preferably one to five) amino acids) have been deleted, one or a plurality of amino acids (preferably, one or several (e.g. one to ten, more preferably one to five) amino acids) have been substituted with other amino acids, and/or one or a plurality of other amino acids (preferably, one or several (e.g. one to ten, more preferably one to five) amino acids) have been added thereto, and yet has the same RNA primase activity as that of the above-described GANP protein.

"RNA primase activity" means the enzyme activity synthesizing a short primer RNA which will be a starting point for strand elongation when a strand extending opposite to the 5'→3' direction (lagging strand) is synthesized in RNA replication. Usually, a molecule called a primase, which binds to DNA polymerase a is used. In germinal center B cells, GANP primase which is the second primase is also induced.

GANP protein includes a protein having the amino acid sequence as shown in SEQ ID NO: 2 or 4, or a mutant amino acid sequence thereof, and a protein having a part of the N-terminal sequence of those sequences (e.g. positions from 1 to 600, preferably from 139 to 566 of the amino acid sequence as shown in SEQ ID NO: 2) or a mutant amino acid sequence thereof.

In the present invention, a GANP gene to be transferred into an animal may be a gene encoding the above-described GANP protein, a part of the N-terminal sequence of the GANP protein, or a mutant GANP protein. Specific examples of such a gene include a gene having the nucleotide sequence as shown in SEQ ID NO: 1 or 3. A gene having only the coding region of the nucleotide sequence as shown in SEQ ID NO: 1 or 3 may also be used. Alternatively, it is also possible to use a gene that has a sequence hybridizable to a complementary sequence to the nucleotide sequence as shown in SEQ ID NO: 1 or 3 under stringent conditions, and encodes a protein having RNA primase activity.

"Stringent conditions" refers to washing conditions after hybridization; specifically, the salt (sodium) concentration is 150-900 mM and the temperature is 55-75° C., preferably salt (sodium) concentration is 250-450 mM and the temperature is 68° C.

Introduction of mutations into a gene may be performed according to known techniques such as the Kunkel method or the gapped duplex method, using mutagenesis kits utilizing site-directed mutagenesis, such as GeneTailor™ Site-Directed Mutagenesis System (Invitrogen) or TaKaRa Site-Directed Mutagenesis System (Mutan-K, Mutan-Super Express Km, etc.; Takara Bio), etc.

Details of mutant genes and methods for obtaining the same are also described in WO 00/50611.

In vitro stimulation of B cells with anti-i antibody and anti-CD40 monoclonal antibody induces not only the up-regulation of GANP expression but also the phosphorylation of a specific serine residue in the amino acid sequence of GANP protein (e.g. serine at position 502: S502). This reaction is a key reaction for the RNA primase activity of GANP (Kuwahara, K. et al. (2001) Proc. Natl. Acad. Sci. USA, 98, 10279-10283). The N-terminal primase domain of GANP protein contains a serine residue whose phosphorylation is catalyzed by Cdk2 in vitro. GANP binds to MCM3 replication licensing factor due to its C-terminal domain (Kuwahara, K. et al., (2000) Blood 95: 2321-2328; Abe, E. et al., (2000) Gene 255: 219-227).

GANP gene-deficient mice are embryonic lethal. The inventors created a conditional targeting mouse selectively lacking GANP gene in B cell by crossing CD19-Cre mouse with flox-ganp mouse, immunizing the resultant mouse with nitrophenyl (NP)-chicken gamma globulin antigen (T cell dependent antigen) and examined the mouse for NP-hapten specific antibody production. The results revealed that the high affinity antibody production in this mouse is remarkably hindered, indicating that GANP molecule plays an important role in enhancing the affinity of antibodies.

4. GANP Gene Transferred Transgenic Non-Human Mammal

The target animal to be immunized with gp120 is a GANP gene transferred transgenic non-human mammal. Preferably, the GANP gene transferred transgenic non-human mammal is capable of expressing the transferred GANP gene in B cells.

(1) GANP Gene and its Related Molecules

Complexes formed by GANP gene and its related molecules are needed directly or indirectly in the process of induction of mutations in genes. When repairing genetic mutations, GANP protein has the ability to promote induction of mutations in the V region so that high affinity antibodies are obtained. Therefore, the transgenic non-human mammal of the invention is capable of promoting the production of high affinity antibodies of acquired immunity because of the introduction of this GANP gene or a mutant thereof Further, a transgenic non-human mammal overexpressing this gene is capable of promptly producing antibodies with high avidity to antigens. Therefore, by immunizing the above-described transgenic non-human mammal with a specific antigen, it is possible to obtain easily antibodies with high affinities which were unobtainable by conventional methods. As a result, it becomes possible to obtain polyclonal or monoclonal antibodies capable of eliminating obstinate pathogenic microorganisms or foreign substances. Further, by preparing humanized antibodies using the transgenic non-human mammal of the invention, or by preparing single chain antibodies comprising the V region of the antibody produced by the transgenic non-human mammal of the invention, it becomes possible to sharply increase the effect of antibody therapy.

Because of the GANP gene or its mutant transferred thereinto, the transgenic non-human mammal of the invention is capable of promoting the production of high affinity antibodies in B cells, and the high affinity antibody-producing cells have resistance to apoptosis induction signals.

(2) Mammals for Use in GANP Gene Transfer

The term "mammal" used in the present invention means any of non-human mammals such as bovine, horse, pig, goat, rabbit, dog, cat, mouse, rat, hamster and guinea pig. Preferably, mouse, rabbit, rat or hamster is used. Most preferably, mouse is used.

The transgenic non-human mammal of the invention may be prepared by introducing a GANP gene into unfertilized eggs, fertilized eggs, embryonic cells comprising spermatozoa and protocells thereof, preferably into cells of embryogenesis stage (more preferably, the single cell or fertilized egg cell stage and yet generally before eight-cell stage) in the development of non-human mammals, by a method such as the calcium phosphate method, electric pulsing, lipofection, aggregation, microinjection, the particle gun method, or the DEAE-dextran method. Further, it is also possible to transfer a GANP gene of interest into somatic cells, organs of the living body, tissue cells, etc. by the above-mentioned gene transfer methods to use the resultant cells, etc. for cell culture or tissue culture. Further, it is possible to create transgenic non-human mammals by fusing these cells with the above-described embryonic cells according to known cell fusion methods.

When a GANP gene is transferred into an animal of interest, it is preferred that the gene be transferred in the form of a gene construct in which the gene is ligated downstream of a promoter capable of directing expression of this gene in cells of the animal of interest. Specifically, a vector in which a GANP gene is ligated downstream of various promoters capable of directing expression of the GANP gene derived from various mammals having the GANP gene of interest may be microinjected into fertilized eggs of the mammal of interest (e.g. mouse fertilized eggs) to thereby create a transgenic non-human mammal capable of high expression of the GANP gene of interest.

(3) Expression Vector

Examples of expression vectors for GANP gene include plasmids derived from *Escherichia coli*; plasmids derived from *Bacillus subtilis*; plasmids derived from yeast; bacteriophages such as λ-phage; retroviruses such as Moloney leukemia virus; and animal or insect viruses such as vaccinia virus or baculovirus.

As promoters for regulating gene expression, promoters of viruses-derived genes; promoters of various mammals (such as human, rabbit, dog, cat, guinea pig, hamster, rat and mouse)-derived genes; and promoters of birds (such as chicken)-derived genes may be used.

Examples of promoters of viruses-derived genes include promoters of cytomegalovirus-, Moloney leukemia virus-, JC virus-or breast cancer virus-derived genes.

Examples of promoters of various mammals- and birds-derived genes include promoters of albumin, insulin II, erythropoietin, endothelin, osteocalcin, muscle creatine kinase, platelet-derived growth factor β, keratin K1, K10 and K14, collagen type I and type II, atrial natriuretic factor, dopamine β-hydroxylase, endothelial receptor tyrosine kinase, sodium/potassium-dependent adenosine triphosphatase, neurofilament light chain, metallothionein I and IIA, metalloproteinase I tissue inhibitor, MHC Class I antigen, smooth muscle α-actin, polypeptide chain elongation factor 1α (EF-1α), β-actin, α- and β-myosin heavy chains, myosin light chains 1 and 2, myelin basic protein, serum amyloid P component, myoglobin and renin genes.

The above-described vector may have a terminator which terminates the transcription of a messenger RNA of interest in a transgenic non-human mammal. For the purpose of achieving still higher expression of GANP gene, the splicing signal of each gene, enhancer region, or a part of an intron of an eukaryotic gene may be ligated upstream (5') of the promoter region, between the promoter region and the translation region, or downstream (3') of the translation region, if desired.

In a preferred embodiment of the invention, it is possible to allow selective expression of the transferred GANP gene in B cells by ligating the GANP gene downstream of an immunoglobulin promoter or by ligating a human immunoglobulin gene intron enhancer moiety upstream (5') of the GANP gene.

(4) Transfer of GANP Gene

The transfer of GANP gene at the fertilized egg cell stage is preferably carried out in such a manner, for example, that excessive presence of GANP gene is secured in all the embryonic cells and somatic cells of the mammal of interest. Excessive presence of GANP gene in the embryo cells of the created animal after gene transfer means that all the progeny of that created animal has excessive GANP gene in all the embryonic cells and somatic cells. The progeny of this kind of animal which inherited the GANP gene has excessive GANP protein in all the embryonic cells and somatic cells.

In the present invention, first, heterozygotes which have the transferred gene in one of the homologous chromosomes are prepared; then, homozygotes which have the transferred gene in both of the homologous chromosomes are obtained by mating the heterozygotes with each other. Subsequently, by mating female homozygotes with male homozygotes, all the resultant progeny retains the transferred GANP gene stably After confirmation of the excessive presence of GANP gene, the progeny may be bred in usual breeding environments.

Fertilized eggs of a non-human mammal of interest (preferably, mouse) or its ancestor (back-crossing) to be used for transferring a foreign GANP gene different from the endogenous gene of the mammal of interest are obtained by mating allogenic male and female mammals.

Although fertilized eggs may be obtained by natural mating, it is preferred that female mammals after artificial adjustment of their sexual cycle be mated with male mammals. As a method for artificially adjusting the sexual cycle of female mammals, such a method may be used preferably in which follicle-stimulating hormone (pregnant mare serum gonadotropin (PMSG)) and then luteinizing hormone (human chorionic gonadotropin (hCG)) are administered by, e.g., intraperitoneal injection.

After the transfer of a foreign GANP gene into the resultant fertilized eggs by the methods described above, the eggs are artificially transferred/implanted in female mammals. As a result, non-human mammals having a foreign gene-integrated DNA are obtained. In a preferable method, fertilized eggs are transferred/implanted artificially in pseudo-pregnant female mammals in which fertility has been induced by mating with male mammals after administration of luteinizing hormone-releasing hormone (LHRH). As totipotent cells into which a gene is to be transferred, fertilized eggs or early embryos may be used if the mammal of interest is mouse. As a method of gene transfer into cultured cells, DNA microinjection is preferable in view of the production efficiency of transgenic non-human mammal individuals and the transmittance efficiency of the transgene to the subsequent generation.

Subsequently, the gene-injected fertilized eggs are transplanted into the oviduct of a recipient female mammal. Those animals which have developed from the eggs up to individuals and have been successively born are bred under foster parents. Then, DNA is extracted from a part of their bodies (e.g. the tail end in the case of mouse) and subjected to Southern analysis, PCR, etc. Thus, it is possible to confirm the presence of the transgene. Those animals in which the presence of the transgene has been confirmed are designated as founder animals. The transgene is transmitted to 50% of their offspring (F1). Further, by mating F1 individuals with wild-type animals or other F1 individuals, F2 individuals which have the transgene in one (heterozygote) or both (homozygote) of the diploid chromosomes can be produced.

Alternatively, transgenic non-human mammals expressing high levels of GANP protein may also be created by introducing the above-described GANP gene into ES (embryonic stem) cells. For example, the GANP gene is introduced into HPRT negative (i.e. lacking hypoxanthine-guanine phosphoribosyltransferase gene) ES cells derived from normal mouse blastocysts. Then, those ES cells in which the GANP gene has been integrated through homologous recombination induced in a mouse endogenous gene are selected by HAT selection. The thus selected ES cells are microinjected into fertilized eggs (blastocysts) obtained from other normal mouse. The resultant blastocysts are transferred into the uterus of other normal mouse as a recipient. Subsequently, chimeric transgenic mice are born from the recipient mouse. By mating these chimeric transgenic mice with normal mice, heterotransgenic mice can be obtained. Further, by mating the heterotransgenic mice with each other, homotransgenic mice can be obtained.

The present invention encompasses not only the above-described transgenic non-human mammal but also its progeny and a part of the transgenic non-human mammal or its progeny in the scope of the invention. As a part of the transgenic non-human mammal, a tissue, organ, cell or the like of the transgenic non-human mammal or its progeny may be enumerated. Specific examples of organs or tissues include the spleen, thymus, lymph nodes, bone marrow or tonsil; and specific examples of cells include B cells.

The transgenic non-human mammal of the invention may be mated with a mammal that further activates B cells. As a result of such mating, antibodies of still higher affinity can be produced.

Recently, it has been reported that when B cells are activated in peripheral lymph nodes in MRL/lpr mouse, mutagenesis in the V region is further increased in the T cell region after B cells passed through the germinal center. The present inventors have also found that non-immunized MRL/lpr mouse shows high expression equivalent to the expression observed in ganp transgenic mouse which was created by ligating a GANP gene downstream of Ig promoter and enhancer. This suggests a possibility that, while high affinity antibodies are not produced against autoantigens normally, high affinity antibodies to autoantigens may be produced in this autoimmune disease mouse because of the abnormal activation of GANP molecule.

Then, still higher mutagenesis can be expected if autoimmune disease mouse such as MRL/lpr, NZB or (NZB×NZW) F1 is used as the above-mentioned animal that still activates B cells.

By creating a GANP transgenic mouse from MRL/lpr mouse utilizing what has been described above, it may be possible to create a super high affinity antibody-producing mouse. In other words, by mating the GANP gene overexpressing transgenic non-human mammal of the invention with various autoimmune disease model animals, it is possible to create mammals capable of producing high affinity antibodies.

5. Preparation of High Affinity Antibodies to HIV gp120

(1) High Affinity Antibodies

The term "antibody" used in the invention means the entire molecule of an antibody (either polyclonal or monoclonal) capable of binding to a peptide consisting of amino acids from positions 308 to 330 of the amino acid sequence of gp120 or a fragment of the above antibody. The isotype of the antibody of the invention is not particularly limited. The antibody of the invention may have any isotype, e.g. IgG ($IgG_1$, $IgG_2$, $IgG_3$, $IgG_4$), IgM, IgA ($IgA_1$, $IgA_2$), IgD or IgE.

In the present invention, an antibody having high reactivity with an antigen is called a high affinity antibody The term "high affinity" used herein means that the ability of an antibody to bind to an antigen is high. In the present invention, a high affinity antibody refers to an antibody which has higher ability to bind to an antigen than those antibodies prepared using conventional animals such as mouse, and which is slow in dissociating from that antigen. This means that such an antibody is high and specific in the ability to bind to an epitope sterically and closely Besides, the binding of such an antibody to the epitope induces changes not only in the epitope but also the structure of the antigen itself, to thereby show strong activities eventually (e.g. biological activities such as neutralization of toxicity, prevention of HIV infection, deactivation, and so forth).

The binding ability (i.e. affinity) of an antibody may be measured as dissociation constant (KD), dissociation rate constant (Kdiss) or association rate constant (Kass) by Scatchard analysis or with a surface plasmon resonance sensor called Biacore. Biacore systems in which three technologies of sensor chip, microflow system and SPR detection system are integrated are to measure the strength, rate and selectivity of molecular binding. This apparatus enables real time detection of biomolecules and monitoring of interactions among a plurality of molecules without using labels. Specific examples of Biacore systems include Biacore 3000, Biacore 2000, Biacore X, Biacore J and Biacore Q (all of them are manufactured by Biacore).

With the above-described Biacore system, parameters showing the affinity of antibodies, i.e. dissociation constant (KD), dissociation rate constant (Kdiss) [1/Sec] and association rate constant (Kass) [1/M. Sec] are measured.

Antibodies with smaller dissociation constant (KD) values are preferable because the smaller the dissociation constant value, the higher the affinity. The binding ability (affinity) of an antibody is determined by the two parameters of Kdiss and Kass, and is represented by the following formula:

$$KD(M)=Kdiss/Kass$$

Although the affinity of the resultant antibody varies depending on a plurality of factors such as types of antigen, KD value is preferably $1 \times 10^{-9}$ (M) or less, more preferably $1.5 \times 10^{-10}$ (M) or less, and still more preferably $1.0 \times 10^{-10}$ (M) or less (especially, $9.9 \times 10^{-11}$ (M) or less).

In the present invention, when the resultant antibody reveals any of the above-described effects or natures, the antibody is judged as a high affinity antibody The antibodies of the present invention (polyclonal antibodies and monoclonal antibodies and active fragments) may be prepared by any of various methods. Such antibody producing methods are well-known in the art.

(2) Preparation of Polyclonal Antibodies

The antigen prepared as described above is administered to a GANP transgenic non-human mammal. The kind of the mammal is not particularly limited. For example, rat, mouse or rabbit may be included. Among all, GANP transgenic mouse or GANP transgenic rabbit is preferable.

The dose of the antigen per animal is 5-50 mg when no adjuvant is used, and 0.5-2 mg when adjuvants are used. Examples of adjuvants include Freund's complete adjuvant (FCA), Freund's incomplete adjuvant (FIA), aluminium hydroxide adjuvant, trehalose dimycolate (TDM), lipopolysaccharide (LPS), silica adjuvant and commercial adjuvants. Immunization is performed by injecting the antigen intravenously, subcutaneously, and intraperitoneally, etc. The immunization interval is not particularly limited. Immunization is performed 1-10 times, preferably 2-3 times, at intervals of several days to several weeks, preferably 1-5 weeks. Six to sixty days after the final immunization, antibody titers are measured by such methods as ELISA (enzyme-linked immunosorbent assay), EIA (enzyme immunoassay) or RIA (radioimmuno assay). On the day when desired antibody titers are shown, blood is collected from animals to obtain antisera. When purification of the antibody is necessary in the above-described method of antibody collection, the antibody may be purified by appropriately selecting or combining known methods such as ammonium sulfate precipitation, ion exchange chromatography, gel filtration, affinity chromatography or the like.

Subsequently, the reactivities of polyclonal antibodies in the antisera are measured by ELISA or the like.

(3) Preparation of Monoclonal Antibodies

(a) Collection of Antibody-Producing Cells

The antigen prepared as described above is administered to a GANP transgenic non-human mammal (e.g., rat, mouse or rabbit). The dose of the antigen per animal is 0.05-2 mg when no adjuvant is used, and 0.05-2 mg when adjuvants are used. Examples of adjuvants include Freund's complete adjuvant (FCA), Freund's incomplete adjuvant (FIA), aluminium hydroxide adjuvant, BCG, trehalose dimycolate (TDM), lipopolysaccharide (LPS) and silica adjuvant. Preferably, FCA and FIA are used in combination in view of the ability to induce antibodies, etc. Immunization is performed mainly by injecting the antigen intravenously, subcutaneously or intraperitoneally After the first immunization, preferably, the animals are boosted several times; after passage of appropriate number of days, blood sanples are taken and antibody titers are measured by the method described above. Since antibodies produced by the method of the invention are high affinity antibodies, the first immunization may be sufficient only with the first immunization. The immunization interval is not particularly limited. Immunization is performed 1-10 times, preferably 1-5 times, at intervals of several days to several weeks, preferably 2-5 weeks. One to sixty days, preferably 1-14 days, after the final immunization, antibody-producing cells are collected. As antibody-producing cells, splenocytes, lymph node cells, peripheral blood cells or the like may be enumerated. Among all, splenocytes or local lymph node cells are preferable.

The high affinity antibody-producing cells obtained as described above are also included in the present invention.

(b) Cell Fusion

When a GANP transgenic mouse is used, for example, cell fusion of antibody-producing cells and myeloma cells is conducted to obtain hybridoma cells. As a myeloma cell to be fused to the antibody-producing cell, a commonly available cell line derived from a mammal such as mouse may be used. Specifically, a preferable cell strain to be used in the invention has drug selectivity, cannot survive in HAT selection medium (containing hypoxanthine, aminopterin and thymidine) in unfused conditions, and can survive there only after fusion to antibody-producing cells. Specific examples of mouse myeloma cell strains useful in the invention include P3-X63.Ag8(X63), P3-X63.Ag8.U1(P3U1), P3/NS I/1-Ag4-1(NSI) and Sp2/0-Ag14(Sp2/0). In the selection of myeloma cells, compatibility with antibody-producing cells should be considered appropriately.

Subsequently, the above-described myeloma cell and the antibody-producing cell are fused. Briefly, $1 \times 10^6$-$1 \times 10^7$ cells/ml antibody-producing cells are mixed with $2 \times 10^5$-$2 \times 10^6$ cells/ml myeloma cells (preferable cell ratio of antibody-producing cells to myeloma cells is 5:1) in an animal cell culture medium such as serum-free DMEM or RPMI-1640, and fused in the presence of a cell fusion promoter. As the cell fusion promoter, polyethylene glycol with a mean molecular weight of 1000-6000 daltons (D) may be used. Alternatively, it is also possible to fuse antibody-producing cells and myeloma cells with a commercial cell fusion device utilizing electric stimulation (e.g., electroporation).

(c) Selection of Hybridomas and Cloning Thereof

Hybridomas of interest are selected from the cells after cell fusion. Briefly, the cell suspension is diluted, for example, with fetal bovine serum-containing RPMI-1640 medium and plated over microtiter plates. The selection medium is added to each well, and cells are cultured with appropriate exchange of the selection medium. Those cells which begin to grow about 14 days after the start of culture in the selection medium can be obtained as hybridomas.

Subsequently, screening is carried out to examine whether or not antibodies reactive with gp120 are present in the culture supernatant of the growing hybridomas. The screening of hybridomas may be performed by conventional methods and is not particularly limited. For example, aliquots of culture supernatants contained in those wells where hybridoma cells are growing are collected and subjected to screening by methods such as ELISA, EIA or RIA.

The cloning of fused cells is performed by the limiting dilution culture method or the like. Those hybridomas producing an antibody showing strong reactivity with gp120 and having a KD value (indicator of affinity) of $1 \times 10^9$ (M) or less are selected and established.

(d) Collection of Monoclonal Antibodies

As a method of culturing the established hybridoma and collecting monoclonal antibodies from the resultant culture, a conventional cell culture method or the ascites formation method may be used. The term "culturing" means to grow the above-described hybridoma in a plate or dish, or to proliferate the above-described hybridoma in the abdominal cavity as described below. The term "culture" means any of the following: culture supernatant, cultured cells or disrupted cultured cells, or ascites.

In the cell culture method, the hybridoma cells are cultured in an animal cell culture medium (such as 10% fetal bovine serum-containing RPMI-1640 medium, MEM medium or serum-free medium) under conventional culture conditions (e.g., at 37° C. under 5% $CO_2$) for 7 to 14 days. Then, the antibody of interest is obtained from the culture supernatant.

In the ascites formation method, the hybridoma cells are administered into the abdominal cavity of an allogenic animal (approx. $1 \times 10^7$ cells/animal) to the mammal from which the myeloma cell used in the cell fusion was derived, to thereby expand the hybridoma cells greatly One to two weeks thereafter, the ascites is collected.

When purification of antibodies is necessary in the above-described methods of monoclonal antibody collection, antibodies may be purified by a conventional method selected from ammonium sulfate precipitation, ion exchange chromatography, gel filtration, affinity chromatography or the like, or a combination of these methods.

(e) Use of the Binding Domain of Monoclonal Antibodies

Monoclonal antibodies bind to HIV antigen to thereby have activities to prevent HIV infection and neutralize and eliminate HV. During this process, which V region gene is used in the H chain? Which D region gene or J region gene is used? Is N sequence inserted or not? Or which L chain V region gene is used? Is J region gene used or not? Information about these matters forms basis for creation of high affinity antibodies. However, binding affinity varies greatly not only by these matters but by the degree of somatic mutation of V region gene induced in peripheral lymphoid tissue. Here, the degree of somatic mutation is determined depending on the structures of regions involved in monoclonal antibody binding to antigen, i.e. the structures of each three CDR regions of the H chain and the L chain. Therefore, with the use of information about the high affinity binding domain obtained by the present invention, it is possible to establish an anti-HIV antibody-producing cell from human EB virus-transformed memory B cell strain and introduce the information obtained here into the V region of the antibody by direct genetic engineering technique, to thereby obtain a high affinity antibody.

(4) Antibody Fragments, Humanized Antibodies or Human Antibodies

It should be noted that fragments of the above-described antibody and single chain antibodies of the V region of the above-described antibody are also within the scope of the present invention. A fragment of the antibody means a portion of the above-described polyclonal or monoclonal antibody. Specific examples of such a fragment include $F(ab')_2$, Fab', Fab, Fv (variable fragment of antibody), sFv, dsFv (disulphide stabilized Fv) or dAb (single domain antibody). A single chain antibody has a structure in which $V_L$ (L chain variable region) and VH (H chain variable region) are ligated with a linker.

The high affinity antibody of the invention may be a humanized antibody or human antibody. These human antibodies may be prepared by using mammals whose immune system has been replaced with the human immune system. After immunizing such mammals, human antibodies may be prepared directly in the same manner as used in the preparation of conventional monoclonal antibodies.

For the preparation of humanized antibodies, reconstructed variable regions consisting of human-derived framework regions (FR) and mouse-derived CDRs (complementarity determining regions) are prepared by transferring the CDRs of the variable regions in a mouse antibody into the human variable regions.

Subsequently, these humanized, reconstructed human variable regions are ligated to human constant regions. Methods for preparing humanized antibodies are well-known in the art.

Human antibodies may be produced using any animal in terms of structure, though generally the antigen binding site in the V region (i.e. hyper variable region) may raise some problem with respect to specificity and binding affinity. On the other hand, it is desirable that the structures of the remaining portion of the variable region and the constant region should be the same as the structures in human antibodies. With respect to genetic sequences common in human, genetic engineering techniques to prepare such sequences have been established.

(5) Characteristics of the Antibody The antibody produced by the GANP transgenic non-human mammal of the invention has at least one of the following natures (i) to (iv).

(i) The antibody binds to the glycoprotein antigen gp120 with a molecular weight of 120 kD in the envelope of HIV and neutralizes HIV.

(ii) By binding to the surfaces of HIV-infected cells, the antibody inhibits syncytium formation induced by infected cells and non-infected T cells.

(iii) The antibody recognizes at least a part of region gp120 (308-330) as epitope.

(iv) The antibody binds to at least a part of region gp120 (308-330) with high affinity ($KD=1\times10^9$ (M) or less).

The syncytium formation means that an infected cell incorporates a non-infected cell into itself to thereby form one cell. When HIV is cultured with cells in vitro, sometimes syncytia are formed. Such syncytia cannot survive, and die. It is known that individuals infected with syncytium inducing (SI type) HIV show rapid decrease in $CD4^+$ lymphocytes and develop AIDS swiftly.

6. Pharmaceutical Compositions

The high affinity antibody of the invention which is raised against HIV (the causative of AIDS) as its antigen has an effect of neutralizing the activity of HIV. Therefore, the antibody of the invention is useful for therapeutic or prophylactic pharmaceutical compositions for AIDS. The pharmaceutical composition of the invention is provided comprising the high affinity antibody of the invention or a fragment thereof as an active ingredient, preferably provided in a form of a pharmaceutical composition comprising a pharmacologically acceptable carrier(s) additionally.

The "pharmacologically acceptable carrier" used herein includes excipients, diluents, fillers, disintegrants, stabilizers, preservatives, buffers, emulsifiers, aromatics, coloring agents, sweetening agents, thickening agents, flavoring agents, dissolution aids and other additives. By using one or more of these carriers, various forms of pharmaceutical compositions may be prepared, e.g. injections, solutions, capsules, suspensions, emulsions and syrups. These pharmaceutical compositions may be administered orally or parenterally. Other forms for parenteral administration include injections which comprise one or more active substances and are prescribed by conventional methods.

The dose of the drug of the invention varies depending on the age, sex, body weight and conditions of the patient, treatment effect, the method of administration, time period for treatment, or the type of the high affinity antibody (the active ingredient) contained in the drug. Usually, the drug of the invention may be administered to adults in the range from 10 μg to 1000 mg per administration, preferably in the range from 10 μg to 100 mg per administration. However, the dose is not limited to this range. When the body weight of a patient is 60 kg, the amount of his/her body fluid may be estimated 5 liters. In in vitro experiments, effective concentrations of antibodies are usually 5-50 μg/ml. According to simple calculation, it is desirable that 25-250 mg of the antibody is present in body for at least several days.

For example, in the case of injections, the antibody of the invention may be dissolved or suspended in a pharmacologically acceptable carrier (such as saline or commercial distilled water for injection) so that the antibody concentration is from 0.1 μg/ml (antibody/carrier) to 10 mg/ml (antibody/carrier). The thus prepared injection may be administered to human patients in need of treatment at a rate of 1 μg-100 mg/kg body weight, preferably at a rate of 50 μg-50 mg/kg body weight, per administration once to several times per day. The route of administration may be intravenous injection, subcutaneous injection, intradermal injection, intramuscular injection or intraperitoneal injection, for example. Among all, intravenous injection is preferable. Optionally, injections may be prepared in the form of a non-aqueous diluent (e.g. propylene glycol, polyethylene glycol, vegetable oil such as olive oil, alcohol such as ethanol), suspension or emulsion. Sterilization of such injections may be performed, for example, by filter-sterilization through a bacteria removal filter or addition of antiseptics. Injections may take a form that is prepared into an injection at the time of use. Briefly, a sterile solid composition is prepared by lyophilization or the like, and this solid composition may be dissolved in aseptic distilled water for injection or other solvent at the time of use.

7. HIV Detection Kit

The high affinity antibody of the invention is useful as a drug for diagnosing, treating or preventing diseases.

Detection of HIV infection using the antibody of the invention is carried out by binding samples taken from subjects (such as saliva or blood) and the antibody of the invention or a fragment thereof by antigen-antibody reaction, and determining the amount of antigen of interest in the sample from the amount of bound antibody. The amount of antibody may be detected by known methods of immunological measurement. For example, immunoprecipitation, immunoagglutination, labeled immunoassay, turbidity immunoassay or the like may be used. Labeled immunoassay is especially preferable because of simplicity and high sensitivity. In labeled immunoassay, the antibody titer in a sample is represented by the amount of label detected directly with a labeled antibody. Alternatively, the antibody titer may be represented relatively using an antibody of known concentration or known titer as a standard solution. Briefly, a standard solution and a sample are measured with a meter; then, using the resultant value of the standard solution as a standard, the antibody titer in the sample may be expressed relatively. As a labeled immunoassay, any known method such as ELISA, EIA, RIA, FIA (fluoroimmunoassay) or luminescence immunoassay may be used.

By using the high affinity antibody of the invention, it is possible to evaluate the efficacy of AIDS therapeutics with high sensitivity. The method of efficacy evaluation using the high affinity antibody of the invention may be carried out as follows. Test drugs are administered to AIDS patients or AIDS model animals prepared by transplanting human lymphocytes (SCID-Hu mouse); then, the amounts of HIV in these bodies or the amounts of immuno deficient virus in model animal bodies are detected with the high affinity antibody of the invention. By comparing the resultant amounts, it is possible to evaluate the efficacies of test drugs as an AIDS therapeutic through the amounts of the antigen in bodies. At this time, the antibody of the invention is expected to have sensitivity 2- to 100-fold higher than that of conventional antibodies.

The high affinity antibody of the invention may be provided in a form of diagnosis kit for various diseases. This kit may be used in the diagnosis method and the efficacy evaluation method of the invention. Further, this kit may also be used as a highly sensitive, rapid and simple kit for checking the presence/absence of HIV infection in blood transfusion preparations and biological samples. The kit of the invention comprises at least one component selected from the following (a) and (b).

(a) The antibody of the invention or a labeled product thereof (b) An immobilizing reagent in which the antibody or labeled product of (a) above is fixed.

Here, the labeled product of antibody means an antibody labeled with an enzyme, radioactive isotope, fluorescent compound or chemiluminescent compound.

In addition to the above-described components, the kit of the invention may comprise other reagents to conduct the detection of the invention, e.g., when the labeled product is an enzyme-labeled antibody, an enzyme substrate (color developing substrate, etc.), enzyme substrate solution, enzyme reaction termination solution, or dilution for samples.

Hereinbelow, the present invention will be described in more detail with reference to the following Examples. However, the present invention is not limited by these Examples.

In the following Example, three types of mice were used. They were Balb/c mouse (usually used in immunization), wild type (WT) mouse and GANP transgenic (Tg) mouse. Individuals of these three mice were immunized with as an immunizing antigen, HIV24NL43 (308-330) peptide (which is expected to neutralize HIV) linked to a carrier protein. Two individuals from each type of mouse were used to carry out cell fusion. The resultant cells were screened by ELISA and measurement with a Biacore system to thereby obtain positive hybridomas. Subsequently, purified antibodies obtained from individual hybridomas were analyzed by ELISA and measurement with a Biacore system.

The results revealed that monoclonal antibodies (3 clones) obtained from GANP transgenic (Tg) mouse are monoclonal antibodies with fairly high affinity. The dissociation constant (KD=k diss/k ass) value which is an indicator of affinity was $9.90 \times 10^{-11}$(M) in the clone with the highest affinity.

EXAMPLE 1

Preparation of GNAP Transgenic (Tg) Mouse

A transgene to be introduced into mice was prepared by inserting a 5.3 kb mouse GANP gene into the EcoRI site of pLG vector. This vector having a human immunoglobulin intron enhancer domain (2 kb EcoRi fragment) is a specific vector that directs strong expression in B cells. This gene was linearized and transferred into mice. Briefly, a linearized pLG vector (Koike, M. et al., Int. Immunol. 7, 21-30 (1995)) comprising the full-length mouse GANP cDNA was micro-injected into fertilized eggs of C57BL/6 mice. The presence of the transferred gene was screened using the genomic DNA obtained from mouse tail, the following primers and the reaction solution (upper panel, FIG. 1). In the upper panel of FIG. 1, the band appearing at around 5.3 kb represents the GANP gene.

```
1-5' primer:
5'-TCCCGCCTTCCAGCT GTGAC-3'      (SEQ ID NO: 7)

1-3' primer:
5'-GTGCTGCTGTGTTATGTCCT-3'       (SEQ ID NO: 8)
```

Composition of the Reaction Solution

| | |
|---|---|
| DNA (50 ng/μl) | 1 μl |
| 10× buffer | 2.0 μl |
| 2.5 mM dNTP mix | 2.0 μl |
| 1-5' primer (10 μM) | 0.8 μl |

-continued

| | |
|---|---|
| 1-3' primer (10 μM) | 0.8 μl |
| Z-Taq DNA polymerase | 0.1 μl |
| dH$_2$O | 13.3 μl |

Reaction Conditions:
[98° C. 5 sec; 59° C. 5 sec; 72° C. 10 sec]×35 cycles
4° C.

Whether the expression of GANP mRNA is enhanced or not was examined by RT-PCR.

Total RNA was extracted from the spleen or splenic B cells using Trizol (Invitrogen). RT-PCR was performed with two primers (1-5' primer and 1-3' primer) to synthesize cDNA (Kuwahara, K. et al., Blood 95, 2321-2328 (2000)). GANP transcript was detected by agarose gel electrophoresis. β-actin transcript was used as a control.

As a result, GANP transgenic mice exhibited increased expression of GANP in B cells (lower panel, FIG. 1) and showed normal differentiation of B lineage cells in surface marker analysis of bone marrow, spleen and lymph node cells.

EXAMPLE 2

Preparation of Antibodies (1) Materials
  (a) Animals: Balb/c mouse, wild type (WT) mouse and GANP transgenic (Tg) mouse
  (b) Immunizing antigen: HIV24NL43 peptide/KLH conjugation
  (c) ELISA antigen: HIV24NL43 peptide (sequence: CNNTRKSIRI QRGPGRAFVT IGKI (SEQ ID NO: 9))
  (d) Myeloma cell: P3-X63.Ag8.U1
  (e) Secondary antibody: HRP-labeled anti-mouse antibodies IgC, IgA and IgM (2) Methods Five individuals each of the above-described three types of mice were immunized with NL43 peptide (carrier protein: KLH) three times at intervals of two weeks. After the third immunization, antisera were collected and subjected to ELISA to measure antibody titers.

Two individuals showing high antibody titers were selected from each type of mice used, and antibody-producing cells (splenic cells) were collected therefrom and fused to P3U1 myeloma cell. Cells were plated to give a density of $0.2 \times 10^5$ GANP-Tg mouse splenic cells/well. Balb/c mouse-derived 5448 clones, wild-type (WT) mouse-derived 1888 clones and GANP transgenic (Tg) mouse-derived 2016 clones were cultured in HAT medium.

After day 9 of HAT culture, culture supernatants were collected and subjected to ELISA using NL43 peptide (1 μg/ml) as an immobilized antigen. From the individual populations of culture supernatants from GANP-Tg mice and WT mice, those clones showing an absorbance at 490 nm of 1.50 or more as determined by ELISA were selected and cloned in HT medium.

After day 9 of HT culture, culture supernatants were collected and subjected to ELISA using NL43 peptide (1 μg/ml) as an immobilized antigen. As a result, three hybridoma clones were established from Balb/c mice (B1-10, B2-24 and B2-27), 9 hybridoma clones were established from WT mice (W1-2, W1-7, W1-8, W1-10, W1-21, W1-43, W1-45, W1-63 and W1-84) and 8 hybridoma clones were established from GANP Tg mice (G1-22, G1-68, G1-124, G1-165, G1-181, G2-231, G2-10 and G2-25).

Of these clones, G2-25 was designated "Anti-NL43mono. Clone No. G2-25 hybridoma cell" and internationally deposited at International Patent Organism Depositary, National Institute of Advanced Industrial Science and Technology (Tsukuba Central 6, 1-1-1 Higashi, Tsukuba, Ibaraki, Japan; zip code No. 305-8566) on Feb. 25, 2004 under the accession number of FERM BP-08644 according to the Budapest Treaty.

Individual clones from GANP-Tg mice and WT mice were cultured in RPMI medium, and then further cultured in a serum free medium SFM. These clones were purified with protein G to thereby obtain anti-peptide monoclonal, purified antibodies.

EXAMPLE 3

Measurement of Affinity

Using the monoclonal antibodies prepared in Example 2 above, the following evaluation and examination were carried out.

In order to evaluate the affinity of each antibody, analyses by ELISA and with a Biacore system were conducted.

First, in ELISA, HIV24NL43 peptide (1 µg/ml) was used as immobilized antigen and immobilized at room temperature for one hour. The antigen-immobilized plate was washed with PBSTween 20 and blocked with 2.0% skim milk. After further washing with PBSTween 20, the antigen was reacted with the anti-peptide monoclonal antibodies (0.457-1 µg/ml) to be evaluated, at room temperature for one hour. Then, the resultant samples were washed with PBSTween 20 and reacted with HRP-labeled anti-mouse IgG, IgA or IgM at room temperature for one hour. After washing with PBSTween 20, color was developed with ortho-phenylene diamine (OPD) for 5 minutes, followed by temlination of the reaction with 2N sulfuric acid.

Absorbance was measured with an ELISA plate reader at 490 mm.

Figure 2:
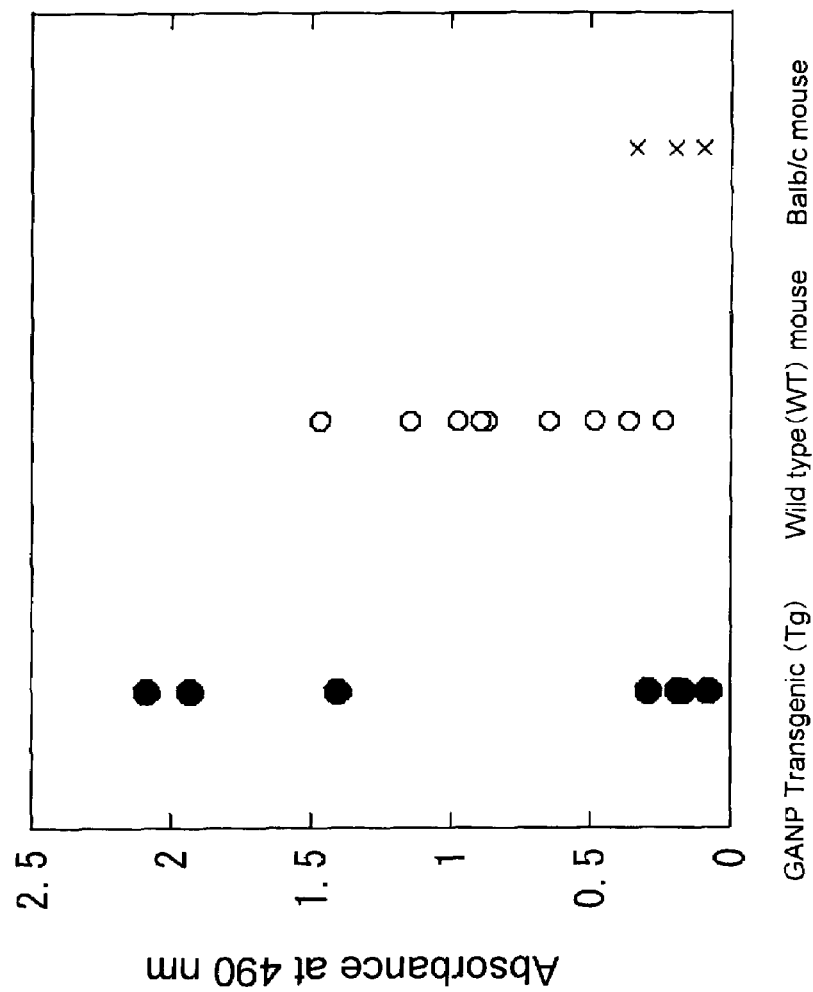
FIG. 2 is a graph showing the results of detection of gp120 (308-330) peptide with individual antibodies by ELISA.

The results of ELISA are shown in FIG. 2.

By using GANP-Tg mice, three antibodies with extremely high binding ability were produced (FIG. 2, absorbance around 1.4-2.1). These monoclonal antibody clones are G1-181, G2-10 and G2-25 according to descending order of absorbance.

Subsequently, the physicochemical binding ability of each antibody was examined with a Biacore system.

Briefly, HIV24NL43 peptide was bound to a Biacore sensor chip as a ligand. As analyte solutions, solutions of the anti-peptide monoclonal antibodies were used. Association rate constant (k ass), dissociation rate constant (k diss) and dissociation constant KD (KD=k diss/k ass) that is an indicator of affinity were calculated for each of the antibodies. The smaller the KD value is, the higher the affinity is evaluated.

Figure 3:
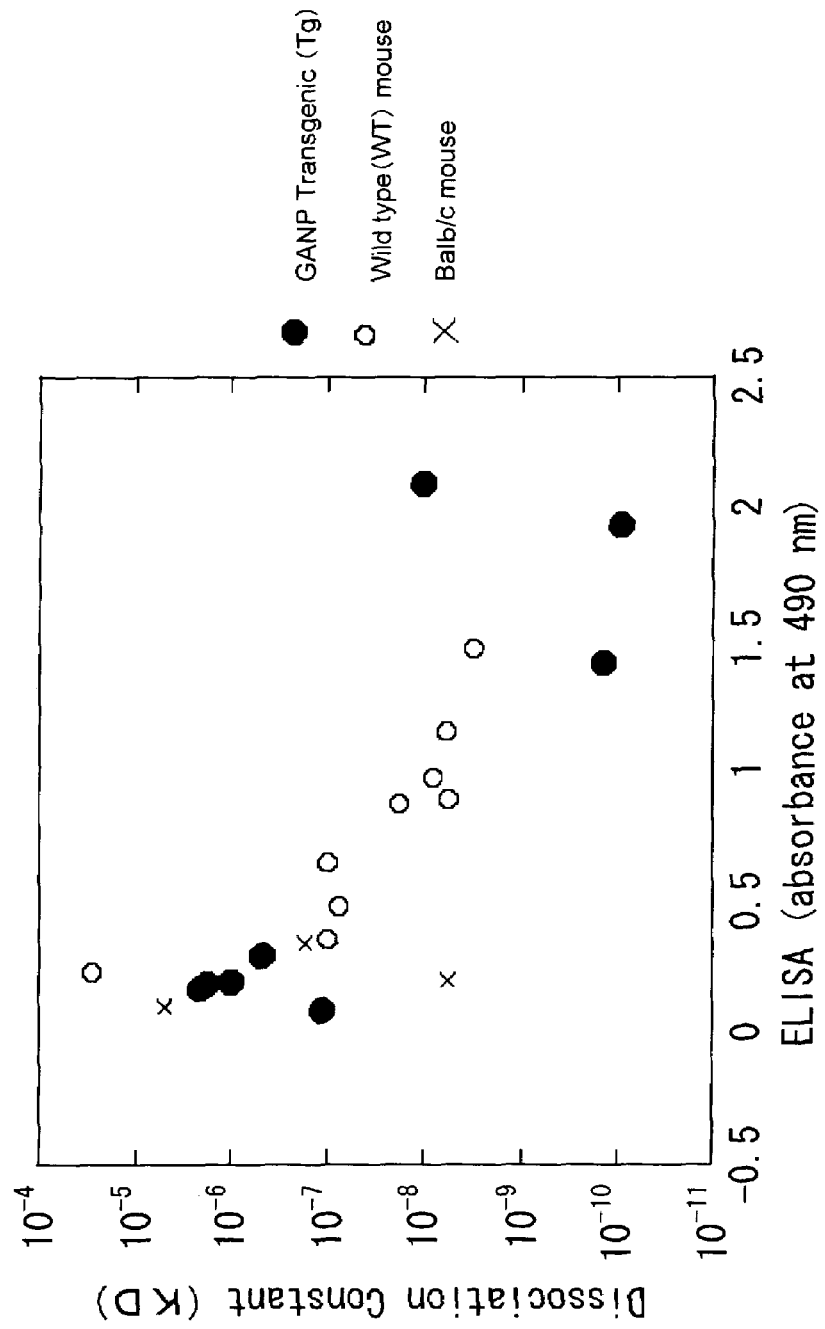
FIG. 3 is a graph showing the results of measurement of dissociation constant in individual clones.

As a comprehensive evaluation of the affinity of antibodies, the dissociation constant values and the results of ELISA for individual clones are shown in FIG. 3. In FIG. 3, relations between clones and dissociation constant values are as shown below.

| Clone | Dissociation Constant (M) |
|---|---|
| G1-181 | $1.09 \times 10^{-8}$ |
| G2-10 | $9.90 \times 10^{-11}$ |
| G2-25 | $1.51 \times 10^{-10}$ |

At present, measurement of sensitivity with a Biacore system is most effective for examining the binding affinity of antibodies. In this method, dissociation constant is conveniently calculated as a numerical value obtained by dividing the association rate constant of an antibody binding in a unit time by the dissociation constant of the bound antibody. With respect to the activity of antibodies, how quickly antibodies bind to the antigen is also an important factor in addition to the affinity to the antigen peptide. Antibodies are expected to bind to the virus in the living body as swiftly as possible, alter the molecular structure of the viral antigen and enter a still more firm state of binding. Although the binding affinity of clone G1-181 is not so high in view of the calculated dissociation constant value, this clone is excellent in the profile of association constant that this clone binds to a great number of antigen molecules most rapidly.

Usually, antibodies obtained from Balb/c mouse which is commonly used for monoclonal antibody preparation have a dissociation constant (KD) value of $4.97 \times 10^{-6}$ to $5.68 \times 10^{-9}$ (M), and thus are low affinity antibodies. Besides, only a small number of antibodies can be obtained. In wild type (WT) mouse which is a negative control, the dissociation constant (KD) value remained in a range from $2.81 \times 10^{-5}$ to $3.11 \times 10^{-9}$ (M); thus, binding affinity was limited.

On the other hand, it is possible to obtain a high affinity antibody (G2-10) with a dissociation constant (KD) value of $9.90 \times 10^{-11}$ (M) from GANP transgenic (Tg) mouse. The affinity of this antibody can be 57 times higher than that of Balb/c mouse clones and 31 times higher than that of wild type (WT) mouse clones.

EXAMPLE 4

Binding of the Monoclonal Antibodies to NL43 Envelope

A binding assay was performed to examine whether anti-HIV peptide (NL43) monoclonal antibodies prepared in Example 2 above have the binding ability to actual NL43 (HIV's envelope protein) in vitro.

(1) Materials (a) Anti-HIV (NL43) purified antibodies

The antibodies prepared in Example 2 were used. Specifically, the following antibodies were used.

Balb/c mouse: 3 clones (B1-10, B2-24 and B2-27)

Wild type (WT) mouse: 9 clones (W1-2, W1-7, W1-8, W1-10, W1-21, W1-43, W1-45, W1-63 and W1-84)

GANP transgenic (Tg) mouse: 8 clones (G1-22, G1-68, G1-124, G1-165, G1-181, G1-231, G2-10 and G2-25)

As controls, 70Z/3 2-28, 0.5β and anti-CD19 were used.

(b) Plasmid Vectors pLP-IRES2-EGFP (Clontech) and pLP-NL4-3 envelope-EGFP were used. By using these vectors, it becomes possible to translate both the gene of interest (NL43) and EGFP from a single RNA. Thus, almost 100% of the fluorescence-emitting cells express NL43.

(c) Gene Transfer Reagent

Effectene Transfection Reagent (QIAGEN) was used.

(d) Secondary Antibody

APC-labeled goat anti-mouse IgG antibody (BD Pharmingen) was used.

(2) Methods

In the binding assay, GFP is introduced into a human embryonic renal cancer cell line (293T cells) for monitoring the expression of envelope (NL43). The resultant cells are reacted with anti-HIV (NL43) purified antibodies and APC-labeled secondary antibody to thereby stain cell surfaces. Subsequently, two-color analysis is conducted by flow cytometry. Then, the binding ability to the envelope is evaluated with fluorescence intensity.

GFP gene was introduced into cells as described below. 400000 cells of human embryonic renal cancer cell line (293T cells) were plated in a 10 cm dish and cultured for one day. Then, pLP-IRES2-EGFP (Clontech) or pLP-NL4-3-EGFP (5 µg each) was introduced to the cells using Effectene Transfection Reagent. After a 36 hour culture, cells were collected and cell surfaces were stained. The staining of cell surfaces was performed using 10 µg/ml each anti-HIV (NL43) purified antibody and a 50-fold diluted APC-labeled goat anti-mouse IgG antibody. The cells were reacted with the anti-HIV antibody and the APC-labeled antibody for 30 minutes each on ice.

The binding ability of each anti-HIV monoclonal antibody to the envelope was evaluated by calculating mean fluorescence intensity (MFI) using FACS Calibur.

(3) Results

Figure 4:
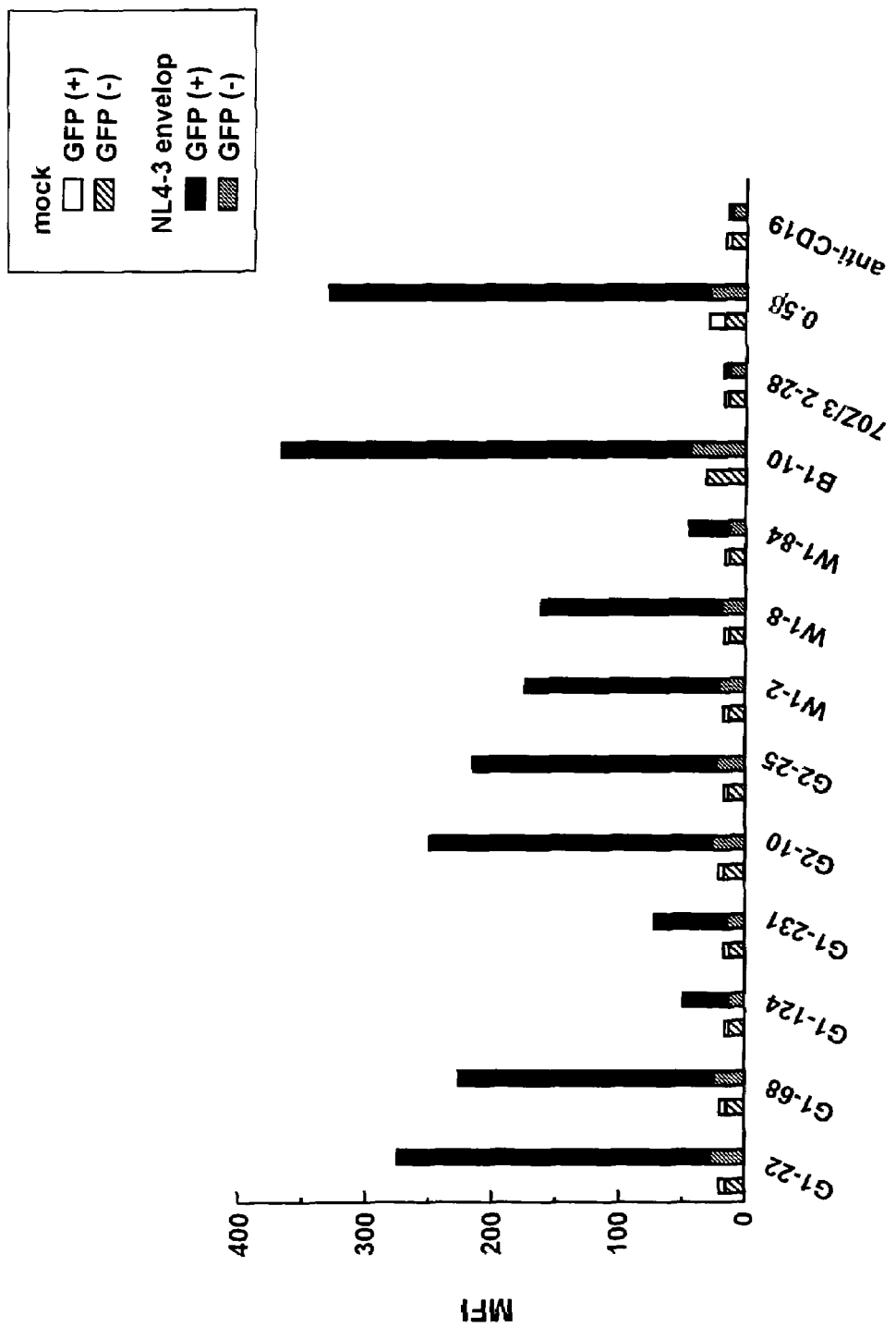
FIG. 4 is a graph showing the results of evaluation of the binding abilities of individual anti-HIV monoclonal antibodies to HIV envelope.
Figure 5:
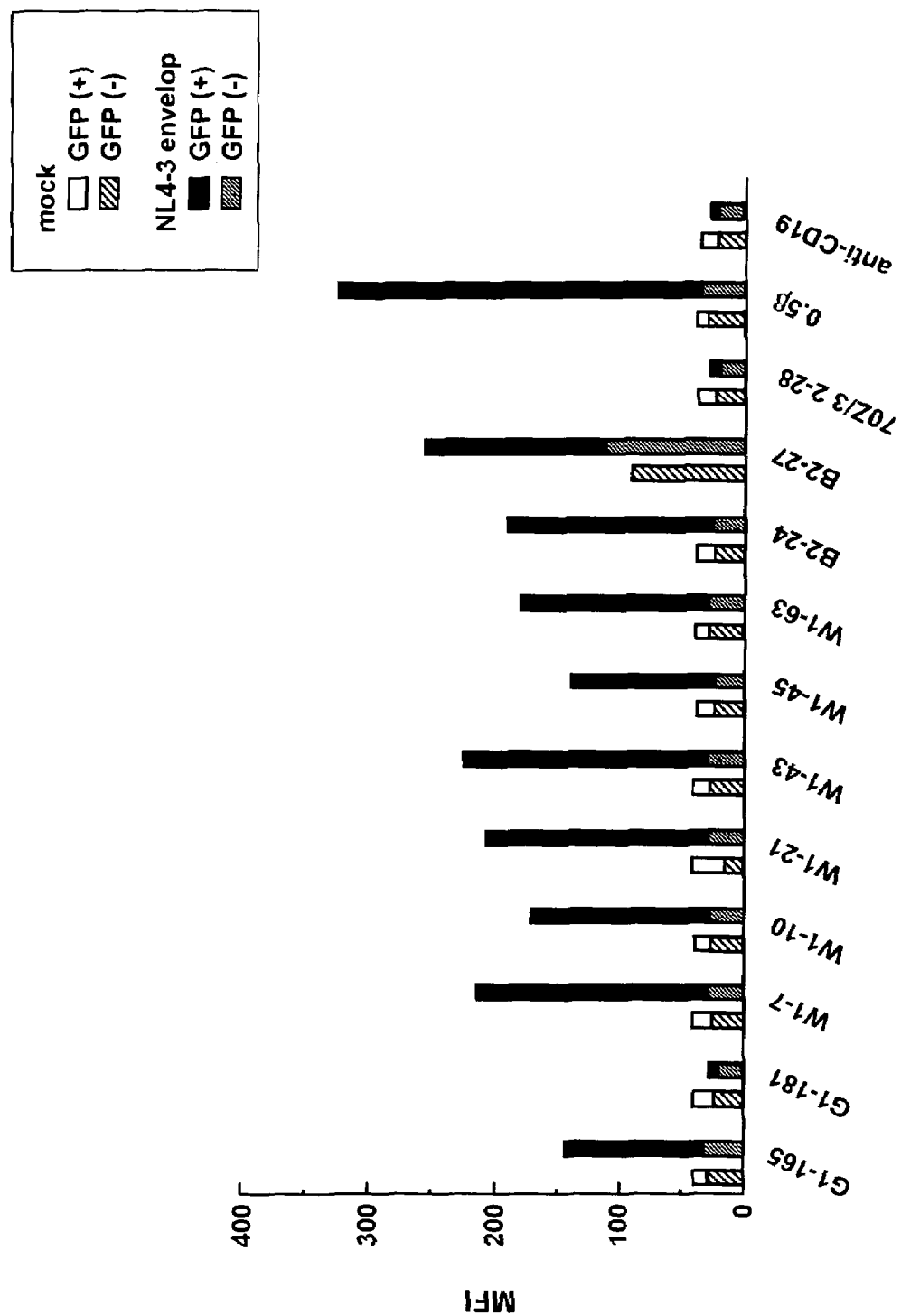
FIG. 5 is a graph showing the results of evaluation of the binding abilities of individual anti-HIV monoclonal antibodies to HIV envelope.

The results of the binding assay are shown in FIGS. 4 and 5. FIGS. 4 and 5 are bar graphs showing mean fluorescence intensity (MFI) when GFP positive (+) and GFP negative (−) cells were gated, respectively. These bar graphs show that in pLP-NL4-3 envelope-EGFP-introduced cells antibodies bind to the envelope more effectively when APC mean fluorescent intensity (NFI) in GFP positive cells is higher. The results of the binding assay revealed that monoclonal antibodies produced in GANP transgenic (Tg) mice (e.g., G1-22, G1-68, G2-10 and G2-25 clones) have the ability to bind to envelope.

EXAMPLE 5

Neutralizing Activities of Monoclonal Antibodies

In order to examine whether the purified monoclonal antibodies used in Example 4 actually have the ability to inhibit HIV-1 infection, a neutralizing activity experiment (viral infection inhibitory experiment) was conducted in human CD4 positive cells using the monoclonal antibodies.

(1) Materials (a) Anti-HIV (NL43) purified antibodies

Each of the anti-HIV (NL43) purified antibodies used in Example 4 was used. As controls, 70Z/3 2-28 and 0.5β were used.

(b) HIV-1 Stock Strain

PM1 cells grown in 10% inactivated fetal bovine serum-added RPMI-1640 medium and stored at −80° C. were used.

(c) β Galactosidase detection kit

Galacto-star (TROPIX) was used as a β galactosidase detection kit. In AIDS virus infection inhibitory (neutralizing activity) experiments, this kit detects the β galactosidase produced by CD4 cells (MAGI/CCR5) with a chemilumines-cence substrate (the Reed-Muench method) to thereby judge the death or survival of CD4 cells (viable cell count).

(2) Methods

When a specific amount of HIV is added to CD4 cells (MAGI/CCR5) after one day culture, β galactosidase becomes undetectable from AIDS virus-infected cells. In this system, the neutralizing activities of antibodies are measured as follows. Immediately before the addition of AIDS virus, anti-HIV (NL43) purified antibodies different in efficacy are added to the above-described MAGI/CCR5 cells in advance. Then, whether or not these antibodies can inhibit viral infection when HIV is added is evaluated using the yield of β galactosidase as an indicator.

This infection measuring system enables to determine with high sensitivity the amount of virus necessary for viral infection. As a result of pilot examination on MAGI/CCR5 cells, the amount of virus to be added was determined 500 based on the 50% endpoint tissue culture infectious dose (TCID50) of the virus.

In order to infect cells with HIV, MAGI/CCR5 cells were cultured in 96-well plates at a density of $1\times10^4$ cells/well. After one day, 50 µl of each antibody was added and incubated at 37° C. for 30 minutes. Subsequently, 50 µl of HIV-1 solution reacted with 10 µg/ml DEAE-dextran was added and incubated. Each of the antibodies was added at three different concentrations: 0.5, 5 and 50 µg/ml. After two days, β galactosidase activities were measured with Galacto-star (TROPIX).

(3) Results

Figure 6:
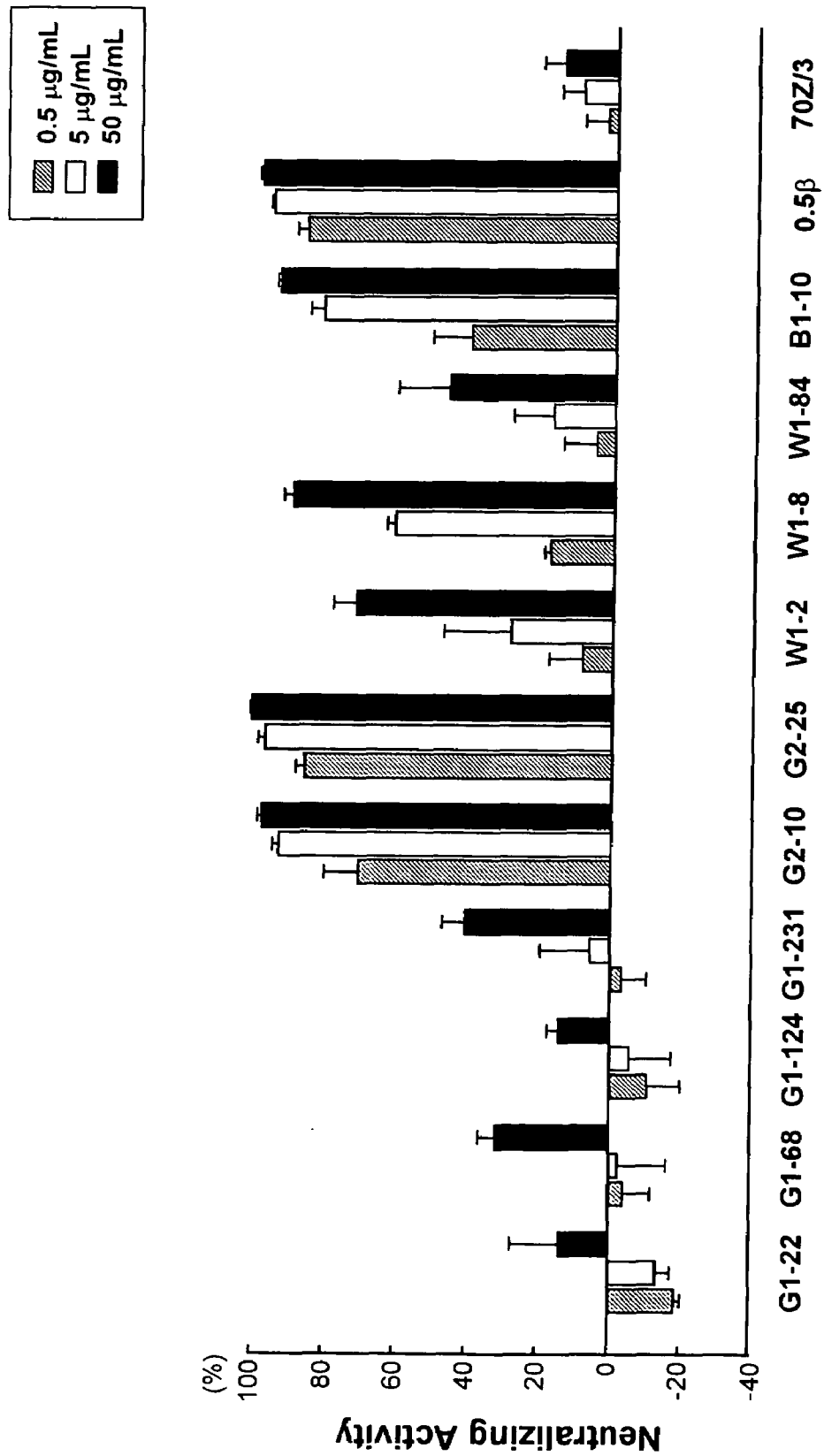
FIG. 6 is a graph showing the results of neutralizing activity test on individual anti-HIV monoclonal antibodies.
Figure 7:
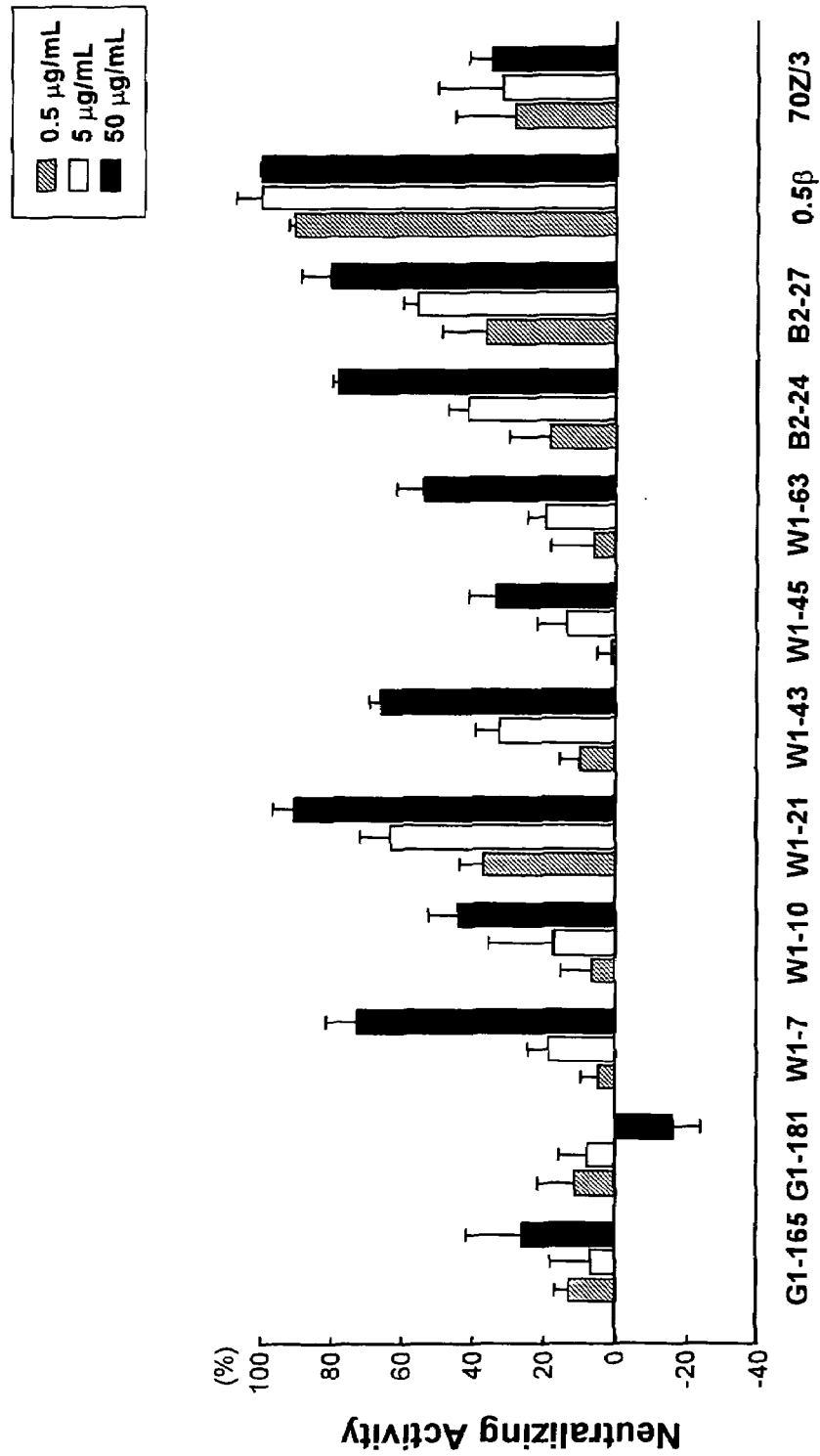
FIG. 7 is a graph showing the results of neutralizing activity test on individual anti-HIV monoclonal antibodies.

The results of the neutralizing activity experiment are shown in FIGS. 6 and 7. The results of measurement of the neutralizing activities of individual antibodies revealed that G2-10 and G2-25 clones produced by GANP transgenic (Tg) mice have the HIV neutralizing activities as shown in Table I at indicated concentrations.

TABLE 1

| Clone | Concentration | Neutralizing Activity (Infection Inhibitory Ability) |
|---|---|---|
| G2-10 | 50 µg/ml | 98.2% ± 1.2 |
|  | 5 µg/ml | 93.5% ± 1.7 |
|  | 0.5 µg/ml | 70.9% ± 9.7 |
| G2-25 | 50 µg/ml | 101.2% ± 0.4 |
|  | 5 µg/ml | 97.6% ± 1.6 |
|  | 0.5 µg/ml | 86.3% ± 2.4 |
| 0.5 β | 0.5 µg/ml | 86.5% ± 3.0 |

When the antibody is actually used as a therapeutic antibody, it is important for the antibody to have the ability to inhibit viral infection at an extremely low dose. From this viewpoint, the values achieved by G2-10 and G2-25 show that these antibodies manifest HIV infection inhibitory ability at extremely low concentrations and these antibodies may be considered to be used as effective HIV therapeutics.

As a positive control in the measurement of neutralizing activities, an antibody (0.5β) which is said to have been prepared by immunizing with HIV envelope itself (Japanese Patent No. 2797099) was used. The neutralizing activity of 0.5β at 0.5 µg/ml was as high as 86.5%±3.0. However, the in vitro infection inhibitory ability in the above two clones (in particular, G2-25) can be said equivalent or superior to that ability of this antibody (0.5β).

In contrast, the 9 antibody clones produced by wild type (WT) mice showed almost no neutralizing activity at a low concentration of 0.5 µg/ml.

The results obtained in Examples 4 and 5 show that the anti-AIDS peptide (NL43) monoclonal antibodies produced in GANP transgenic (Tg) mice actually bind to HIV-1 viral envelope in vitro (Example 4) and that this binding has a strong neutralizing activity (infection inhibitory effect) (Example 5). More importantly, since these monoclonal antibody show a dissociation constant (KD) value of $9.90\times10^{-11}$, they are a group of high affinity antibodies which are capable of binding to the virus for a long period once they have bound thereto (Example 3).

High affinity monoclonal antibodies that have such a strong virus neutralizing effect and have remarkable low rate of dissociating with antigen are excellent antibodies which cannot be prepared by the conventional monoclonal antibody preparation attempted by a great number of laboratories based on a peptide sequence deduced from the genetic sequence of HIV-1 virus. While those monoclonal antibodies prepared by immunizing wild type C57BL/6 mice show a high neutralizing activity only at a concentration of 50 μg/ml, both of GANP transgenic (Tg) mice-derived G2-10 and G2-25 monoclonal antibodies manifest a neutralizing activity equivalent to thereto at an extremely low concentration of 0.5 μg/ml. According to simple calculation, the latter antibodies show 100-fold higher neutralizing activity per protein concentration, and the binding of the latter antibodies is expected to last for a longer period by the order of $10^2$.

These mouse anti-HIV-1 monoclonal antibodies have the following advantages: (a) they are high affinity antibodies specific to a viral peptide sequence; (b) they actually bind to HIV-1 envelope in vitro; (c) they are capable of inhibiting HIV-1 infection of human CD4 positive cells in vitro; (d) they may be antibodies to a novel epitope because they are produced by a mutant mouse not used in conventional methods; (e) this new VH region provides basic information for preparing still powerful antibodies by adding further genetic alteration by biotechnology.

The fact that it is possible to obtain swiftly high affinity antibodies having AIDS virus infection inhibitory effect using GANP transgenic (Tg) mice proves that the results of researches so far made and the plan of application thereof are reasonable. Therefore, the present invention is extremely useful as an invention which leads to development of an epoch-making therapy in the modern world threatened by infectious disease.

Sequence Listing Free Text
 SEQ ID NO: 7: primer
 SEQ ID NO: 8: primer

INDUSTRIAL APPLICABILITY

According to the present invention, a high affinity anti-HIV antibody obtainable from a GANP gene transgenic non-human mammal and a pharmaceutical composition comprising the antibody are provided. Since the antibody of the invention has high affinity represented by its dissociation constant (KD) value of $1.0\times10^{-9}$ (M) or less, a pharmaceutical composition comprising the antibody of the invention may be used as a therapeutic for acquired immunodeficiency syndrome (AIDS).

Further, according to the present invention, a cell producing the antibody and an HIV detection kit using the antibody are also provided.

The invention claimed is:

1. A monoclonal antibody to the gp120 glycoprotein of HIV, which is produced by a hybridoma cell having an accession number of FERM BP-08644, or a fragment thereof possessing affinity for HIV glycoprotein gp120.

2. A humanized antibody or a human antibody which binds to the gp120 glycoprotein of HIV, and which comprises a V region of an antibody produced by a hybridoma having an accession number of FERM BP-08644, or a fragment thereof possessing affinity for HIV glycoprotein gp120.

3. A cell producing a monoclonal antibody to the gp120 glycoprotein of HIV, which has an accession number of FERM BP-08644.

4. A method of producing an anti-HIV antibody, comprising culturing the monoclonal antibody-producing cell according to claim 3, and collecting the antibody from the resultant culture.

5. A method of detecting HIV, comprising reacting the antibody or fragment thereof according to claim 1, or the humanized antibody or human antibody or fragment thereof according to claim 2, with the gp120 glycoprotein of HIV.

6. An HIV detection kit comprising at least one selected from the group consisting of the antibody or fragment thereof according to claim 1, and the humanized antibody or human antibody, or fragment thereof according to claim 2.

7. The monoclonal antibody or fragment thereof of claim 1, wherein the antibody produced by the hybridoma is the monoclonal antibody.

8. The monoclonal antibody or fragment of claim 1, wherein the antibody or fragment produced by the hybridoma is the monoclonal antibody fragment.

9. The human antibody or fragment thereof or the humanized antibody or fragment thereof of claim 2, where the antibody or fragment is the human antibody or the humanized antibody.

10. The human antibody or fragment thereof or the humanized antibody or fragment thereof of claim 2, wherein the antibody or fragment thereof is the human antibody fragment or the humanized antibody fragment.

* * * * *